(12) United States Patent
Raanani et al.

(10) Patent No.: US 12,097,114 B2
(45) Date of Patent: *Sep. 24, 2024

(54) VENTRICULAR STRUCTURE RESHAPING ATRIO-VENTRICULAR VALVE

(71) Applicant: TEL HASHOMER MEDICAL RESEARCH INFRASTRUCTURE AND SERVICES LTD., Ramat-Gan (IL)

(72) Inventors: Ehud Raanani, Hod-HaSharon (IL); Boris Orlov, Haifa (IL); Boaz Harari, Haifa (IL); Oded Meiri, Moshav Ram-On (IL); Lichen Rozitsky, Haifa (IL)

(73) Assignee: TEL HASHOMER MEDICAL RESEARCH INFRASTRUCTURE AND SERVICES LTD., Ramat-Gan (IL)

( * ) Notice: Subject to any disclaimer, the term of this patent is extended or adjusted under 35 U.S.C. 154(b) by 190 days.

This patent is subject to a terminal disclaimer.

(21) Appl. No.: 17/932,014

(22) Filed: Sep. 14, 2022

(65) Prior Publication Data

US 2023/0000622 A1 Jan. 5, 2023

Related U.S. Application Data

(63) Continuation of application No. 17/349,152, filed on Jun. 16, 2021, now Pat. No. 11,779,459, which is a (Continued)

(51) Int. Cl.
*A61F 2/24* (2006.01)
(52) U.S. Cl.
CPC ............ *A61F 2/2418* (2013.01); *A61F 2/243* (2013.01); *A61F 2/2436* (2013.01); *A61F 2/2457* (2013.01);
(Continued)

(58) Field of Classification Search
None
See application file for complete search history.

(56) References Cited

U.S. PATENT DOCUMENTS

| 7,018,408 | B2 | 3/2006 | Bailey et al. |
| 7,621,948 | B2 | 11/2009 | Herrmann et al. |

(Continued)

FOREIGN PATENT DOCUMENTS

| CA | 2606101 A1 | 11/2006 |
| CA | 2898991 A1 | 8/2014 |

(Continued)

OTHER PUBLICATIONS

Extended European Search Report for European Application No. 23162937.9 mailed Jun. 21, 2023.

(Continued)

*Primary Examiner* — Brooke Labranche
*Assistant Examiner* — Lindsey Bachman
(74) *Attorney, Agent, or Firm* — Dorsey & Whitney LLP

(57) ABSTRACT

Apparatus and methods are described including placing a valve frame within a subject's heart. The valve frame includes a valve frame body that is configured to support the prosthetic valve within the native atrio-ventricular valve, and at least one arm that is configured to extend from a ventricular portion of the valve frame. The at least one arm is deployed among chords of the native atrio-ventricular valve. Subsequently, at least a portion of the valve frame is rotated in a direction in which an interior of the arm faces, such as to modify shapes of the native valve leaflets and the ventricular structures, by recruiting and deflecting at least a portion of the chords. The frame body of the valve frame is then radially expanded, such as to hold the native valve leaflets and the ventricular structures at least partially in the modified shapes. Other applications are also described.

26 Claims, 42 Drawing Sheets

Related U.S. Application Data continuation of application No. 16/374,240, filed on Apr. 3, 2019, now Pat. No. 11,065,114, which is a continuation of application No. 14/402,387, filed as application No. PCT/IL2013/050432 on May 20, 2013, now Pat. No. 10,292,816.

(60) Provisional application No. 61/649,319, filed on May 20, 2012.

(52) U.S. Cl.
CPC ............. *A61F 2220/0008* (2013.01); *A61F 2220/0016* (2013.01); *A61F 2220/0058* (2013.01); *A61F 2220/0075* (2013.01); *A61F 2230/0013* (2013.01); *A61F 2230/005* (2013.01); *A61F 2230/0078* (2013.01); *A61F 2250/006* (2013.01)

(56) References Cited

U.S. PATENT DOCUMENTS

| | | | |
|---|---|---|---|
| 7,748,389 B2 | 7/2010 | Salahieh et al. | |
| 7,753,949 B2 | 7/2010 | Lamphere et al. | |
| 8,070,802 B2 | 12/2011 | Lamphere et al. | |
| 8,870,950 B2 | 10/2014 | Hacohen | |
| 9,364,326 B2 | 6/2016 | Yaron | |
| 9,700,412 B2 | 7/2017 | Yaron et al. | |
| 9,949,830 B2 | 4/2018 | Solem | |
| 10,105,217 B2 | 10/2018 | Keränen | |
| 10,130,471 B2 | 11/2018 | Keränen et al. | |
| 10,238,489 B2 | 3/2019 | Conklin | |
| 10,292,816 B2 | 5/2019 | Raanani et al. | |
| 10,292,850 B2 | 5/2019 | Vad et al. | |
| 10,500,038 B1 | 12/2019 | Orlov et al. | |
| 11,065,114 B2 | 7/2021 | Raanani et al. | |
| 11,583,394 B2 | 2/2023 | Orlov et al. | |
| 2002/0065554 A1 | 5/2002 | Streeter | |
| 2003/0014104 A1 | 1/2003 | Cribier | |
| 2003/0083742 A1 | 5/2003 | Spence et al. | |
| 2004/0138745 A1 | 7/2004 | Macoviak et al. | |
| 2005/0165479 A1 | 7/2005 | Drews et al. | |
| 2006/0195134 A1 | 8/2006 | Crittenden | |
| 2006/0195184 A1 | 8/2006 | Lane et al. | |
| 2006/0241745 A1 | 10/2006 | Solem | |
| 2007/0016288 A1 | 1/2007 | Gurskis et al. | |
| 2007/0050020 A1 | 3/2007 | Spence | |
| 2007/0260305 A1 | 11/2007 | Drews et al. | |
| 2008/0039935 A1 | 2/2008 | Buch et al. | |
| 2009/0192585 A1 | 7/2009 | Bloom et al. | |
| 2009/0192586 A1 | 7/2009 | Tabor et al. | |
| 2009/0198324 A1 | 8/2009 | Orlov | |
| 2010/0022640 A1 | 1/2010 | Stoutamire | |
| 2010/0042208 A1 | 2/2010 | Herrmann et al. | |
| 2010/0049313 A1 | 2/2010 | Alon et al. | |
| 2010/0249923 A1 | 9/2010 | Alkhatib et al. | |
| 2010/0331971 A1 | 12/2010 | Keraenen et al. | |
| 2011/0029072 A1 | 2/2011 | Gabbay | |
| 2011/0137397 A1* | 6/2011 | Chau | A61F 2/2412 623/2.37 |
| 2011/0137410 A1* | 6/2011 | Hacohen | A61F 2/2445 623/2.37 |
| 2011/0224785 A1 | 9/2011 | Hacohen | |
| 2011/0264208 A1 | 10/2011 | Duffy et al. | |
| 2012/0010461 A1 | 1/2012 | Goldfarb et al. | |
| 2012/0022639 A1 | 1/2012 | Hacohen et al. | |
| 2012/0022640 A1* | 1/2012 | Gross | A61F 2/2427 623/2.11 |
| 2012/0101571 A1 | 4/2012 | Thambar et al. | |
| 2013/0035759 A1 | 2/2013 | Gross et al. | |
| 2013/0166022 A1 | 6/2013 | Conklin | |
| 2014/0031928 A1 | 1/2014 | Murphy et al. | |
| 2014/0088695 A1 | 3/2014 | Figulla et al. | |
| 2014/0088696 A1* | 3/2014 | Figulla | A61F 2/2418 623/2.17 |
| 2014/0222136 A1 | 8/2014 | Geist et al. | |
| 2015/0045880 A1 | 2/2015 | Hacohen | |
| 2015/0173897 A1 | 6/2015 | Raanani et al. | |
| 2015/0351903 A1 | 12/2015 | Morriss et al. | |
| 2015/0351908 A1 | 12/2015 | Kernen et al. | |
| 2015/0359628 A1 | 12/2015 | Keränen | |
| 2015/0374493 A1 | 12/2015 | Yaron et al. | |
| 2016/0095705 A1 | 4/2016 | Keränen et al. | |
| 2017/0128199 A1 | 5/2017 | Gurovich et al. | |
| 2017/0281338 A1 | 10/2017 | Quill et al. | |
| 2018/0014932 A1 | 1/2018 | Hammer et al. | |
| 2018/0177594 A1 | 6/2018 | Patel et al. | |
| 2018/0206992 A1 | 7/2018 | Brown | |
| 2019/0083245 A1 | 3/2019 | Hariton et al. | |
| 2019/0110893 A1 | 4/2019 | Haarer et al. | |
| 2019/0125534 A1 | 5/2019 | Arcaro et al. | |
| 2019/0231522 A1 | 8/2019 | Raanani et al. | |
| 2020/0100898 A1 | 4/2020 | Vola et al. | |
| 2020/0197175 A1 | 6/2020 | Chang et al. | |
| 2022/0010634 A1 | 1/2022 | Posa | |
| 2022/0015896 A1 | 1/2022 | Agian et al. | |
| 2022/0296370 A1 | 9/2022 | Agian et al. | |

FOREIGN PATENT DOCUMENTS

| | | |
|---|---|---|
| CN | 101180010 A | 5/2008 |
| CN | 102292053 A | 12/2011 |
| CN | 102438546 A | 5/2012 |
| CN | 104684505 A | 6/2015 |
| CN | 104994812 A | 10/2015 |
| DE | 102006052564 | 12/2007 |
| EP | 1850796 B1 | 12/2015 |
| EP | 3399947 A1 | 11/2018 |
| EP | 2948102 B1 | 1/2019 |
| EP | 2852354 B1 | 5/2020 |
| JP | 2008536592 A | 9/2008 |
| JP | 2011509806 A | 3/2011 |
| JP | 2012500665 A | 1/2012 |
| JP | 2012521222 A | 9/2012 |
| JP | 2014168694 A | 9/2014 |
| JP | 2015517376 A | 6/2015 |
| JP | 2016504134 A | 2/2016 |
| JP | 2018501001 A | 1/2018 |
| JP | 2019500965 A | 1/2019 |
| JP | 7051736 B2 | 4/2022 |
| WO | 0060995 A2 | 10/2000 |
| WO | 2004032724 A2 | 4/2004 |
| WO | 2005087140 A1 | 9/2005 |
| WO | 2006116558 A2 | 11/2006 |
| WO | 2007135101 A1 | 11/2007 |
| WO | 2009134701 A2 | 11/2009 |
| WO | 2010108079 A1 | 9/2010 |
| WO | 2012004679 A2 | 1/2012 |
| WO | 2012095116 A1 | 7/2012 |
| WO | 2013001339 A2 | 1/2013 |
| WO | 2013175468 A2 | 11/2013 |
| WO | 2014114795 A1 | 7/2014 |
| WO | 2015198125 A1 | 12/2015 |
| WO | 2018109329 A1 | 6/2018 |
| WO | 2018112429 A1 | 6/2018 |
| WO | 2020092096 A2 | 5/2020 |
| WO | 2020100050 A1 | 5/2020 |
| WO | 2021028867 A1 | 2/2021 |
| WO | 2022090881 A1 | 5/2022 |
| WO | 2022090882 A1 | 5/2022 |
| WO | 2022234468 A1 | 11/2022 |
| WO | 2022264082 A1 | 12/2022 |
| WO | 2023228028 A1 | 11/2023 |

OTHER PUBLICATIONS

International Search Report and Written Opinion from International Application No. PCT/IB2022/054099 mailed Sep. 12, 2022.
Invitation to Pay Additional Fees for International Application No. PCT/IB2022/054099 mailed Jul. 20, 2022.
Notice of Allowance for U.S. Appl. No. 17/349,152 mailed May 24, 2023.

(56) References Cited

OTHER PUBLICATIONS

Office Action for Canadian Application No. 3,149,527 mailed Mar. 6, 2023.
U.S. Appl. No. 16/106,000, filed Oct. 27, 2020.
U.S. Appl. No. 16/106,034, filed Oct. 27, 2020.
U.S. Appl. No. 18/248,394, filed Apr. 10, 2023.
U.S. Appl. No. 63/106,000, filed Oct. 27, 2020.
U.S. Appl. No. 63/106,034, filed Oct. 27, 2020.
International Search Report and Written Opinion from International Application No. PCT/IB2023/059084 mailed Feb. 12, 2024.
Invitation to Pay Additional Fees for International Application No. PCT/IB2023/059084 mailed Dec. 22, 2023.
Non-Final Office Action for U.S. Appl. No. 18/103,671 mailed Apr. 2, 2024.
Notice of Allowance for U.S. Appl. No. 17/263,776 mailed Apr. 9, 2024.
Office Action for Japanese Application No. 2022-508890 mailed Apr. 9, 2024.
Examination Report for Indian Application No. 202170217772 mailed Jan. 11, 2023.
Hearing Notice for Indian Application No. 2424/MUMNP/2014 mailed Jan. 3, 2023.
International Search Report and Written Opinion from International Application No. PCT/IB2022/055593 mailed Nov. 14, 2022.
Invitation to Pay Additional Fees for International Application No. PCT/IB2022/055593 mailed Sep. 23, 2022.
U.S. Appl. No. 17/263,776, filed Jan. 27, 2021.
U.S. Appl. No. 62/767,018, filed Nov. 14, 2018.
U.S. Appl. No. 63/184,403, filed May 5, 2021.
U.S. Appl. No. 63/184,427, filed May 5, 2021.
U.S. Appl. No. 63/211,602, filed Jun. 17, 2021.
Applicant-Initiated Interview Summary for U.S. Appl. No. 14/402,387 mailed Dec. 28, 2017.
Applicant-Initiated Interview Summary for U.S. Appl. No. 14/402,387 mailed May 25, 2017.
Final Office Action for U.S. Appl. No. 13/083,643 mailed Mar. 5, 2014.
Final Office Action for U.S. Appl. No. 13/475,994 mailed Jun. 8, 2018.
International Search Report and Written Opinion from International Application No. PCT/IB2023/055160 mailed Jul. 28, 2023.
Issue Notification for U.S. Appl. No. 13/475,994 mailed Nov. 20, 2019.
Issue Notification for U.S. Appl. No. 16/655,656 mailed Feb. 1, 2023.
Issue Notification for U.S. Appl. No. 17/349,152 mailed Sep. 20, 2023.
Non-Final Office Action for U.S. Appl. No. 13/475,994 mailed Dec. 28, 2018.
Non-Final Office Action for U.S. Appl. No. 17/263,776 mailed Oct. 25, 2023.
Non-Final Office Action for U.S. Appl. No. 17/488,623 mailed Oct. 26, 2023.
Non-Final Office Action for U.S. Appl. No. 17/488,628 mailed Oct. 26, 2023.
Notice of Allowance for U.S. Appl. No. 13/475,994 mailed Jul. 22, 2019.
Notice of Allowance for U.S. Appl. No. 16/655,656 mailed Oct. 25, 2022.
Office Action for Japanese Application No. 2021-525788 mailed Nov. 1, 2023.
U.S. Appl. No. 13/475,994, filed May 20, 2012.
U.S. Appl. No. 16/655,656, filed Oct. 17, 2019.
U.S. Appl. No. 18/103,671, filed Jan. 31, 2023.
U.S. Appl. No. 61/488,180, filed May 20, 2011.
Advisory Action for U.S. Appl. No. 14/402,387 mailed Mar. 1, 2018.
Communication Pursuant to Article 94(3) EPC Dated Jan. 8, 2018 From the European Patent Office Re. Application No. 13732633.6.
Communication Pursuant to Rule 94(3) for European Patent Application No. 20760551.0 mailed Apr. 7, 2022.
Communication Relating to the Results of the Partial International Search Dated Nov. 18, 2013 From the International Searching Authority Re. Application No. PCT/IL2013/050432.
Corrected Notice of Allowability for U.S. Appl. No. 14/402,387 mailed Mar. 20, 2019.
Examination Report for Australian Application No. 2013264730 mailed Dec. 20, 2017.
Examination Report for Australian Application No. 2013264730 mailed Jan. 13, 2017.
Examination Report for Australian Application No. 2018202951 mailed Dec. 6, 2018.
Examination Report for Australian Application No. 2019250140 mailed Oct. 19, 2020.
Examination Report for European Application No. 13732633.6 mailed Aug. 8, 2019.
Examination Report for Indian Application No. 2424/MUMNP/2014 mailed Aug. 31, 2020.
Final Office Action for U.S. Appl. No. 14/402,387 mailed Oct. 2, 2017.
Final Office Action for U.S. Appl. No. 13/475,994 mailed Jan. 10, 2017.
Final Office Action for U.S. Appl. No. 13/475,994 mailed Jun. 10, 2015.
International Preliminary Report on Patentability from International Application No. PCT/IL2013/050432 mailed Dec. 4, 2014.
International Search Report and Written Opinion for International Application No. PCT/IB2021/059798 mailed Jan. 24, 2022.
International Search Report and Written Opinion for International Application No. PCT/IB2021/059799 mailed Jan. 25, 2022.
International Search Report and Written Opinion from International Application No. PCT/IB2019/059734 mailed Feb. 6, 2020.
International Search Report and Written Opinion from International Application No. PCT/IB2019/059734 mailed Jan. 30, 2020.
International Search Report and Written Opinion from International Application No. PCT/IB2020/057636 mailed Oct. 29, 2020.
International Search Report and Written Opinion from International Application No. PCT/IL2013/050432 mailed Feb. 26, 2014.
Issue Notification for U.S. Appl. No. 14/402,387 mailed May 1, 2019.
Issue Notification for U.S. Appl. No. 16/374,240 mailed Jun. 30, 2021.
Non-Final Office Action for U.S. Appl. No. 13/475,994 mailed Apr. 1, 2016.
Non-Final Office Action for U.S. Appl. No. 13/475,994 mailed Oct. 1, 2014.
Non-Final Office Action for U.S. Appl. No. 13/475,994 mailed Sep. 11, 2017.
Non-Final Office Action for U.S. Appl. No. 14/402,387 mailed Dec. 23, 2016.
Non-Final Office Action for U.S. Appl. No. 14/402,387 mailed Sep. 20, 2018.
Non-Final Office Action for U.S. Appl. No. 16/655,656 mailed Jun. 17, 2022.
Notice of Allowance for U.S. Appl. No. 14/402,387 mailed Apr. 30, 2019.
Notice of Allowance for U.S. Appl. No. 14/402,387 mailed Jan. 30, 2019.
Notice of Allowance for U.S. Appl. No. 16/374,240 mailed Mar. 16, 2021.
Notice of Amendment Dated Jun. 23, 2017 From the State Intellectual Property Office of the People's Republic of China Re. Application No. 201710425696.6 and Its Machine Translation Into English.
Notice of Reason for Rejection Dated Feb. 14, 2017 From the Japan Patent Office Re. Application No. 2015-513347 and Translation.
Notification of Office Action and Search Report Dated Sep. 7, 2016 From the State Intellectual Property Office of the People's Republic of China Re. Application No. 201380038199.0.
Notification of Office Action Dated Dec. 3, 2015 From the State Intellectual Property Office of the People's Republic of China Re. Application No. 201380038199.0.

(56) References Cited

OTHER PUBLICATIONS

Notification of Office Action Dated Dec. 14, 2016 From the State Intellectual Property Office of the People's Republic of China Re. Application No. 201380038199.0 and Its Translation Into English.
Office Action for Australian Application No. 2018202951 mailed Apr. 1, 2019.
Office Action for Canadian Application No. 2,874,208 mailed Aug. 2, 2019.
Office Action for Canadian Application No. 2,874,208 mailed Feb. 19, 2019.
Office Action for Chinese Application No. 20170425696.6 mailed May 19, 2020.
Office Action for Chinese Application No. 201710425696.6 mailed Nov. 4, 2019.
Office Action for Japanese Application No. 2017-184962 mailed Jul. 31, 2018.
Office Action for Japanese Application No. 2019/032726 mailed Feb. 18, 2020.
Office Action for Japanese Application No. 2019/032726 mailed Jan. 19, 2021.
Office Action for Japanese Application No. 2019/032726 mailed Nov. 19, 2021.
Restriction Requirement for U.S. Appl. No. 13/475,994 mailed Mar. 11, 2014.
Translation Dated Dec. 28, 2015 of Notification of Office Action Dated Dec. 3, 2015 From the State Intellectual Property Office of the People's Republic of China Re. Application No. 201380038199.0.
Translation of Notification of Office Action and Search Report Dated Sep. 7, 2016 From the State Intellectual Property Office of the People's Republic of China Re. Application No. 201380038199.0.
U.S. Appl. No. 12/582,986, filed Oct. 21, 2009.
U.S. Appl. No. 14/402,387, filed Nov. 20, 2014.
U.S. Appl. No. 16/374,240, filed Apr. 3, 2019.
U.S. Appl. No. 17/349,152, filed Jun. 16, 2021.
U.S. Appl. No. 17/488,623, filed Sep. 29, 2021.
U.S. Appl. No. 17/488,628, filed Sep. 29, 2021.
U.S. Appl. No. 61/649,319, filed May 20, 2012.
U.S. Appl. No. 62/886,366, filed Aug. 14, 2019.

\* cited by examiner

VENTRICULAR STRUCTURE RESHAPING ATRIO-VENTRICULAR VALVE

CROSS REFERENCES TO RELATED APPLICATIONS

This application is a continuation of U.S. Ser. No. 17/349,152 to Raanani (published as US 2021/0307901) filed on Jun. 16, 2021, which is a continuation of U.S. Ser. No. 16/374,240 to Raanani (issued as U.S. Pat. No. 11,065,114) filed on Apr. 3, 2019, which is a continuation of U.S. Ser. No. 14/402,387 to Raanani (issued as U.S. Pat. No. 10,292,816) filed Nov. 20, 2014, which is a US National Phase of International Application PCT/IL13/050432 to Raanani (published as WO 13/175468), filed May 20, 2013, which claims priority from U.S. Provisional Patent Application No. 61/649,319 filed May 20, 2012, the contents of which are incorporated herein by reference in their entirety.

FIELD AND BACKGROUND OF THE INVENTION

The present invention relates to the field of cardiac surgery, and more particularly to the field of prosthetic mitral valves.

The human heart is a muscular organ that pumps deoxygenated blood through the lungs to oxygenate the blood and pumps oxygenated blood to the rest of the body by rhythmic contractions of four chambers.

After having circulated in the body, deoxygenated blood from the body enters right atrium through the vena cava. The right atrium contracts, pumping the blood through a tricuspid valve into the right ventricle. The right ventricle contracts, pumping the blood through a pulmonary semi-lunar valve into the pulmonary artery which splits to two branches, one for each lung. The blood is oxygenated while passing through the lungs, and reenters the heart via the left atrium. The left atrium contracts, pumping the oxygenated blood through the mitral valve into the left ventricle. The left ventricle contracts, pumping the oxygenated blood through the aortic valve into the aorta to be distributed to the rest of the body. The mitral valve closes during left ventricle contraction, so that blood is prevented from backflow.

In the mitral valve, an approximately circular mitral annulus defines a mitral valve orifice. Attached to the periphery of the mitral annulus are an anterior leaflet and a smaller posterior leaflet. The leaflets are connected to papillary muscles at the bottom of left ventricle by chords. The typical area of the mitral lumen in a healthy adult is between 4 and 6 cm², while the typical total surface area of leaflets is significantly larger, approximately 12 cm².

During diastole (for example, atrial systole), the left atrium contracts to pump blood into the left ventricle through the mitral valve orifice. The blood flows through the orifice, pushing the leaflets apart and into the left ventricle with little resistance. The leaflets of the aortic valve are kept closed by blood pressure in the aorta.

During ventricular systole, the left ventricle contracts to pump blood into the aorta through the aortic valve, the leaflets of which are pushed open by the blood flow with relatively little resistance. The mitral annulus contracts, pushing the leaflets inwards and reducing the area of the mitral valve orifice by about 20% to 30%. The papillary muscles contract, maintaining the tension of the chords and pulling the edges of the leaflets, preventing prolapse of the leaflets into the left atrium. The leaflets are curved into the left ventricle and coapt to accommodate the excess leaflet surface area, producing a coaptation surface that constitutes a seal. The typical height of the coaptation surface in a healthy heart of an adult is approximately 7-8 mm. The pressure of blood in the left ventricle pushes against the ventricular surfaces of the leaflets, tightly pressing the leaflets together at the coaptation surface so that a tight, leak-proof seal is formed.

An effective seal of the mitral valve during ventricular systole depends on a sufficient degree of coaptation, in terms of length, area and continuity of coaptation surface. If coaptation surface is insufficient or non-existent, there is mitral valve insufficiency; that is, regurgitation of blood from the left ventricle into the left atrium during ventricular systole. A lack of sufficient coaptation may be caused by any number of physical anomalies that allow leaflet prolapse (for example, elongated or ruptured chords, or weak papillary muscles) or prevent coaptation (for example, short chords, or small leaflets). There are also pathologies that lead to a mitral valve insufficiency, including collagen vascular disease, ischemic mitral regurgitation (resulting, for example, from myocardial infarction, chronic heart failure, or failed/unsuccessful surgical or catheter revascularization), myxomatous degeneration of the leaflets, and rheumatic heart disease. Mitral valve insufficiency leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

Apart from humans, mammals that suffer from mitral valve insufficiency include horses, cats, dogs, cows, sheep and pigs.

It is known to use open-heart surgical methods to treat mitral insufficiency, for example by modifying the subvalvular apparatus (for example, lengthening or shortening chords) to improve leaflet coaptation, or by implanting an annuloplasty ring to force the mitral valve annulus into a normal shape.

Aortic valves are known to suffer from aortic insufficiency or aortic stenosis. It is known to deploy a prosthetic aortic valve using minimally invasive surgery to replace a malfunctioning native aortic valve. Typically, an expandable frame (for example, a stent or a ring) supporting artificial aortic leaflets is positioned inside the orifice of an aortic valve, typically endovascularly with a catheter passing through the aorta, but also transapically through a hole near the apex of the heart, passing into the left ventricle. The frame is expanded across the aortic annulus, folding and overlying the native aortic valve leaflets, and maintaining the prosthetic aortic valve in place by exertion of an axial force and by adopting an "hourglass" shape that distributes axial forces on the native aortic valve annulus and the surrounding tissue. Commercially available prosthetic aortic valves include the Lotus™ by Sadra Medical (Campbell, California, USA) and the CoreValve™ by Medtronic (Minneapolis, Minnesota, USA).

A challenge to deployment of a prosthetic mitral valve, analogous to a prosthetic aortic valve, is retention of the prosthesis in place during ventricular systole. Unlike the aortic valve annulus that constitutes a stable anchoring feature, especially when calcified, the mitral valve annulus is not a sufficiently stable anchoring feature (less than half of the mitral valve annulus is of fibrotic tissue) and is dynamic (changing size and shape as the heart beats). Further, unlike the aortic valve that is open during ventricular systole, the mitral valve must withstand the high pressures in the left ventricle caused by contraction of the left ventricle during ventricular systole, pressures that tend to force a mitral valve prosthesis deployed across a mitral valve annulus into the left atrium.

SUMMARY OF THE INVENTION

The present invention, in some embodiments thereof, relates to prosthetic heart valves, and in particular to prosthetic mitral valves. Some embodiments of the invention relate to methods and devices suitable for deploying prosthetic heart valves and in particular prosthetic mitral valves.

According to an aspect of the invention there is provided a prosthetic mitral valve suitable to be deployed in a mammalian heart, comprising: a valve frame; a frame aperture defined by the valve frame, said frame aperture sized to: circumferentially enclose a prosthetic heart valve mechanism and fit within the mitral valve aperture between the heart left ventricle and atrium; and at least one arm attached to the valve frame on the ventricular side of said frame aperture; said at least one arm having a chord receiving surface sized and shaped to deploy among a region of chords of the native mitral valve and deflect the shape of chords contacted, pulling least one native mitral valve leaflet at least partially around said frame aperture.

According to some embodiments of the invention, said chord receiving surface defines a chord capturing region, is shaped to guide encountered chords into said capturing region, and is shaped to bar chords entering said capturing region from exiting. According to some embodiments of the invention, said chord receiving surface is oriented with respect to a rotation direction and has at least one slope that guides chords encountered while moving in said rotation direction into said chord capturing region.

According to some embodiments of the invention, said chord receiving surface is oriented with respect to a rotation direction and has at least one hooked portion that prevents chords moving in opposition to said rotation direction from exiting said chord capturing region.

According to some embodiments of the invention, said at least one native mitral valve leaflet prevents the flow of blood between itself and said valve frame, at least in the direction passing from the left ventricle to the left atrium.

According to some embodiments of the invention, a portion of said valve frame on the atrial side of said frame aperture is too wide to pass through the mitral valve aperture.

According to some embodiments of the invention, said deflection of the shape of at least one chord is maintained after deployment at least by opposing force generated by contact of the frame with tissue of the heart on the atrial side of said frame aperture.

According to some embodiments of the invention, said deflection of the shape of at least one chord is maintained after deployment at least by opposing force generated by contact of the frame with tissue of the heart on the ventricular side of said frame aperture.

According to some embodiments of the invention, said deflection of the shape of at least one chord is maintained after deployment at least by opposing force generated by contact of the frame with at least one native mitral valve leaflet.

According to some embodiments of the invention, said deflection of the shape of at least one chord is maintained after deployment at least by opposing force generated by contact of the frame with at least one other chord which it deflects the shape of.

According to some embodiments of the invention, said valve frame comprises at least two metal parts secured to one another by at least one suture.

According to some embodiments of the invention, said frame is in a compact configuration upon delivery to the heart, and expands at least radially during deployment.

According to some embodiments of the invention, said frame at least partially in a compact configuration is at least partially crimped.

According to some embodiments of the invention, said valve frame in said compact configuration is less than 13 mm across at its largest profile diameter.

According to some embodiments of the invention, said valve frame in said compact configuration comprises least two mutually unattached parts.

According to some embodiments of the invention, one of said at least two mutually unattached parts comprises said at least one arm, and another of said at least two mutually unattached parts defines said frame aperture when deployed.

According to some embodiments of the invention, said at least two unattached parts are not overlapping in said compact configuration.

According to some embodiments of the invention, said at least two unattached parts are at least partially radially concentric in the deployed configuration of said valve.

According to some embodiments of the invention, one of said at least two partially radially concentric parts presses outwardly against the other so that the two said parts are constrained from moving over one another.

According to some embodiments of the invention, said at least radial expanding is at least partially actuated by application of a radially outwards force to an inner surface of said frame.

According to some embodiments of the invention, said at least radial expanding is at least partially self-actuated by said frame.

According to some embodiments of the invention, said valve mechanism is held within said aperture of the frame, and, when the frame is deployed, restricts fluid flow through the frame aperture in the direction from said ventricular side to said atrial side.

According to some embodiments of the invention, said valve mechanism comprises at least one prosthetic valve leaflet sized and positioned to restrict said fluid flow.

According to some embodiments of the invention, said valve mechanism becomes functional to restrict said fluid flow while at least part of said valve frame remains in said compact configuration.

According to some embodiments of the invention, said frame conforms to the shape of the beating heart without restricting its contractions.

According to some embodiments of the invention, native mitral valve leaflet is held between at least one member of said valve frame on both the ventricular and the atrial side of said native mitral valve leaflet.

According to some embodiments of the invention, at least one deployed arm of said at least one arms comprises: a basal region of attachment to said valve frame; and an extended member arising therefrom.

According to some embodiments of the invention, at least one deployed arm of said at least one arms comprises: a plurality of separated basal regions of attachment to said valve frame; a plurality of extended members arising therefrom and extending alongside one another; said members being joined at a region distal to said basal regions of attachment.

According to some embodiments of the invention, at least one deployed arm of said at least one arms extends radially from said valve frame in its position.

According to some embodiments of the invention, said deployed arm has a concavely rounded leading edge facing in a circumferential direction.

According to some embodiments of the invention, said concavely rounded leading edge curves through at least 90 degrees.

According to some embodiments of the invention, said concavely rounded leading edge curves through at least 180 degrees.

According to some embodiments of the invention, at least one deployed arm of said at least one arms comprises a branch point from which at least three member segments lead.

According to some embodiments of the invention, at least one of said member segments has a free end which projects toward the base of said deployed arm from said branch point.

According to some embodiments of the invention, said free end of said basally projecting member segment is within 5 mm of said branch point.

According to an aspect of the invention there is provided a catheter deployment system for deploying a prosthetic mitral valve comprising: a distal end with a central axis; a prosthetic mitral valve in a compact configuration disposed around said central axis; said prosthetic valve including at least a ventricular frame part; and a deployment clamp attached to the ventricular part, the deployment clamp being actuatable to induce rotation at least in said ventricular frame part.

According to some embodiments of the invention, the catheter deployment system comprises: a rotatable shaft; and a rotation actuator, coupled to the shaft at a distal end; said shaft being coupled at a distal end to said deployment clamp.

According to some embodiments of the invention, the deployment clamp comprises at least one prong connected at the prong end to said ventricular frame part.

According to some embodiments of the invention, said deployment clamp comprises at least one command wire in threaded contact with said ventricular frame part.

According to some embodiments of the invention, withdrawal of the at least one command wire from contact with the ventricular frame part releases said ventricular frame part.

According to some embodiments of the invention, said deployment clamp comprises at least one sleeve containing at least a portion of said ventricular frame part.

According to some embodiments of the invention, said deployment clamp comprises at least one command wire connected to said at least one sleeve; and a relative motion of said command wire retracts the sleeve from over said contained portion of said ventricular frame part releases said ventricular frame part.

According to some embodiments of the invention, in the catheter deployment system: a coupling mechanism couples said shaft to said rotation actuator; said coupling mechanism comprises a catch member and a detente; said catch member being caught by the detente; and one of said catch member and said detente being fixedly coupled to the rotation actuator, and the other of said catch member and said detente being fixedly coupled to said shaft.

According to some embodiments of the invention, said catch is removed from capture by said detente upon said rotation actuator exerting a torque on said coupling mechanism which exceeds a predetermined threshold.

According to an aspect of the invention there is provided a method of deploying a prosthetic mitral heart valve in a mammalian heart comprising: inserting a distal end of a prosthetic mitral heart valve catheter deployment system into the left heart ventricle; and extending arms attached to the prosthetic mitral valve into one or more regions occupied by chords of the native mitral valve leaflets.

According to some embodiments of the invention, the method further comprises rotating the extended arms.

According to some embodiments of the invention, the method further comprises locking the extended arms into position.

According to an aspect of the invention there is provided a valve frame of a prosthetic mitral valve comprising: at least two metal parts; a suture wire; and a polymer insert; said parts being sutured together by said suture wire; said suture wire being held off the surface of said parts by said polymer insert.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
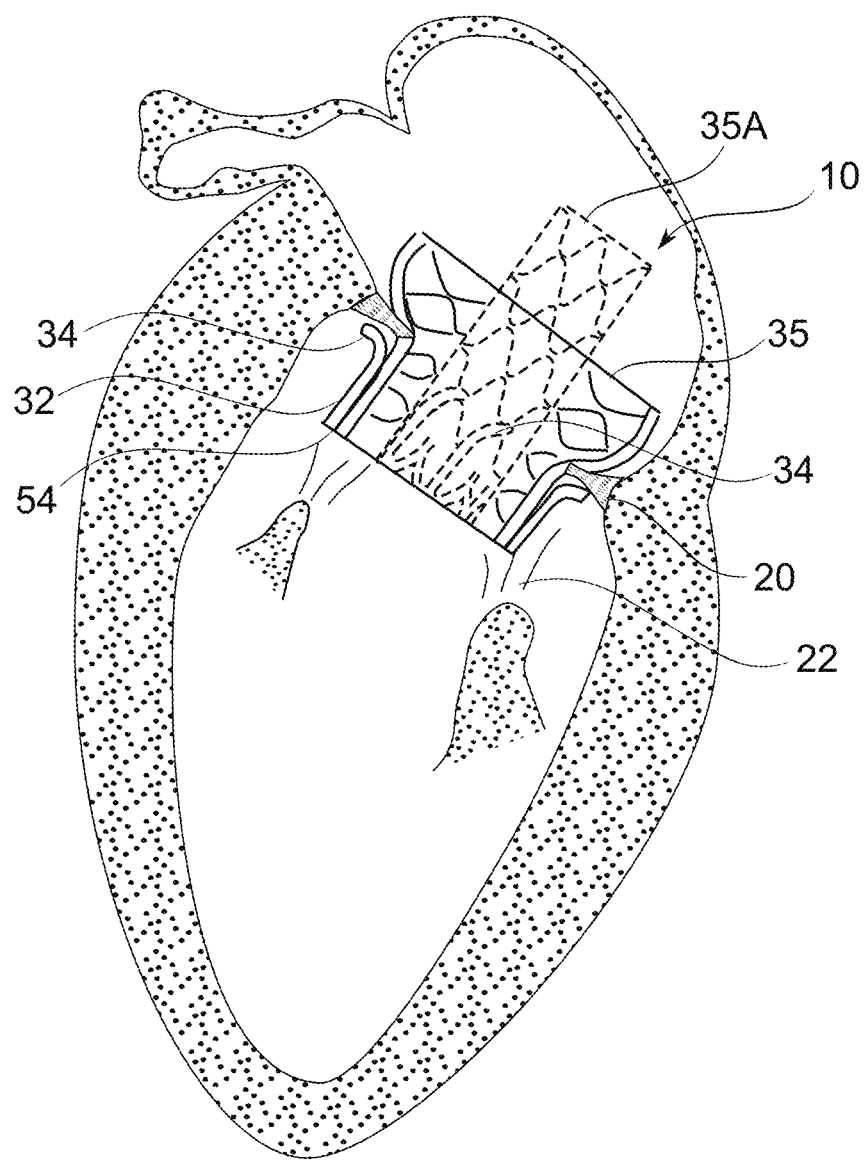
FIG. 1 schematically depicts the deployment of a prosthetic mitral valve of a normal adult human heart, to better help understand some embodiments of the invention.

The present invention, in some embodiments thereof, relates to prosthetic heart valves, and in particular to prosthetic mitral valves. Some embodiments of the invention relate to methods and devices suitable for deploying prosthetic heart valves and in particular prosthetic mitral valves.

The principles, uses and implementations of the teachings of the invention may be better understood with reference to the accompanying description and figures. Upon perusal of the description and figures present herein, one skilled in the art is able to implement the teachings of the invention without undue effort or experimentation.

Overview

An aspect of some embodiments of the present invention relates to the fixation and functional deployment of a prosthetic mitral valve within a functioning heart using tension applied to the chords of the mitral valve to recruit native valve leaflets into the fixating mechanism and/or functional characteristics of the valve.

In some embodiments of the invention, the chords and/or leaflets of the native mitral valve are pulled into and maintained under tension by capturing arms of the prosthetic mitral valve frame. In some embodiments, arms are structures, attached to the frame, which engage the native mitral valve chords and recruit them to a role in fixation of the prosthetic mitral valve. In some embodiments, arms are elongated structures deployed inside the ventricle. In some embodiments, arms are basally attached to portions of frame, and protrude outward from a core region of the frame to regions where they encounter the chords of the native mitral valve. In some embodiments, tensioning of the chords is at least in part by their displacement and/or by deflection of their shape as arms extend to within regions traversed by the chords.

In some embodiments, tensioning of the chords involves rotation of the arms with respect to the ventricle during frame deployment, by which chords encountered by the arms are captured (grasped). In some embodiments, tensioning of the chords shortens the distance between their attachment points by, for example, 2 mm, 5 mm, 10 mm, 15 mm, or another distance in between. In some embodiments, the percentage of chords captured is 10%, 20%, 40%, 80%, or 100%. In some embodiments, the independent percentage of chords captured in one or more of the primary, secondary, and tertiary chordae is 10%, 20%, 40%, 80%, or 100%.

In some embodiments of the invention, the movement of and/or development of tension in captured chords is assisted by protrusions on the arms and/or structures associated with the arms such supporting struts and/or rims. Potentially, protrusions, for example, restrain chords to the arms under tension by preventing their free movement; and/or assist in positioning the chord so that it pulls the native valve leaflets into position for use in frame fixation.

In some embodiments, tension on the chords is transmitted through the frame of the prosthetic mitral valve to play a role in fixation at other locations on the frame. For example, in some embodiments members of the frame located in the atrium are pressed against the atrial wall by rotational and/or tension forces transmitted through the frame from captured and tensioned native valve chords.

An aspect of some embodiments of the present invention relates to trapping and/or holding the leaflets of the native mitral valve in a partially closed configuration around an aperture of the implanted prosthetic valve. In some embodiments, the native leaflets are positioned to form an at least partial seal around the aperture of the implanted prosthetic valve which contains the valve mechanism. In some embodiments, tension on the chords is used to pull the native valve leaflets into a configuration which is at least partially closed around the prosthetic mitral valve frame. In some embodiments, the length of close of axial association of the native valve leaflets along the prosthetic mitral valve frame is in a range between 2 mm and 40 mm; for example, 2 mm to 40 mm, 2 mm to 10 mm, or 5 mm to 20 mm. In some embodiments, native valve leaflets are maintained in a partially closed position at least in part by continued tension on the chords. In some embodiments, increased tension on the chords, for example during contraction of the left ventricle, acts to further close the native valve leaflets around the prosthetic mitral valve, and in particular, the prosthetic mitral valve mechanism.

In some embodiments of the invention, native valve leaflets are maintained in a partially closed position at least in part by direct interactions with frame components in the atrial and/or ventricular compartments of the heart. In some embodiments, the leaflets are pressed between atrial and ventricular frame parts. In some embodiments, the structural members of the frame press the leaflets against one or more layers of material, such as a fabric, which covers at least a portion of the frame. In some embodiments, the atrial and ventricular mitral valve frame parts comprise projections which pierce the leaflets, thereby holding them in position.

An aspect of some embodiments of the present invention relates to the deployment of a prosthetic mitral valve, and in particular the frame of a prosthetic mitral valve, where at least one frame component is rotated during deployment. In some embodiments, the frame is inserted into the heart in a compact (for example, crimped) condition, for example, contained within a catheter deployment system. In some embodiments, the frame is deployed in stages, for example, a ventricular stage and an atrial stage.

In some embodiments of the invention, ventricular structures comprising grasping arms undergo a conformational change during deployment which moves them to their functional position; for example by an expansion from a central core, or by assuming a curvature. In some embodiments, the conformational change is in response to a triggering motion and/or other deployment force exerted through the catheter deployment system. In some embodiments, expansion is triggered by the retraction of an overtube which otherwise maintains the compact configuration of the ventricular part.

In some embodiments of the invention, a rotation component of the catheter deployment system attaches to and rotates ventricular structures of the prosthetic mitral valve frame, including arms. In some embodiments, rotation recruits chords into frame fixation. In some embodiments, the catheter deployment system is configured to maintain attachment, for example, through an attachment fork, even while the ventricular part structures undergo expansion. In some embodiments, the rotation component continues to exert force to maintain the rotated position while atrial part expansion and deployment occurs. In some embodiments, the fork of the rotation component is provided with a mechanism to allow release of the frame once deployment of the mitral valve frame parts reaches a particular stage of completion. Optionally, rotation is confined to a rotational component subsystem of the catheter deployment system and the prosthetic mitral valve parts affixed to it.

An aspect of some embodiments of the present invention relates to safe deployment of a prosthetic mitral valve, and in particular limitation and control of rotation of a prosthetic mitral valve frame component during deployment. In some embodiments of the invention, a rotation control is provided with a limited range of deployment available. In some embodiments, rotation of the prosthetic mitral valve frame is coupled to the rotation control through a device which does not transmit more than a limited maximum force and/or amount of rotation to the rotating prosthetic parts.

An aspect of some embodiments of the present invention relates to connecting the atrial and ventricular parts of the prosthetic mitral valve frame. In some embodiments parts are connected before deployment. In some embodiments, parts connect with one another as a part of deployment, for example during or as a result of part expansion or rotation. In some embodiments, parts are connected after deployment. In some embodiments where parts are connected during or after a phase of deployment, only a part of the prosthetic mitral valve frame rotates during deployment.

In some embodiments of the invention, parts are connected by shapes which interlock. For example, in some embodiments an atrial frame part expands inside a ventricle frame part, assuming a shape that forces the two parts to maintain a tight physical association. In some embodiments, shapes project from one or both parts, and interfere with one or more structural or other members of the mating part. In some embodiments, deployment expansion is accompanied by movements and/or shape changes which create locking associations between frame parts.

In some embodiments of the invention, parts comprise one or more connection apertures. In some embodiments, apertures are connected by suturing. In some embodiments of the invention, parts are connected through apertures by one or more fitted pieces and/or piece assemblies such as screws and nuts. In some embodiments of the invention, regions of connecting contact between parts are protected by intervening soft material; for example, fabric, silicone elastomer, or a plastic polymer.

An aspect of some embodiments of the present invention relates to flexibility of the frame of the implanted prosthetic mitral valve. In some embodiments, a portion of the frame, for example, a middle portion of the atrial part, is provided with elastic members which compress upon receiving a dynamic force—for example, due to the contraction of the atrium—and expand again when the force is no longer exerted. Potentially, dynamic adjustment in size helps maintain fixation contact and sealing throughout the heartbeat cycle while permitting the heart a fuller range of its original dynamic pumping motion. Depending on the specific frame member and the forces it receives, elastic motion may be through a range, for example of 1 mm, 3 mm, 5 mm or a range in between.

Overview of Some Embodiments of the Invention
Characteristics of Environment and Operation An aspect of some embodiments of the present invention relates to a prosthetic mitral valve comprising two frame parts, an atrial part and a ventricular part. The frame parts are provided with multiple structural aspects directed toward maintaining fixation of the prosthetic mitral valve within the dynamic environment of the living heart. Knowledge of the relationship of the structures of the frame to the tissues of the heart helps promote an understanding of the present invention.

When the prosthetic mitral valve is properly deployed, the atrial part is deployed inside a left atrium surrounding the mitral valve annulus, with a proximal portion thereof passing into (and in some embodiments through) the mitral valve annulus. The ventricular part of the prosthetic mitral valve deploys inside the left ventricle and grasps the chords and/or leaflets of the mitral valve.

In some embodiments, the atrial part of the prosthetic mitral valve has a diameter larger than that of the native mitral valve orifice.

In some embodiments, the ventricular part of the prosthetic mitral valve grasps the native mitral valve chords and/or leaflets by arms. Grasping recruits the native chords, and leaflets are recruited to seal the space between the native and the prosthetic mitral valve. In some embodiments, chords and/or leaflets are rotated around the mitral valve axis by rotating at least a part of the prosthetic mitral valve.

In some embodiments, the atrial and/or the ventricular parts exert axial forces preventing movement of the prosthetic mitral valve into the left atrium. In some embodiments, the atrial and the ventricular parts exert axial forces preventing rotational movement of chords and leaflets.

In some embodiments, at least the atrial part is at least partially sheathed in an expandable gripping sheath which the expanded atrial part presses against the native leaflets when deployed. Potentially, this provides an advantage for secure gripping of the native leaflets. In some embodiments, one or more of the atrial part and the ventricular part are provided with barbs which partially or fully penetrate tissue, for example a native valve leaflet, when deployed. Potentially, this provides an advantage for secure positioning of the prosthetic valve.

Prosthetic Mitral Valve Frame

According to an aspect of some embodiments of the invention there is provided a prosthetic mitral valve suitable for deployment in a mammalian heart. The prosthetic mitral valve of these embodiments comprises a frame functionally associated with the valve mechanism. In some embodiments of the invention, the frame comprises two major structural parts, atrial and ventricular. In particular, there is provided:

a. an atrial part defining a prosthetic mitral valve lumen and having a proximal portion; the atrial part having a deployed configuration configured for deployment inside a left atrium of a heart wherein its proximal portion passes into the mitral valve annulus of the heart; and b. a ventricular part, configured for deployment in a left ventricle of a heart, including arms for grasping the chords and/or leaflets of the mitral valve.

The association of the two parts with each other and with the heart comprises a portion of their function.

In some embodiments of the invention, in the deployed configuration the atrial part of the prosthetic mitral valve is shaped with an inverted shoulder, having a narrower (axial dimension) proximal portion and a wider (axial dimension) distal portion. When properly deployed in a heart, the shoulder of the wider distal part rests against the inner walls of the left atrium in proximity of the native mitral valve annulus, preventing the prosthetic mitral valve from moving into the left ventricle. When deployed in a heart, the proximal portion passes into the mitral valve annulus, and in some embodiments into the left ventricle, and in some embodiments even past the edges of the native mitral valve leaflets.

In some embodiments of the invention, in the deployed configuration the ventricular part of the prosthetic mitral valve is torus-shaped and includes at least one arm stemming radially. In some embodiments, arms are the structural members which recruit the chords of the native mitral valve into association with the prosthetic mitral valve, providing potential advantages as described herein.

In some embodiments of the invention, deployed arms project radially outward from the ventricular part and are shaped to contact the native chords and/or leaflets of the mitral valve. When rotated, the arms further induce a torsion force on these parts of the mitral valve, securing them in a rotated position.

In some embodiments, the arms are adapted to grasp the native chords so that the contact between arm and chord when deployed is near the radial periphery of the mitral valve annulus, for example within 5 mm, within 3 mm, or within 1 mm. Potentially, grasping at a further distance increases the moment arm exerting force to keep the prosthetic valve in position.

In some embodiments, the arms are adapted to grasp the native chords so that the region of contact between arm and chord is rotationally displaced from the place at which the chord joins the native valve leaflet, relative to an axis of rotation running perpendicularly through the mitral valve annulus. The relative angle of contact and juncture is, for example, at least 30 degrees, at least 45 degrees, at least 75 degrees, or at least 125 degrees. Potentially, a larger angular distance between the grasping juncture and the attachment juncture of the chord assists in pulling the leaflet across a larger surface area of the mitral valve annulus. Potentially, this provides a better seal for the valve.

It is a potential advantage for the ventricular part to have relatively small axial dimensions in the deployed configuration. A low profile when deployed inside a left ventricle helps avoid interferences with left ventricle functioning such as, example, partial occluding or causing turbulence in the vicinity of the aortic valve.

Connecting of the Two Frame Parts

In some embodiments, the atrial and ventricular parts of the prosthetic mitral valve frame are part of single unit and are physically connected, for example by their proximal ends. In some embodiments, connections between frame parts play multiple roles in fixation; and, in particular, help achieve fixation which takes advantage of structures of the heart including the native valve leaflets and/or chords.

Physical connection may be accomplished before and/or after deployment, for example, by suture and/or screw; or during deployment, for example by the use of elements which interlock as a result of deployment expansion.

In some embodiments, the distance between the peripheral (axial dimension) parts of the atrial and ventricular parts is predetermined to tightly seize the tissue (for example, leaflets and/or fibrous ring) in proximity of a native mitral by applying an axial force.

In some embodiments, the atrial part and the ventricular part of the prosthetic mitral valve are two physically separate components.

In some embodiments, the atrial part and the ventricular part are configured for mutual fixation in the deployed configurations. When each part is in a deployed configuration and the prosthetic mitral valve is properly deployed in a heart, the two parts can be fixed one to the other. In some embodiments, the configuration comprises the presence of eyelets, gaps, tabs, or other apertures and/or protrusions allowing mutual fixation with the help of an additional component of a type including, for example, suture thread, screw-and-nut, attachment rings, and/or ties.

In some embodiments, the atrial part and the ventricular part are mateable in the deployed configuration; that is to say, the atrial part includes one or more mating features configured to engage one or more mating features in the ventricular part. In some such embodiments, at least one of the atrial part and the ventricular part includes bending mating features, configured to receive a bend upon mating of the atrial part and the ventricular part. In some embodiments, the atrial part and the ventricular part engage one another with protrusions which restrict their relative movements.

Valve Mechanism

In some embodiments, the atrial part of the prosthetic mitral valve includes a valve mechanism, comprising at least one or more valve members which restrict blood flow in so that it is one-way through the valve in the direction from the heart left atrium to the heart left ventricle. The valve mechanism is functionally associated with the prosthetic mitral valve lumen so that the one or more valve members operate. In some embodiments, association is by, for example: suturing, gluing, dip molding, and/or crimping. In some embodiments, the ventricular part and/or the atrial part are provided with attachment structures adapted to participate in securing the valve mechanism.

The valve mechanism is suitable for functioning as a mitral valve. As such, it prevents flow of blood from the left ventricle to the left atrium through the prosthetic mitral valve lumen during ventricular systole but allows flow of blood from the left atrium to the left ventricle during diastole (for example, atrial systole).

In some embodiments, the prosthetic valve is a mechanical valve designed to be deployed by open heart surgery. Not necessarily limiting examples of mechanical values include a bileaflet-mechanism (St. Jude mechanism), a caged-ball mechanism (for example, Starr-Edwards mechanism), or a tilting-disc mechanism (for example, Bjork-Shiley mechanism). In some embodiments, for example, for minimally invasive deployment, the valve mechanism is a leaflet-valve mechanism known in the art including at least two leaflets, or least three leaflets, for example, Lotus™ or CoreValve™ mentioned above. In some embodiments, the valve mechanism is inside the prosthetic mitral valve lumen. In some embodiments, the valve mechanism is more particularly in the prosthetic mitral valve lumen of the connecting part such that, when deployed, the valve mechanism is located across the native mitral valve annulus and/or inside the left heart ventricle. Optionally, for example when deployed during an open-heart surgical procedure, the valve mechanism is secured to the valve frame after the frame is deployed.

Typically, artificial valve mechanisms, including leaflet-valve mechanisms are configured so as not to be subject to prolapse into a left atrium as can happen with native mitral valve leaflets. In some embodiments where a valve mechanism includes leaflets that are potentially subject to prolapse, the prosthetic mitral valve optionally includes a prolapse-preventing component, for example as described in U.S. Patent Publication No. 2002/0065554 and U.S. Patent Publication No. 2004/0138745 or as implemented in the Endovalve™ (Endovalve Inc., Princeton, New Jersey, USA). In some embodiments where a valve mechanism includes leaflets that are potentially subject to prolapse, the prosthetic mitral valve optionally includes a prolapse-preventing component that is substantially an artificial chord, for example as described in International Application Publication No. 2009/134701.

As noted above, pericardial trileaflet valve mechanism can be disposed inside lumen of prosthetic mitral valve. The valve mechanism is oriented in a direction so that when the atrial part is in a deployed configuration, the valve mechanism is functional. A functional valve mechanism allows the flow of blood from distal end to proximal end through the lumen, and blocks the retrograde flow of blood from proximal end to distal end through the lumen. In such a way, valve mechanism is functionally associated with lumen in a manner suitable for functioning as a mitral valve.

Dynamic Conformation

In some embodiments, the atrial part of the prosthetic mitral valve is configured, in the deployed configuration, to dynamically conform to the native mitral valve annulus and to the atrial walls in proximity of a native mitral valve of a heart in which deployed. Dynamic conformation provides potential advantages for maintaining fixation mechanisms which rely on connections to structures of the pumping heart.

In some embodiments, in an unconfined environment, the expanded part is slightly wider in the radial dimension than the native mitral valve annulus and/or atrial walls of the heart against which it presses when implanted. In some embodiments, the implanted atrial part radially expands to press against the atrial walls and the native mitral valve annulus.

As the heart beats, the shape and dimensions of the atrial walls and of the native mitral valve annulus change. In some embodiments, the atrial part dynamically conforms to these changes. Dynamic conformation potentially provides an advantage by permitting less impeded natural movement of the heart.

In some embodiments, the atrial part is provided with one or more elastic structures, such as springs, adapted to resiliently conform to the atrial walls and/or native mitral valve annulus. A potential advantage of such elastic structures is to allow pressing contact between the prosthetic valve and native structures, without impeding natural pumping motions of the heart.

Expandable Upper and Lower Parts

In some embodiments, the atrial and ventricular parts are outwardly radially expandable from a compact delivery configuration, for example, a crimped configuration, to the deployed configuration. In some embodiments, compact delivery allows minimally invasive entry to the heart. In some embodiments, expansion following compact delivery is functions as part of the implantation procedures which establish good device fixation.

In some embodiments, the atrial and ventricular parts have a larger outer radius in the deployed configuration than in the delivery configuration. A potential advantage of post-delivery expansion is compatibility with minimally-invasive deployment of the prosthetic mitral valve, for example, transapically, transfemorally, or transseptally. In some embodiments, delivery is with the use of a catheter deployment system such as a delivery catheter or similar.

In some such embodiments, the parts are expandable from the delivery configuration to the deployed configuration by application of a radially outwards force to an inner surface thereof, for example, with a catheter-mounted balloon.

In some embodiments, the parts are self-expanding from the delivery configuration to the deployed configuration.

Arms

In some embodiments, the arms are outwardly radially expandable from a compact delivery configuration to the deployed configuration. In some embodiments, arms are self-expanding from a delivery configuration to a deployed configuration. In some embodiments, deployment of arms after insertion into the vicinity of the native mitral heart valve allows the arms to insert in among the native chords of the heart. One potential advantage of this is to place the arms in a position to recruit chords for device fixation.

Optionally, the arms expand as part of the expanding ventricular part. Additionally or alternatively, the arms deploy at least in part independently of the expanding ventricular part; for example, by bending around the axis of the ventricular part.

In some embodiments, the arms protrude outward from a core region of the frame to regions where they encounter the chords of the native mitral valve. In some embodiments, they are shaped to grasp the native chords and/or leaflets of the mitral valve, for example by being shaped with hooks and/or protrusions.

According to some exemplary embodiments of the invention, the grasping shapes of the arms are engaged with the native chords and/or leaflets of the mitral valve by a rotation of the ventricular part. When the ventricular part is rotated, arms grasp the native chords and leaflets, causing at least portions of them to rotate around the mitral valve axis.

In some embodiments, in a deployed configuration, arms are connected to the proximal end of the ventricular part by spokes. In some embodiments, the arms and spokes are supported by an annular rim. Potentially, the use of a spoked rim allows arms to be shorter. A shorter arm is potentially reduced in susceptibility to bending forces. A less flexible arm potentially provides firmer control of chords that it grasps. Potentially, the rim may serve as a limit on the movement of captured chords along the length of the arm. In some embodiments, the base end of an arm is held close to the chords when the frame is deployed, for example by a rim with a sufficiently wide deployed diameter. Optionally, such an arm is just long enough to form a chord-catching protrusion; for example 1 mm long, 3 mm long, or 5 mm long.

In some embodiments of the invention, arms have a shape which assists in producing and/or maintaining tension on the chords. In some embodiments, arms are provided with one or more protruding members and/or other interruptions along their length. A potential advantage of a protruding member and/or other interruption along the length of an arm is to prevent a chord from slipping freely along the arm body to lower its tension as the arm is rotated against it during deployment, and/or after deployment. In some embodiments of the invention, arms are provided with a hook, which includes a terminal projection optionally reaching back in the central radial direction, the length of the back projection being, for example 1 mm, 3 mm, or 5 mm. In some embodiments, a surface of the hook is sloped away from a direction of rotation toward the open end of the hook, with a slope that is, for example, less than 60 degrees off the tangent of the circumference of the direction of rotation.

In some embodiments, the arm body itself is shaped so that tension in the chords is developed and/or maintained. A potential advantage of such a design is to increase the locking force on the support components of the prosthetic valve, for example, by transmitting rotational force to atrial components so that they are pushed into closer contact with the atrial wall.

According to the embodiment, arms have, for example, a T shape, an L shape, a curved shape, or a hook shape. One description common to these shapes is of having a body, which in some embodiments serves to "sweep" a region of chords, particularly as it rotates, and at least one cross-member, which in some embodiments serves to control the position of contact with the arm. It should be noted that in some embodiments, even the static extension of the arm into a region of chords is sufficient to encompass a wide angle of chords in the shadow of the arm. In some embodiments, the arm angles across, for example, 10 degrees, 30 degrees, 40 degrees, or 60 degrees from its base to its point of maximum extension, around an axis passing through the native mitral valve aperture.

Delivery Device for a Prosthetic Mitral Valve

According to an aspect of some embodiments of the invention, the prosthetic mitral valve is deployed using, for example, open-heart surgery or minimally-invasive surgery. In some embodiments, a catheter deployment system is used such as a flexible catheter that enters the left ventricle through the vasculature and the aorta. In some embodiments, the catheter deployment system comprises a catheter that enters the left atrium through the roof of the left atrium. In some embodiments, a catheter deployment system is used comprising a catheter that approaches the left atrium through the pulmonary vein, as in Endovalve™ by Micro Interventional Devices, Inc. (Bethlehem, PA, USA) and described in U.S. Pat. Nos. 7,621,948; 7,753,949; 8,070,802 B2; and U.S. patent application Ser. No. 12/582,986.

In some embodiments, two part construction of the frame of the prosthetic mitral valve is reflected in the catheter deployment system; for example, by the provision of separate controls, deployment structures, and/or restraint structures for each part. Two part construction is potentially an advantage during deployment; for example, allowing in-heart assembly and deployment steps which promote closer association with and/or fixation to the supporting tissue of the heart, as described herein.

In some embodiments, a catheter deployment system is used comprising a transapical catheter that enters the left ventricle through the cardiac apex.

According to an aspect of some embodiments of the invention, there is provided a catheter deployment system for transapically deploying a prosthetic mitral valve contained therein, comprising some or all of the following:

a. a substantially tubular delivery housing including a delivery lumen having an opening at a distal end thereof;
b. inside the delivery lumen, a prosthetic mitral valve including at least an atrial part and a ventricular part, in a compact—for example, crimped—delivery configuration, the prosthetic mitral valve being outwardly radially expandable subsequent to release from the delivery housing to a deployed configuration;
c. a ventricular-part release mechanism allowing release of the ventricular part through the distal end of the delivery housing;
d. a rotation component functionally associated with the ventricular part, the rotation component configured to induce rotation to at least a part of the ventricular part when actuated;
e. an atrial-part release mechanism allowing release of the atrial part through the distal end of the delivery housing; and
f. a delivery device release mechanism allowing detachment of the delivery device from the delivered mitral valve.

In some embodiments, the atrial part includes a valve mechanism functionally associated with the prosthetic mitral valve lumen, the valve mechanism being suitable for functioning as a mitral valve.

Balloon-Expandable Atrial Part

In some embodiments, the catheter deployment system comprises an upper-part expansion assembly, configured to apply a radially outwards force to an inner surface of the atrial part subsequent to release from the delivery housing. The expansion assembly radially expands the atrial part from the delivery configuration to the deployed configuration. In some embodiments, the upper-part expansion assembly includes a catheter-mounted balloon catheter.

In some embodiments, the atrial part and the upper-part expansion assembly are together configured so that in the deployed configuration, the atrial part conforms to an atrial contour near the native mitral valve. In some embodiments, in which the upper-part expansion assembly is a catheter-mounted balloon, the balloon has an inflated shape similar to the atrial contour near the native mitral valve. In some embodiments, the balloon is a compliant balloon that adopts the shape of the atrial contour near the native mitral valve when inflated.

Self-Expanding Atrial Part

In some embodiments, the upper part is self-expanding from the delivery configuration to the deployed configuration subsequent to release from the delivery housing. In some such embodiments, the upper part is configured so that in the deployed configuration, the atrial part dynamically conforms to a mitral valve annulus and to the atrial walls in proximity of the mitral valve of the heart in which it is deployed.

Balloon-Expandable Ventricular Part

In some embodiments, the catheter deployment system comprises a lower-part expansion assembly, configured to apply a radially outwards force to an inner surface of the lower part subsequent to release from the delivery housing. The lower-part expansion assembly radially expands the ventricular part from the delivery configuration to the deployed configuration. In some embodiments, the lower-part expansion assembly includes a catheter-mounted balloon catheter.

Self-Expanding Ventricular Part

In some embodiments, the lower part is self-expanding from the delivery configuration to the deployed configuration subsequent to release from the delivery housing.

Self-Expanding Arms

In some embodiments, the grasping part of the ventricular part is self-expanding from the delivery configuration to the deployed configuration subsequent to release from the delivery housing.

Rotation Component

As noted above, in some embodiments, at least a part of the prosthetic mitral valve is associated with a rotation component, configured to induce rotation to at least one arm of the ventricular part when actuated.

In some embodiments, the rotation component includes a sensor measuring the torque force being applied to chords and leaflets. In some embodiments, the rotation component includes a stopper mechanism, impeding applying torque forces above a predetermined value to chords and leaflets.

In some embodiments, the rotation component imparts a predetermined angle of rotation as a step in prosthetic mitral valve deployment.

Fixation Component

In some embodiments, a fixation component is functionally associated with at least the atrial part of the prosthetic mitral valve, the fixation component being configured to regulate the distance between the peripheral (axial dimension) parts of the atrial and the ventricular parts after their deployment.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Valve Embodiments

Parts of an embodiment of a prosthetic mitral valve are schematically depicted in the following figures.

Figure 29A:
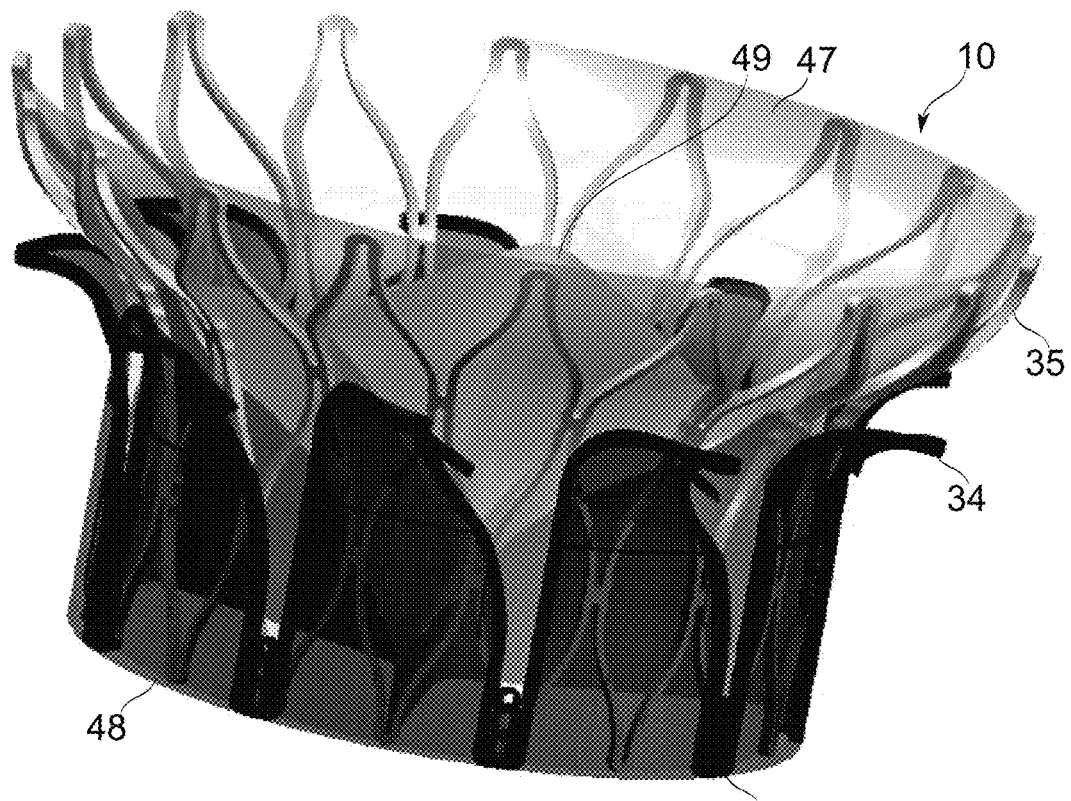
FIGS. 29A-29B are schematic perspective view of prosthetic mitral valves, in accordance with exemplary embodiments of the invention.
Figure 29B:
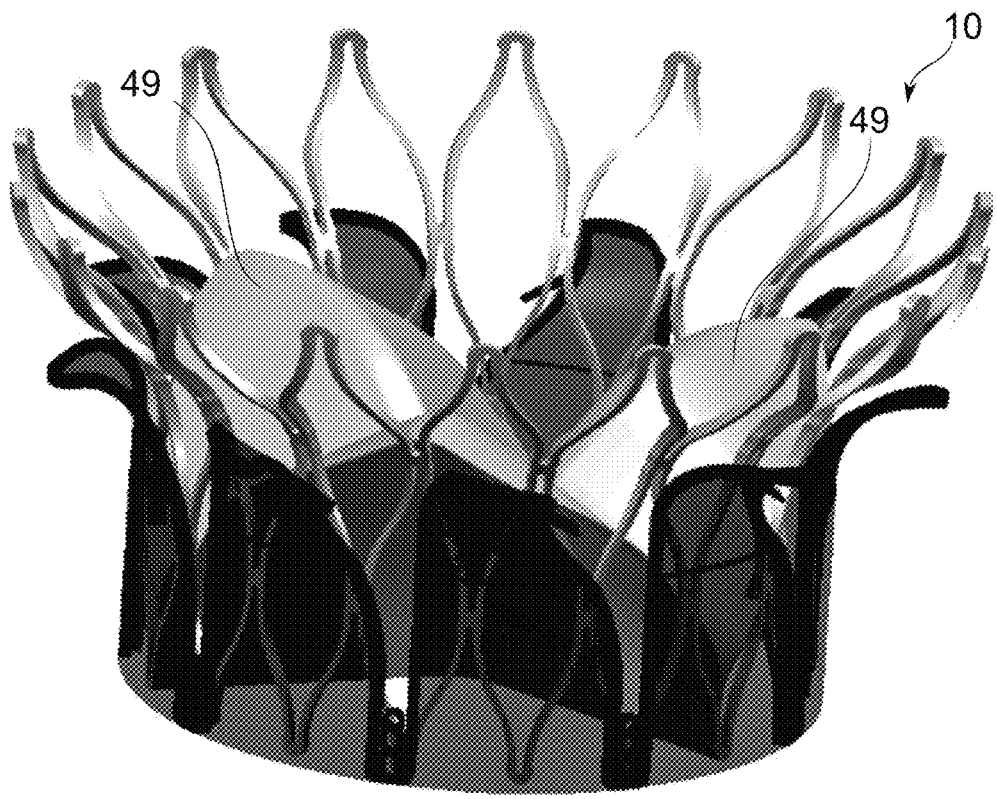

Reference is now made to FIGS. 29A-B, which schematically depict a prosthetic mitral valve 10, according to an exemplary embodiment of the invention. These figures overview the main components of prosthetic mitral valve embodiments, as related to herein.

In some embodiments of the invention, prosthetic mitral valve 10 comprises frame parts including ventricular part 32, and an atrial part 35. In some embodiments, the ventricular part 32 surrounds the proximal (lower) end of the atrial part 35. In some exemplary embodiments of the invention, these parts 32, 35 provide the superstructure which anchors the prosthetic mitral valve 10 within the heart; for example, according to principles and details described herein.

In some embodiments of the invention, ventricular part 32 comprises one or more arms 34 which are sized, shaped, and positioned to engage with the chords of the native mitral valve when deployed. In some embodiments, chord engagement by the arms 34 is encouraged by rotational movement of at least the ventricular part 32 during deployment. Potentially, at least a portion of the chords which the arms 34 engage with are captured and recruited into fixation of the prosthetic mitral valve, for example, by pulling the native valve leaflets into closer association with the prosthetic valve.

Shown held within the lumen of the atrial and/or ventricular parts is the prosthetic valve mechanism 49, comprising at least the valve member that restricts blood flow from the ventricle to the atrium. The valve member is, for example, a plurality of valve leaflets. In some embodiments of the invention, valve mechanism 49 replaces the valve function of the native atrial valve leaflets.

In some embodiments of the invention, ventricular part 32 is provided with a ventricular part skirt 48. In some embodiments, ventricular part skirt 48 is made of an appropriate biocompatible material, for example PET, a fixing bovine or porcine pericardium, and/or other biocompatible polymer. In some embodiments, a polymer such as PET is combined with a fixing bovine or porcine pericardium. In some embodiments, the skirt is attached to the ventricular part by suturing. In some embodiments, a skirt is attached by polymer dipping and/or spattering on the frame. In some embodiments, the thickness of polymer sections of the skirt is, for example, in the range of 0.01 mm-0.03 mm, or thicker. In some embodiments, the thickness of pericardium-derived sections of the skirt is, for example, in the range of 0.2 mm-035 mm, or a range including thinner or thicker values.

In some embodiments, the ventricular part skirt 48 expands along with the ventricular part during deployment. Potentially, the ventricular part skirt 48 provides an advantage in use by acting as a protective barrier between tissue and the metal of the ventricular part. Potentially, the ventricular part skirt 48 has advantages listed in connection with the atrial skirt 47, below.

In some embodiments of the invention, atrial part 35 is provided with an atrial part skirt 47 (skirt 47 is suppressed in FIG. 29B in so that valve mechanism 49 may be more clearly seen). In some embodiments, atrial part skirt 47 is made of an appropriate biocompatible material, for example, from among those listed for the ventricular part skirt 48. In some embodiments, atrial part skirt 47 is constructed and/or attached, for example, as described for ventricular skirt 48.

In some embodiments, the atrial part skirt 47 expands along with the atrial part during deployment. Potentially, the atrial part skirt 47 provides an advantage by acting as a protective barrier between tissue and the metal of the atrial part. Potentially, the atrial part skirt 47 provides additional friction, which assists with native valve leaflet capture and/or preservation of capture. Potentially, and particularly in embodiments in which it is constructed of pericardium, the atrial part skirt 47 provides a substrate promoting ingrowth of, for example, the native leaflets of the mitral valve, promoting a stronger attachment. Potentially, the atrial skirt 47 provides an advantage for extra sealing against the retrograde flow of blood in the region of the native mitral valve annulus.

Valve Embodiment with Ventricle Part Band

Reference is now made to FIG. 1, which schematically depicts an exemplary prosthetic mitral valve 10 in unexpanded and deployed configurations positioned inside the native mitral valve annulus 20, according to an exemplary embodiment of the invention.

Atrial part 35A is shown still unexpanded, in the configuration it has when it is inserted to the heart. Ventricle part 32 is shown already expanded. Atrial part 35 is shown in its expanded configuration, as assumed after full deployment of prosthetic mitral valve 10.

In some embodiments, atrial part 35 and ventricular part 32 are physically connected via a connecting part 54. In some embodiments, atrial and ventricular parts are one part. Arms 34 grasp native chords 22 and/or leaflets of native mitral valve 24 when rotated. In some embodiments, the rotation pulls the leaflets into a position that closes the gaps between the native mitral valve and prosthesis 10. In an exemplary embodiment of the invention, mitral valve annulus 20 is seized between atrial part 35 and ventricular part 32 of prosthetic mitral valve.

Figure 2A:
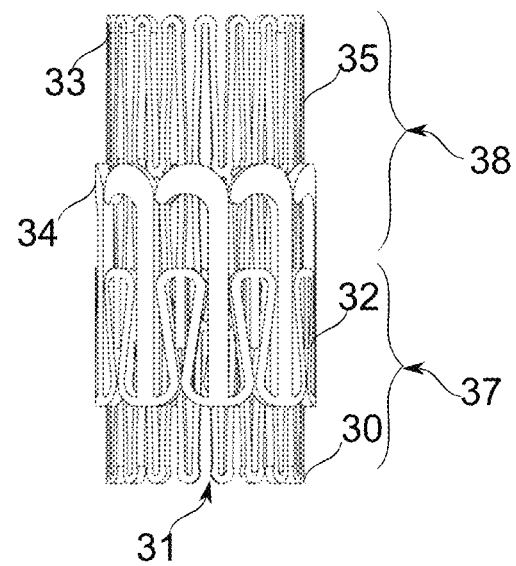
FIGS. 2A-2B schematically depict prosthetic mitral valves, in accordance with an exemplary embodiment of the invention.
Figure 2B:
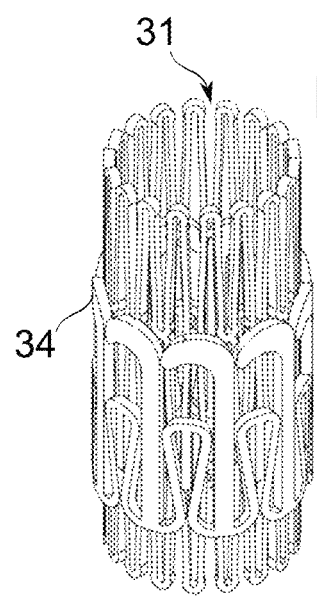
Figure 3A:
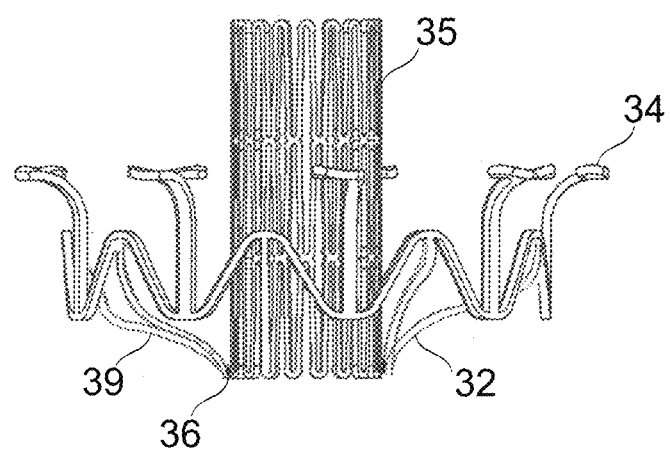
FIGS. 3A-3D schematically depict prosthetic mitral valves, in accordance with an exemplary embodiment of the invention.
Figure 3B:
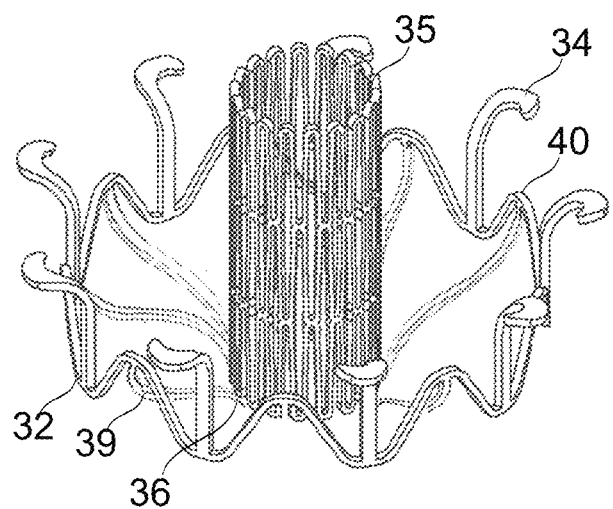
Figure 3C:
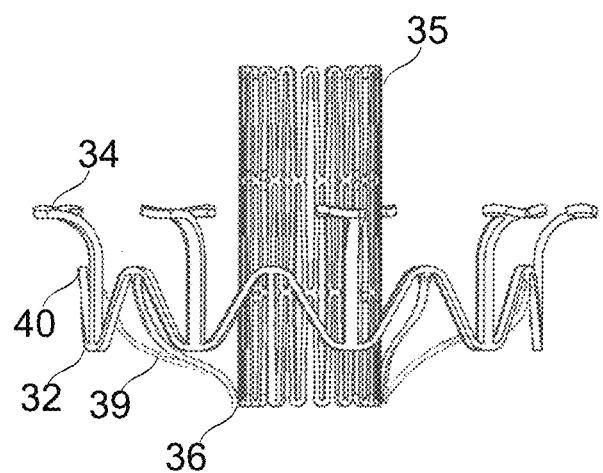
Figure 3D:
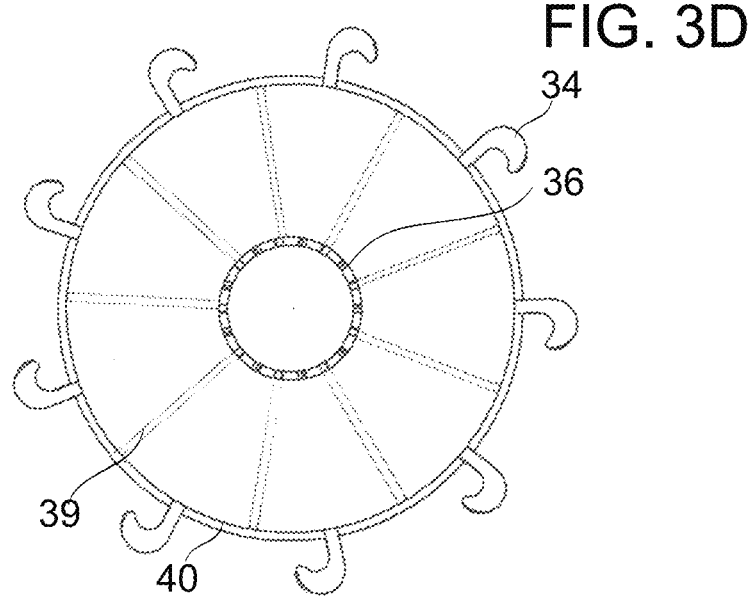

Reference is now made to FIGS. 2A-2B, which depict two different views of an exemplary atrial part 35 and a ventricular part 32 including arms 34, together comprised in a prosthetic mitral valve frame in a compact delivery configuration, according to an exemplary embodiment of the invention.

In some embodiments of the invention, parts 35, 34 and/or 32 are fashioned of self-expanding nitinol, biased to a larger outer radius deployed configuration. Optionally, parts 35, 32, and/or 34 are laser-cut from a tube of nitinol. Optionally, the tube has an outer diameter with an outer diameter of 8 mm, 10 mm, 12 mm, or another outer diameter larger or smaller, or any diameter in between. Optionally, the tube has a wall thickness of 0.25 mm, 0.35 mm, 0.5 mm, 0.8 mm, or another thickness larger or smaller, or any thickness in between.

Parts 35 and 32 are depicted in a compact delivery configuration, for example, as if held inside a delivery lumen of a delivery housing of a catheter deployment system such as a valve-deployment catheter. Optionally, parts 35 and 32 are in a crimped configuration. In some embodiments, the unit comprising the delivery configuration of parts 35 and 32 has a total length which is 23 mm, 25 mm, 28 mm, 30 mm, 32 mm, or another longer or shorter length, or any length in between. In some embodiments, the delivery configuration of parts 35 and 32 packages them separately, and they are brought together during deployment. The atrial part 35 defines a prosthetic mitral valve lumen 31 between a proximal end 30 and a distal end 33.

Optionally, one or more arms 34 are curved with the interior facing in the direction of rotation during deployment of the valve in the native mitral valve annulus. Optionally, rotation of the arms 34 recruits the chords into the fixation of the valve. Optionally chord recruitment pulls the native valve leaflets into a sealing relationship with the prosthetic valve. Optionally, the rotation is imparted, for example, by the rotation device as used from outside the body when using the apex approach.

Atrial part 35 is divided into two portions between proximal end 30 and distal end 33: a proximal portion 37 and a distal portion 38. The atrial part 35 is comprised of struts.

Reference is now made to FIGS. 3A-3D, which depict four different views of an exemplary prosthetic mitral valve frame (which may correspond, for example, to the compact frame shown in FIGS. 2A-2B) with its ventricular part 32 in a deployed configuration, according to an exemplary embodiment of the invention. The ventricular part 32 is physically connected to the atrial part 35 by its proximal end 36. In a deployed configuration, arms 34 expand radially from the proximal part of the ventricular part to physically engage with native chords and leaflets. Arms 34 are connected to the proximal end 36 by spokes 39, and are also supported by an annular rim 40. In some embodiments, the partially deployed configuration of FIGS. 3A-3D is the configuration in which chord-capturing rotation is applied to engage the arms 34 of the frame with the native mitral valve chords.

Figure 4A:
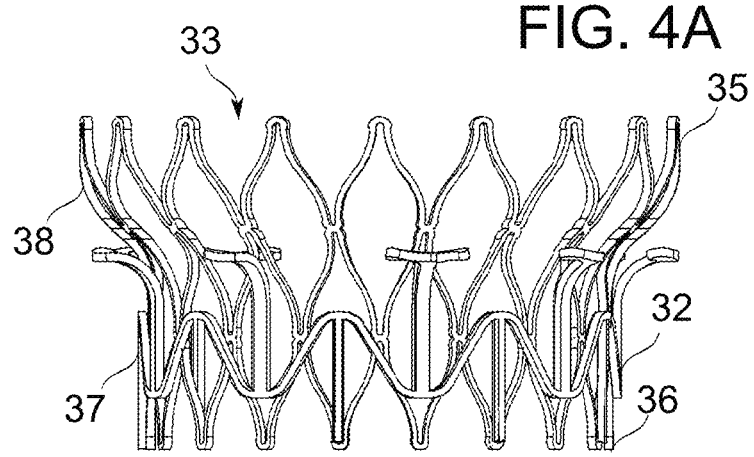
FIGS. 4A-4B schematically depict prosthetic mitral valves, in accordance with an exemplary embodiment of the invention.
Figure 4B:
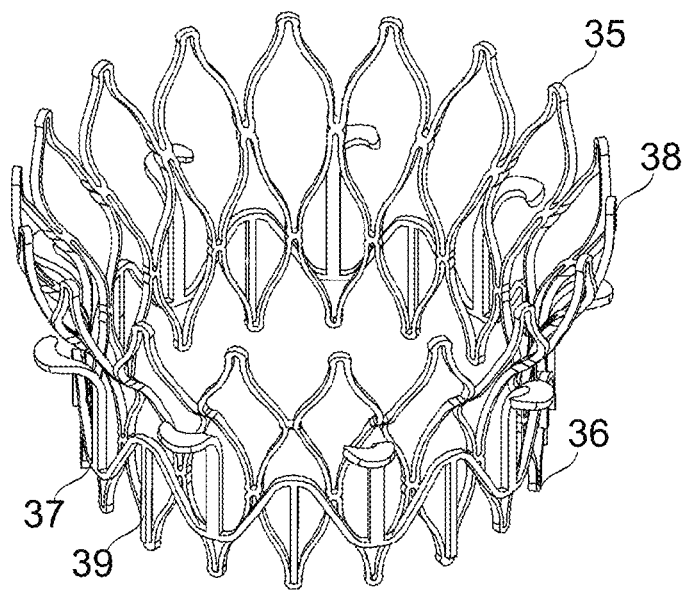

Reference is now made to FIGS. 4A-4B, which depict two views of an exemplary prosthetic mitral valve with its atrial part 35 and ventricular part 32 unconstrained and adopting a deployed configuration, according to an exemplary embodiment of the invention.

In some embodiments corresponding to the deployed configuration depicted in FIGS. 4A-4B, atrial part 35 adopts the shape of an inverted shoulder. In some embodiments, the wide end of the shoulder has an outer diameter at distal end 33 which is 38 mm, 40 mm, 42 mm, 44 mm, any diameter in between, or a greater or lesser diameter. In some embodiments, the narrow end has an outer diameter at proximal end 30 which is 23 mm, 25 mm, 27 mm, 29 mm, 31 mm, any diameter in between, or a greater or lesser diameter. In some embodiments, the atrial part has total length, which is 24 mm, 26 mm, 28 mm, 30 mm, 32 mm, any length in between, or a greater or lesser length.

In some embodiments, the size and shape of atrial part 35 are adapted for deployment inside a left atrium of a heart wherein proximal portion 37 passes into a mitral valve annulus, while the outer surface of distal portion 38, larger in diameter than the mitral valve annulus, rests against the inner walls of the left atrium in proximity of the mitral valve annulus.

In some embodiments, deployment of atrial part 35 occurs after a rotation of at least a portion of the mitral valve frame which recruits rotational tension by interactions with the mitral valve chords. In some embodiments, deployment of atrial part presses against and/or penetrates portions of the native heart tissue and/or ventricular part 32, locking the rotational tension into place.

Valve Embodiment with Independent Arm Mounts

Reference is now made to FIGS. 13A-13F, which schematically illustrate an exemplary embodiment of a prosthetic valve 100, according to an exemplary embodiment of the invention. For clarity, the prosthetic mitral valve leaflets (and other blood flow control elements) have been omitted from the figures.

Figure 13A:
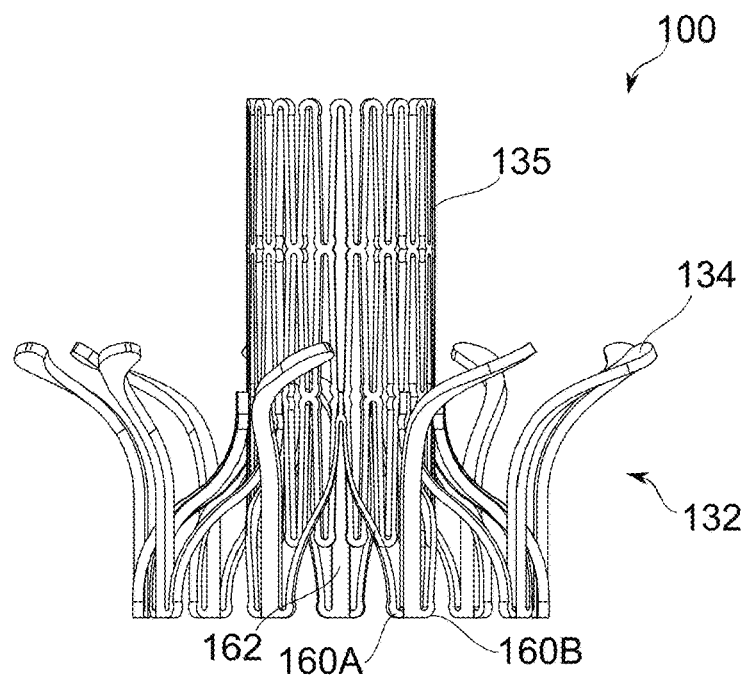
FIGS. 13A-13F are schematics of some additional embodiments of the prosthetic mitral valve, in accordance with an exemplary embodiment of the invention.

FIG. 13A depicts a side view of valve 100 in which ventricular part 132 is in the deployed (or expanded) state and atrial part 135 is in the compressed state.

Figure 13B:
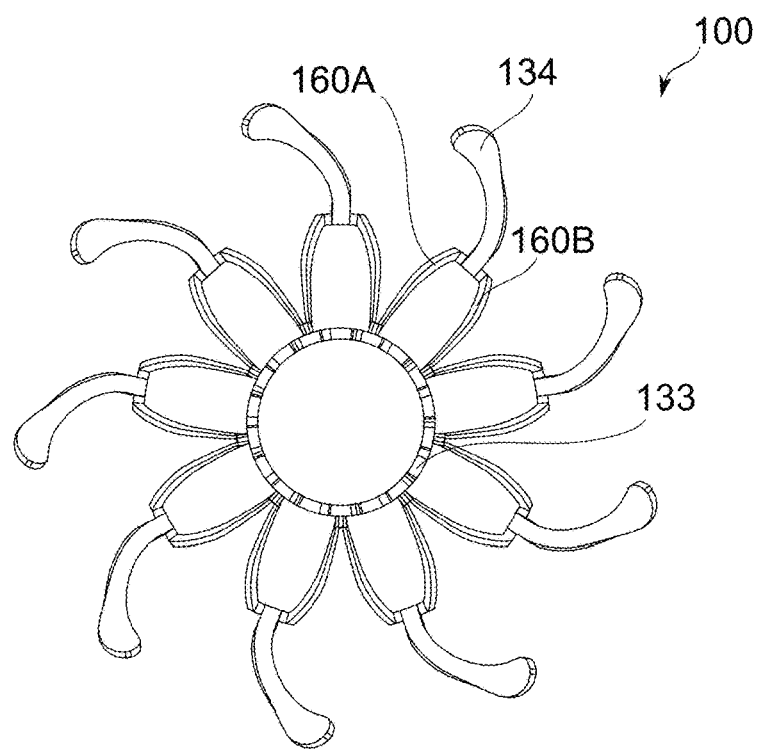

FIG. 13B depicts a top view of valve 100 of FIG. 13A.

Figure 13C:
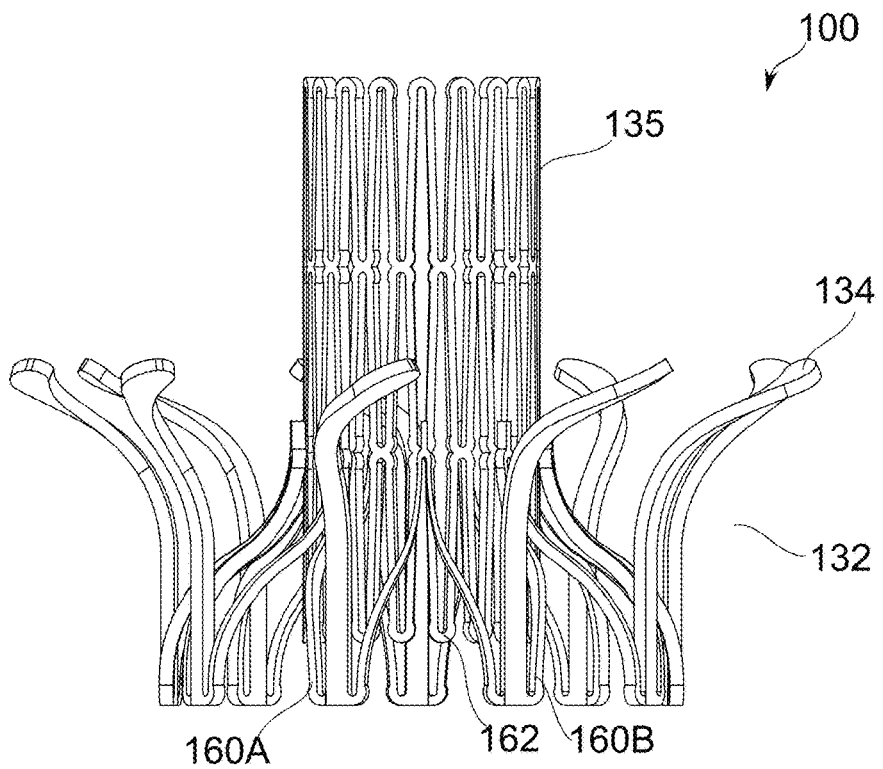

FIG. 13C depicts a magnified view of FIG. 13A.

Figure 13D:
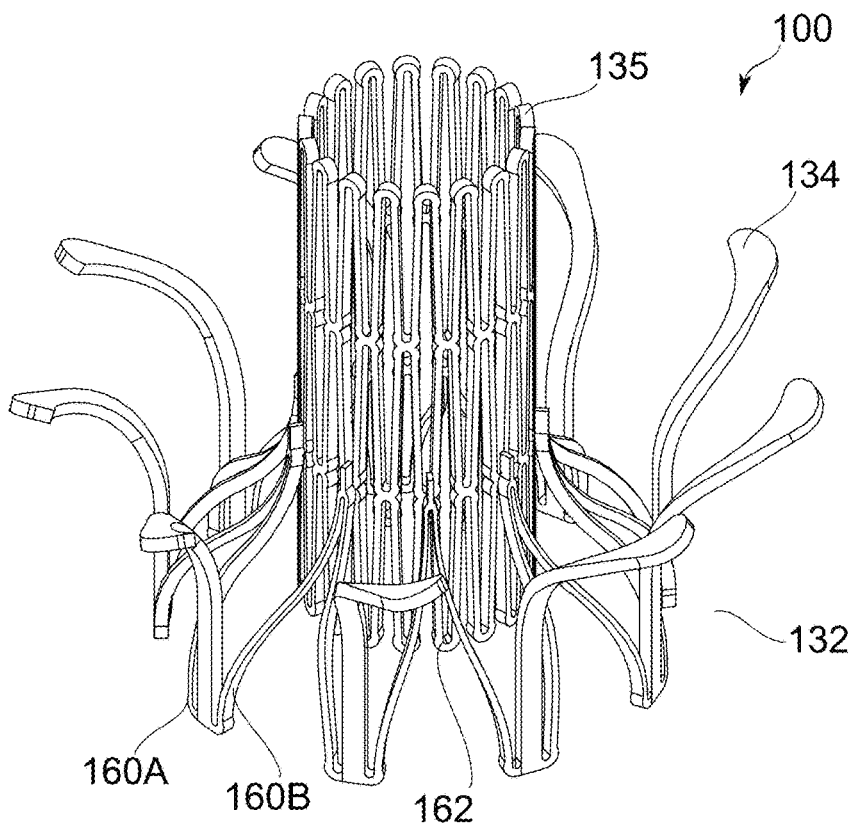

FIG. 13D depicts an isometric view of valve 100 of FIG. 13A.

Figure 13E:
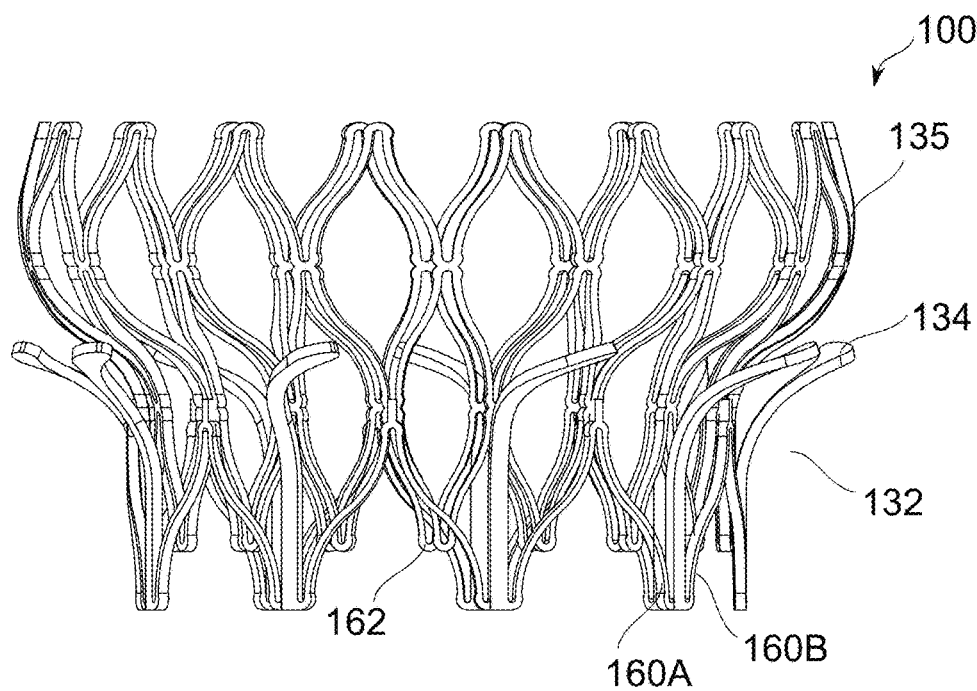

FIG. 13E depicts a side view of valve 100 in the fully deployed state. Both atrial part 135 and ventricular part 132 are fully expanded.

Figure 13F:
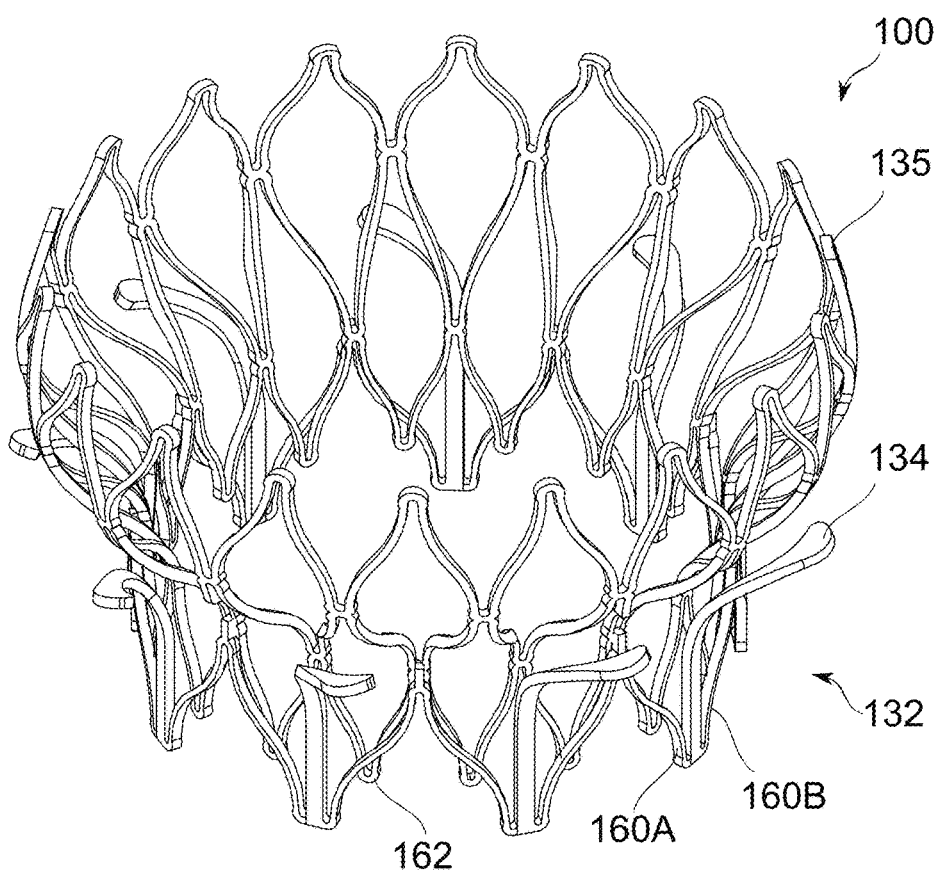

FIG. 13F depicts an isometric view of valve 100 expanded as in FIG. 13E.

The depictions of FIGS. 13A-13F illustrate alternate embodiments of certain mechanisms of operation disclosed herein. Alternative embodiments include changes to the relative attachment positions of the arms 134 to the structure of the overall valve 100. In some embodiments of the invention, arms 134 are attached individually on separate struts 160A, 160B, instead of being basally mounted to a common ring structure. In some embodiments, independent mounting of the arms 134 allows individual determination of deployment characteristics such as their extending distance and extension angle.

In some embodiments of the invention, one or more arms 134 are curved with the inner part of the curve facing the direction of rotation which is applied to recruit the chords of the native mitral valve. Rotation is imparted, for example, by the rotation device as used from outside the body when using the apex approach.

In an exemplary embodiment, arms 134 are attached to atrial part 135 without being attached to one another, for example, other than at atrial part 135. Optionally, arms 134 are attached to atrial part 135 by one or more struts (for example, two struts) 160A, 160B. Optionally, struts 160A, 160B are integrated with struts forming atrial part 135, or are attached to struts of atrial part 135, for example, by welding, crimping, or other methods. Optionally or additionally, struts 160A, 160B are attached to atrial part 135 away from the proximal end 162, for example, at least 1 mm, 3 mm, 5 mm, 7 mm, 10 mm, or other smaller, intermediate or larger distances away.

In some embodiments, each arm 134 radially expands to a potentially different diameter and/or potentially different axial height. In some embodiments, differentially extending arms 134 are provided. Potentially, differential extension permits adjustment to anatomical variations of the mitral valve and/or to diseased mitral valves (for example, calcifications, loose chords, and/or rigid chords). Potentially, attachment of the arms to struts 160A, 160B which project distally from the proximal edge of the ventricular part 132 helps to better grab hold of the leaflets between the atrial and ventricular parts, as the leaflet is anchored by pressure from arms 134, brought into close association with it by elevation from struts 160A and 160B. In some embodiments, an arm itself is only as long as needed to catch at a chord, for example, 1 mm, 3 mm, or 5 mm. This is possible, for example, if one or more supporting struts present the arm far enough within the region of the chords that the arm is likely to encounter chords even near its attached base.

Figure 17:
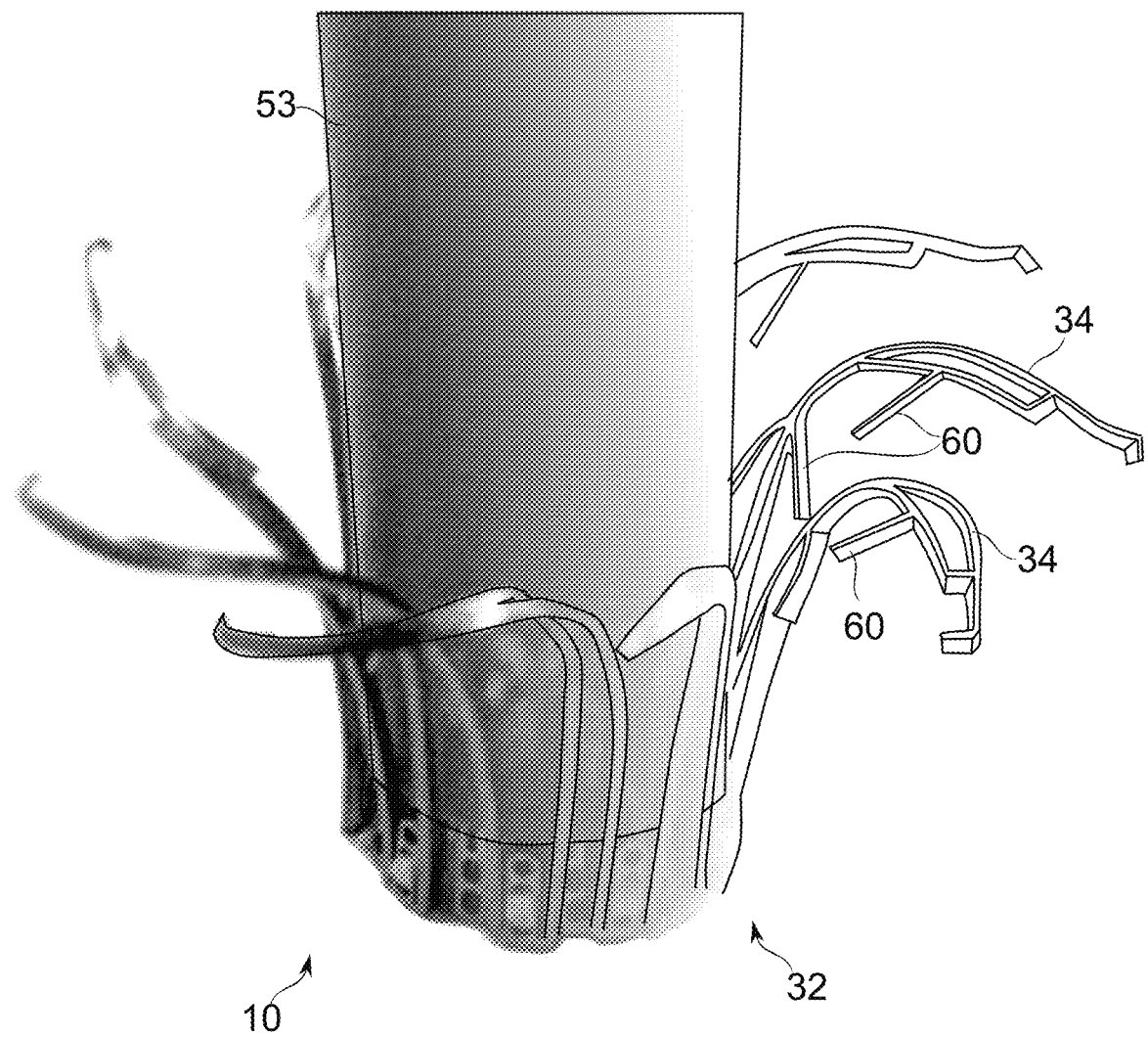
FIG. 17 is a photograph/schematic of a deployed ventricular part of a prosthetic mitral valve, in accordance with an exemplary embodiment of the invention.

Reference is now made to FIG. 17, which is a photograph supplemented by schematic lines of an exemplary deployed ventricular part 32 of a prosthetic mitral valve 10, according to an exemplary embodiment of the invention.

(It should be noted that in the photograph, atrial part retaining tube 53 maintains hidden atrial part in its crimped position, while ventricular part 32 is expanded.)

In some embodiments of the invention, the arms 34 of ventricular part 32 comprise one or more side projections 60 protruding from the main body of the arm along its sides. In some embodiments of the invention, the projections are members have a length from their free end to their attached end of 2 mm, 3 mm, 4 mm, or any length in between, or a longer or shorter length. In some embodiments, the arms have a width which ranges, for example, between 2 mm and 6 mm. In some embodiments, projections are members which project toward the base of the arm. Potentially, the side projections 60 comprise an advantage for grasping the native chords 22 of the native mitral valve 24, by preventing them from sliding along the capturing arm 34 to a position of lowered stretching. Potentially, backward-projecting side projections 60 comprise an advantage by pushing chords aside as arm 34 extends into a region of chords, and blocking the escape of chords when there is relative movement in another direction. More fully stretched chords provide a potential advantage by exerting a stronger restraining force on the sealing of the native valve leaflets.

Figure 18A:
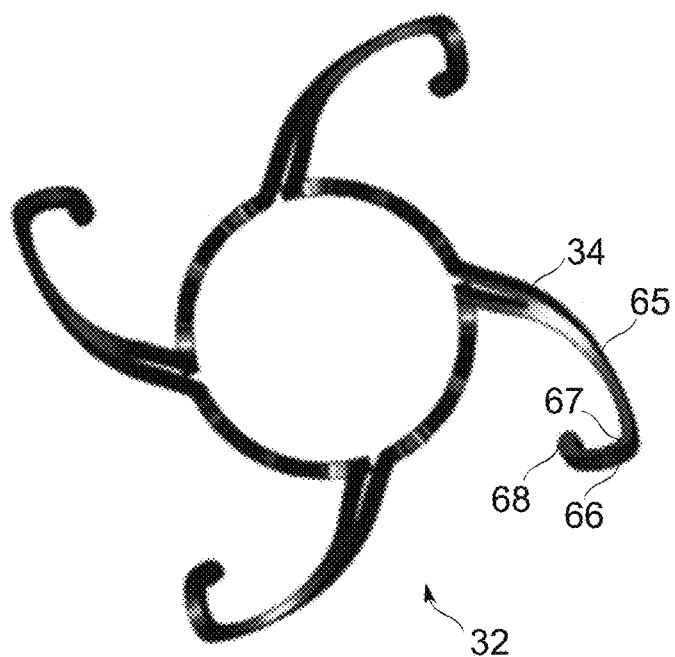
FIGS. 18A-18B are schematic illustrations of an exemplary deployed ventricular part of a prosthetic mitral valve, in accordance with an exemplary embodiment of the invention.
Figure 18B:
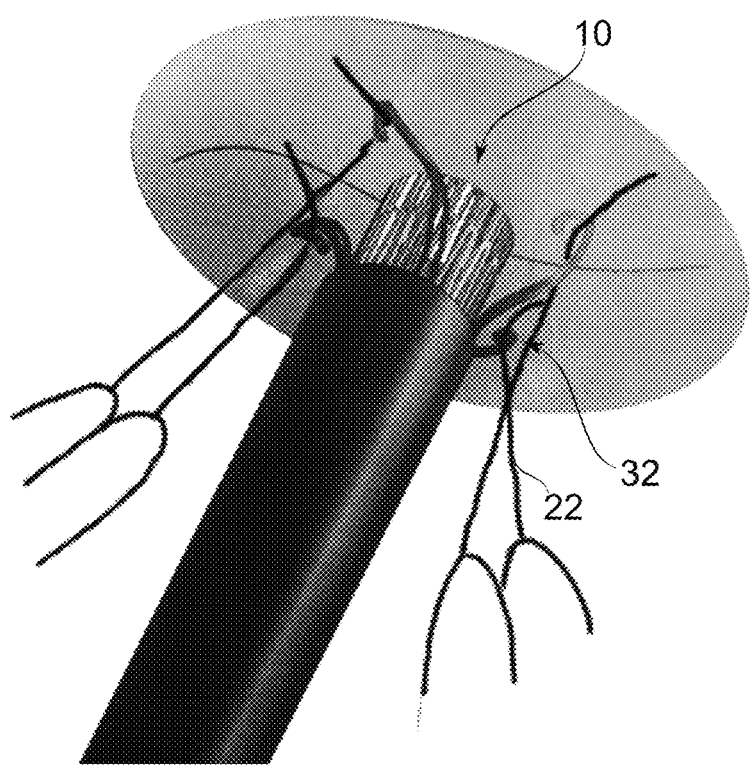

Reference is now made to FIGS. 18A-18B, which are schematic illustrations of an exemplary deployed ventricular part 32 of a prosthetic mitral valve 10, according to an exemplary embodiment of the invention.

In some embodiments, the arms 34 of the ventricular part 32 are adapted to grasp the native chords 22 so that arms and chords contact near the radial periphery of the mitral valve annulus, for example within 5 mm, within 3 mm, or within 1 mm. During deployment, rotation of ventricular part 32 is in the clockwise direction as seen from above. Chord capture is aided by a combination of design factors:

a. In some embodiments, arm 34 extends far enough to approach the radial periphery of the annulus.

b. In some embodiments, arm 34 is provided with internal curl 67, including a hook 68. Potentially, this provides an advantage by allowing chords that have been guided to enter the interior area fewer directions of escape. Potentially, the curl provides a degree of lateral strength to the structure of the arm, so that it resists bending in the opposite direction when it encounters the chords.

It should be noted that in some deployments of the invention, the heart, and therefore the chords, continue to move. It is potentially beneficial to rotate the arms without delay once trapping begins, so that chords are tightened as they are caught, and have diminished opportunity to work free again.

Two-Component Valve Fixation Embodiment with Mutual Attachment Elements

Figure 5A:
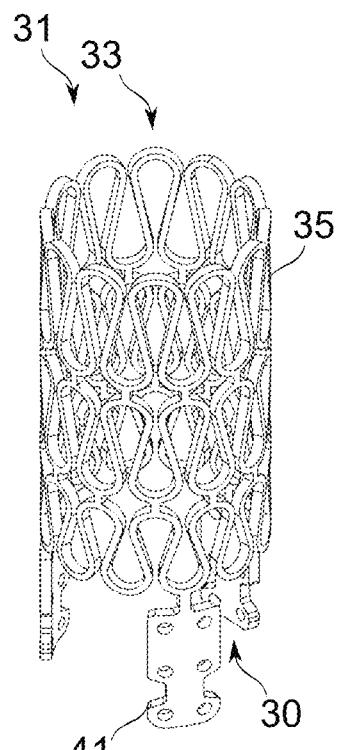
FIGS. 5A-5B schematically depict prosthetic mitral valves, in accordance with an exemplary embodiment of the invention.
Figure 5B:
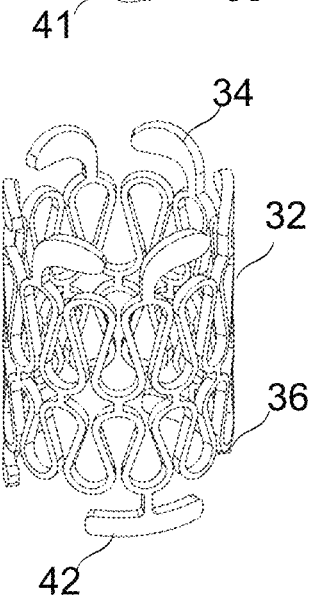

Reference is now made to FIGS. 5A-5B, which depict two views of a prosthetic mitral valve frame in a compact delivery configuration, wherein the atrial part 35 and the ventricular part 32 of the prosthetic mitral valve are two physically separate components, according to an exemplary embodiment of the invention. In some embodiments of the invention, separated valve frame parts allows, for example, independent rotation of the ventricular part 32 when recruiting the native mitral valve chords. Potentially, it is an advantage if atrial part 35 and/or components it contains, such as a valve mechanism, remain stationary and/or undeployed during chord recruitment. For example, having atrial part 35 detached and undeployed during rotation of ventricular part 32 potentially reduces the possibility of interfering contacts with other portions of the heart. In some embodiments, attachment of ventricular part 32 and atrial part 35 is performed during operations to deploy the prosthetic mitral valve, for example, through the use of attachment mechanisms described herein.

Optionally, parts 35, 32, and/or 34 are laser-cut from a tube of nitinol. Optionally, the tube has an outer diameter with an outer diameter of 8 mm, 10 mm, 12 mm, or another outer diameter larger or smaller, or any diameter in between. Optionally, the tube has a wall thickness of 0.25 mm, 0.35 mm, 0.5 mm, 1 mm, or another thickness larger or smaller, or any thickness in between. Parts 35 and 32 are depicted in a compact delivery configuration, for example, as if held inside a delivery lumen of a delivery housing of a catheter deployment system such as a valve-deployment catheter. In some embodiments, the unit comprising the delivery configuration of parts 35 and 32 has a total length which is 23 mm, 25 mm, 28 mm, 30 mm, 32 mm, or another longer or shorter length, or any length in between. The atrial part 35 defines a prosthetic mitral valve lumen 31 between a proximal end 30 and a distal end 33.

In some embodiments, the atrial part 35 has a length, for example, of 34 mm, 36 mm, 38 mm, 40 mm, 42 mm, any length in between, or a longer or shorter length. In some embodiments, the ventricular part 32 has a length, for example, of 10 mm, 11 mm, 12 mm, 14 mm, any length in between, or a longer or shorter length.

In some embodiments of the invention, attachment of the ventricular part 32 and the atrial part 35 is achieved by interlocking structures which are brought into contact and/or undergo a conformational change during prosthetic mitral valve deployment.

In some embodiments of the invention, three perforated tabs 41 extend from the proximal end of atrial part 35. These tabs have a length of 5 mm, 7 mm, 9 mm, any length in between, or a longer or shorter length. Amongst other potential functions, tabs 41 serve in some embodiments for mutual fixation of atrial part 35 and ventricular part 32. Lockers 42 extend from the proximal end of ventricular part 32. Amongst other potential functions, lockers 42 serve in some embodiments for mutual fixation of atrial part 35 and ventricular part 32 by interacting with tabs 41. Optionally, lockers 42 are manufactured with a shape memory, and undergo a conformational change during deployment and/or manufacture which wraps them around a corresponding tab structure 41.

Figure 25A:
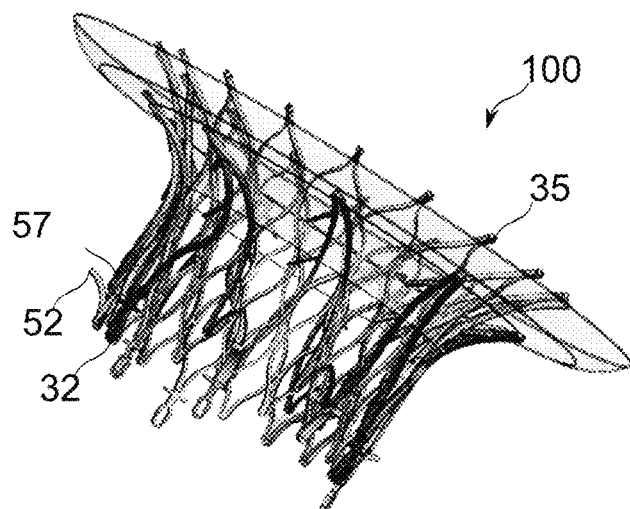
FIGS. 25A-25B are schematic perspective views of an atrial part inserted into a ventricular part, with the atrial part prevented from rising distally out of the ventricular part by a spur member, in accordance with an exemplary embodiment of the invention.
Figure 25B:
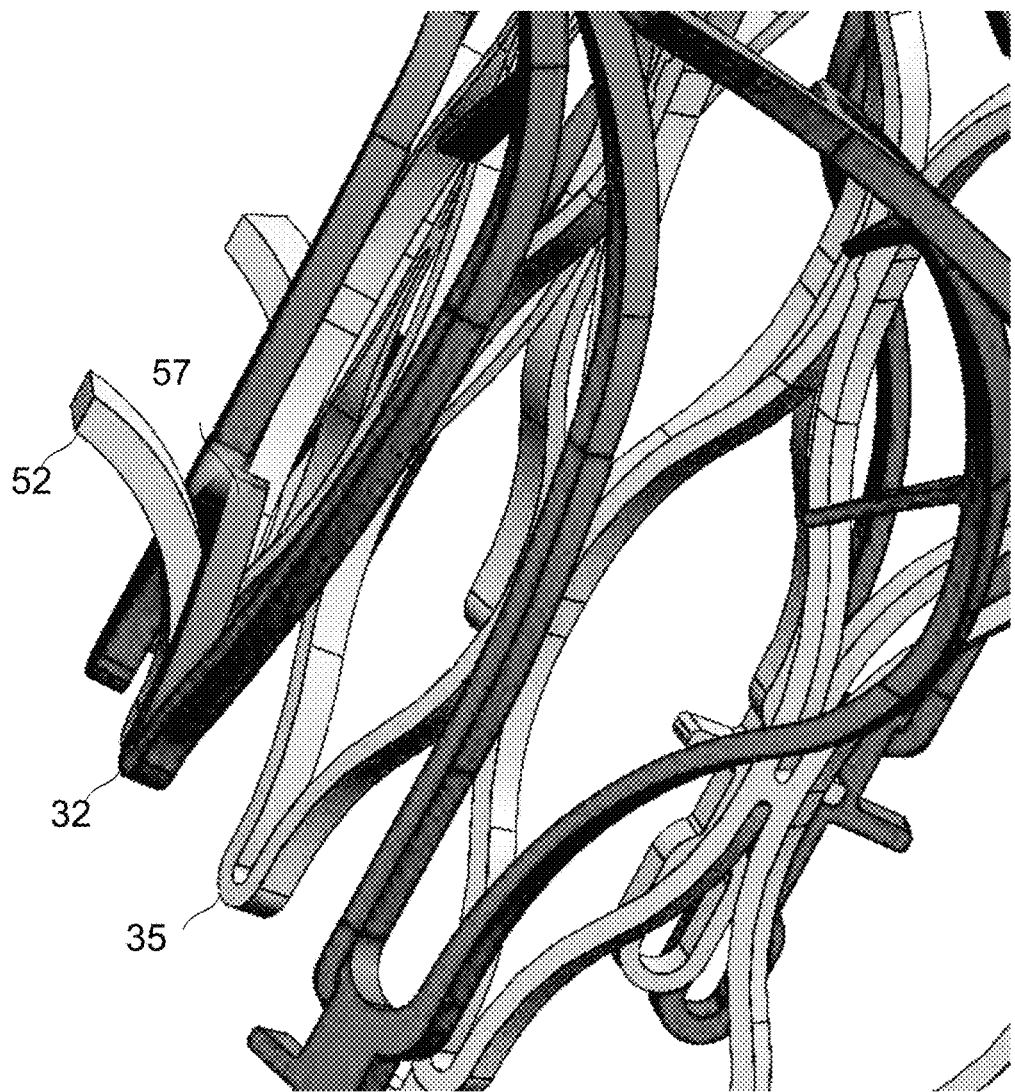

Reference is now made to FIGS. 25A-25B, which show schematic perspective views of an atrial part 35 inserted into a ventricular part 32, with the atrial part 35 prevented from moving distally out of the ventricular part 32 by a spur member 52, according to an exemplary embodiment of the invention. FIG. 25B shows an expanded view of the lower left corner of FIG. 25A.

In some embodiments of the invention, spur member 52 protrudes from atrial part 35 of prosthetic mitral valve 100. In some embodiments, spur member 52 extends in the direction of ventricular part 32 and into and/or beyond the space defined by the members of the ventricular part 32 frame. The interpenetration prevents atrial part 35 from moving in at least one direction, for example the distal axial direction, by interference with one or more members 57 of the ventricular part 32. Optionally, spur member 52 is formed as a spring, and elastically interacts with one or more members 57 so that downward forces on the atrial part 35 persist over a range of relative axial positions of atrial part 35 and ventricular part 32; for example, an axial displacement of up to 1 mm, 2 mm, 5 mm, or an intermediate range.

In some embodiments of the invention, spur member 52 expands during deployment, for example after release from a restraining tube, to interact with members 57, for example after relative rotation of ventricular part 32.

A potential advantage of spur member 52 is attachment of ventricular part 32 and atrial part 35 to prevent relative motion without additional clamping or suturing. A particular advantage is potentially obtained by disposing spur member 52 to resist distal motion of the atrial part 35 during ventricular systole, where high pressures in the left ventricle are caused by contraction of the left ventricle, tends to force a prosthetic mitral valve into the left atrium.

It should be understood that a spur member is alternatively or additionally provided with connections and forces acting in other directions. In one example, it is in the reciprocal position, attached to ventricular part 32 and protruding inward, so that a member of atrial part 35 which is below (proximal) to it is caught and restrained from upward movement, for example during ventricular systole.

Figure 28A:
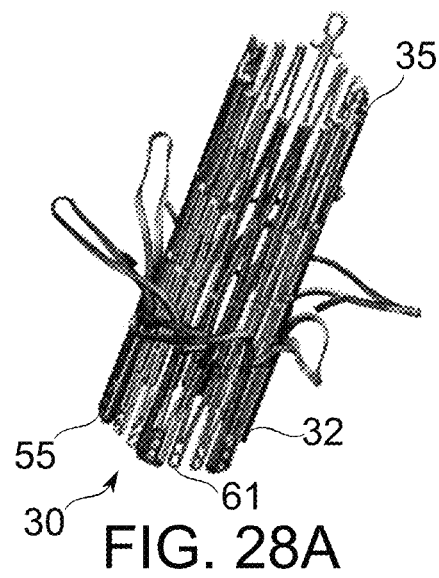
FIGS. 28A-28C are schematic perspective views of a ventricular part attachment structure and an atrial part attachment structure, suitable for attachment by suturing, in accordance with an exemplary embodiment of the invention.
Figure 28B:
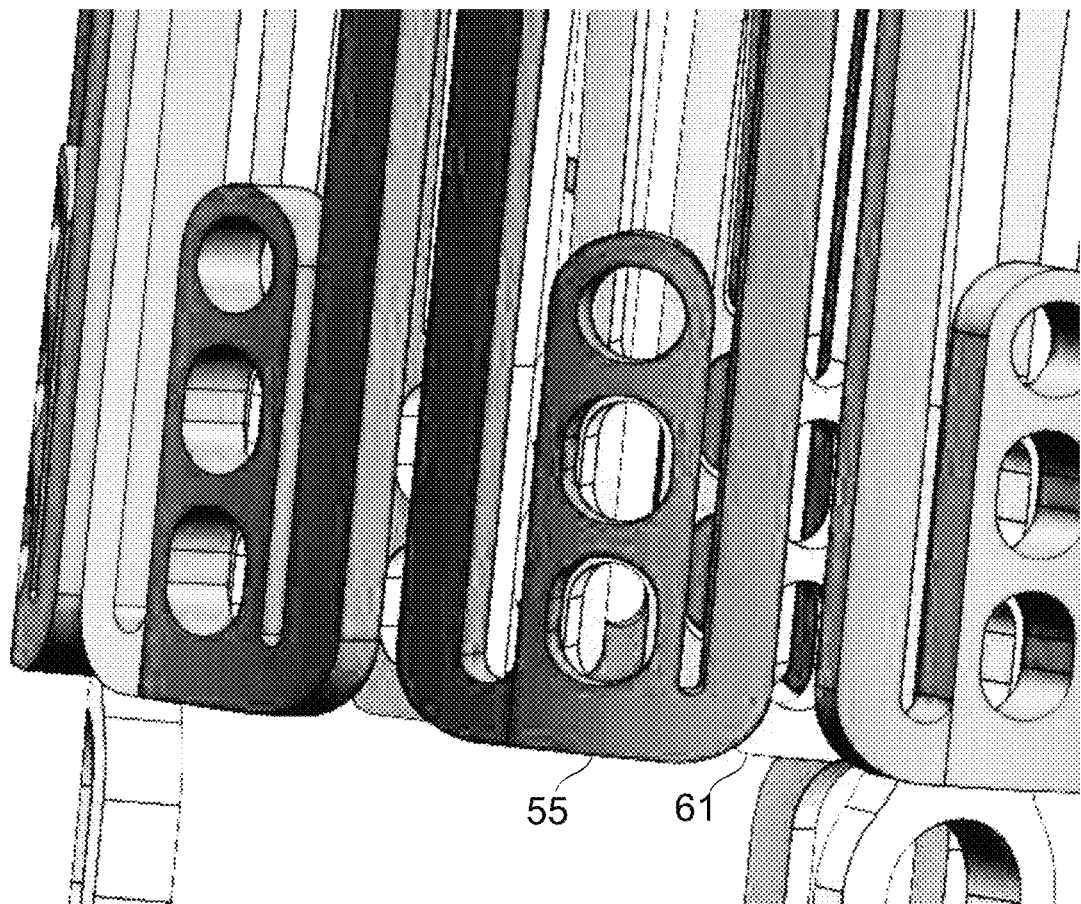
Figure 28C:
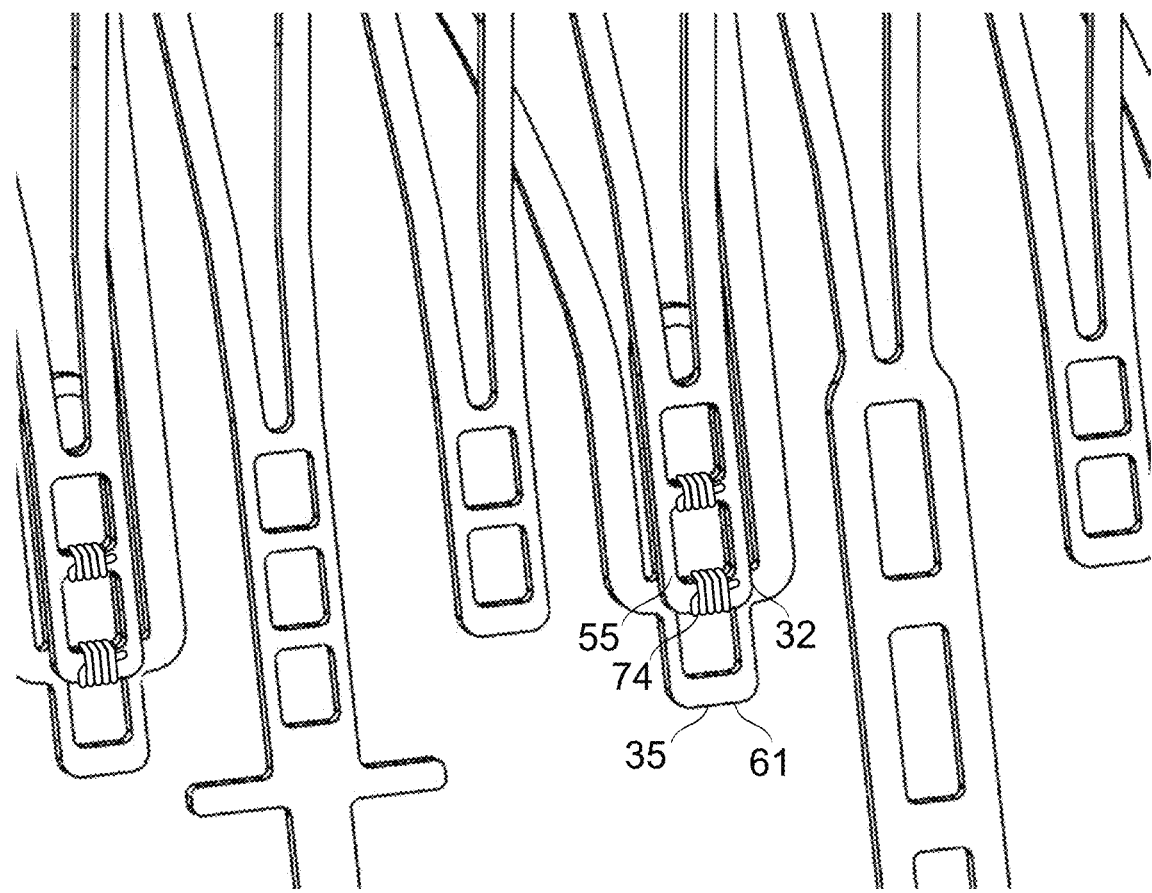

Reference is now made to FIGS. 28A-28C, which show schematic perspective partial views of an atrial part 35 inserted into a ventricular part 32, with a ventricular part attachment structure 55 and atrial part attachment structure 61, according to an exemplary embodiment of the invention. FIG. 28B shows a magnified view of a portion of FIG. 28A, at the proximal end of the mitral valve lumen 31.

In some embodiments of the invention, attachment structures 55, 61 are used to help ensure the connection between ventricular part 32 and atrial part 35. In some embodiments, continuous close relative positioning of the ventricular part 32 and the atrial part 35 helps ensure good prosthetic atrial valve fixation; for example, secure capture of the native atrial valve leaflets, which in some embodiments is pulled in between them during operations which recruits and pulls on the chords attached to the leaflets.

In some embodiments, attachment structures 55, 61 are provided with one or more apertures for securing together with sutures and/or securing hardware such as a bolt screw and matching nut. In some embodiments, a plurality of apertures is provided. In some embodiments, the apertures are oval. In some embodiments, the apertures are rectangular. This provides a potential advantage, for example, in alignment before securing, so that the parts do not need to be perfectly matched in order for there to be a clear pathway through a shared aperture. In some embodiments, apertures used for attachment are provided on facing surfaces that can be brought into close contact, so that the apertures can be secured tightly to each other.

FIG. 28C shows exemplary suturing 74 connecting attachment structures 55, 61 of the ventricular part 32 and the atrial part 35 of a prosthetic mitral valve frame. Optionally, suturing is performed, for example, using heart valve industry standard size 3/0 wires and standard size 12 beading needles.

Reference is now made to FIGS. 26A-26D, which show schematic perspective partial views of an atrial part 35 inserted into a ventricular part 32, with a protective insert 56 provided for use with ventricular part attachment structure 55 and atrial part attachment structure 61, according to an exemplary embodiment of the invention. A protective insert 56 provides a potential advantage for preventing scratching by with wire suture material.

Figure 26A:
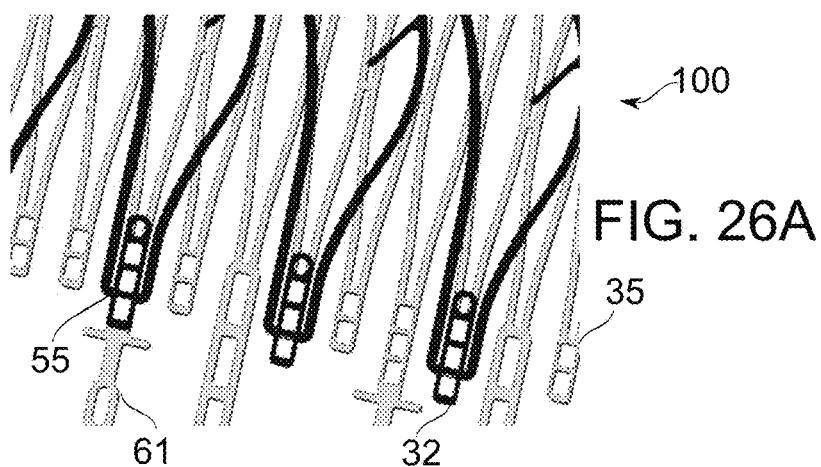
FIGS. 26A-26D are schematic perspective views of a protective insert provided for use with ventricular part attachment structure and atrial part attachment structure, in accordance with an exemplary embodiment of the invention.
Figure 26B:
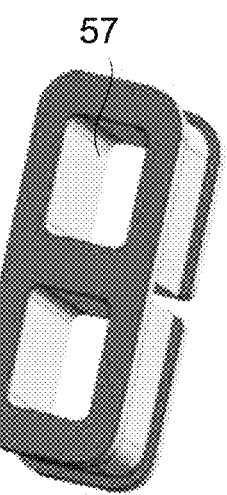
Figure 26C:
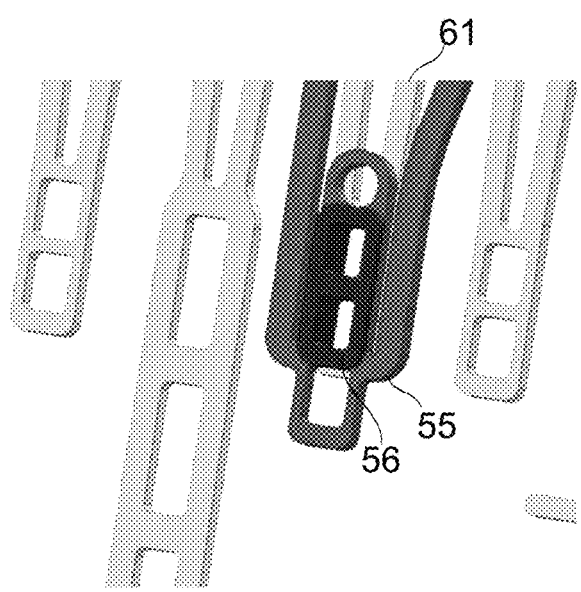
Figure 26D:
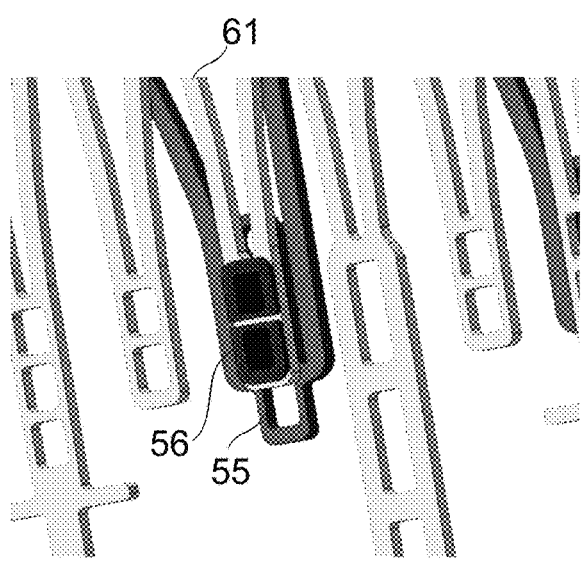

In FIG. 26A, unprotected attachment structures 55, 61 are shown. FIG. 26B shows protective insert 56 in detail. In some embodiments, protective insert 56 is comprised of a yielding and/or non-conductive material, such as silicone elastomer or plastic polymer. In some embodiments, insert 56 is shaped to be inserted into one or more apertures of attachment structures 55, 61, covering the metal. FIGS. 26C and 26D show the insert in position, viewed from the outside- and inside-facing sides of insert 56, respectively.

Potentially, insert 56 provides an advantage against wear of the underlying metal, such as scratching, by suturing material, particularly suturing material comprised of metal wire. Scratches and other surface damage are potential contributors to galvanic corrosion; preventing them provides a potential advantage for device durability.

Figure 27A:
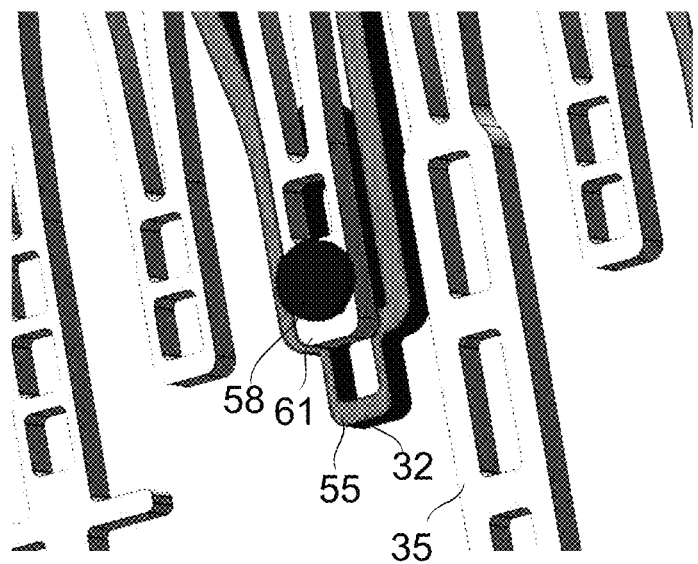
FIGS. 27A-27C are schematic perspective views of a screw and nut provided for use in attaching a ventricular part attachment structure to an atrial part attachment structure, in accordance with an exemplary embodiment of the invention.
Figure 27B:
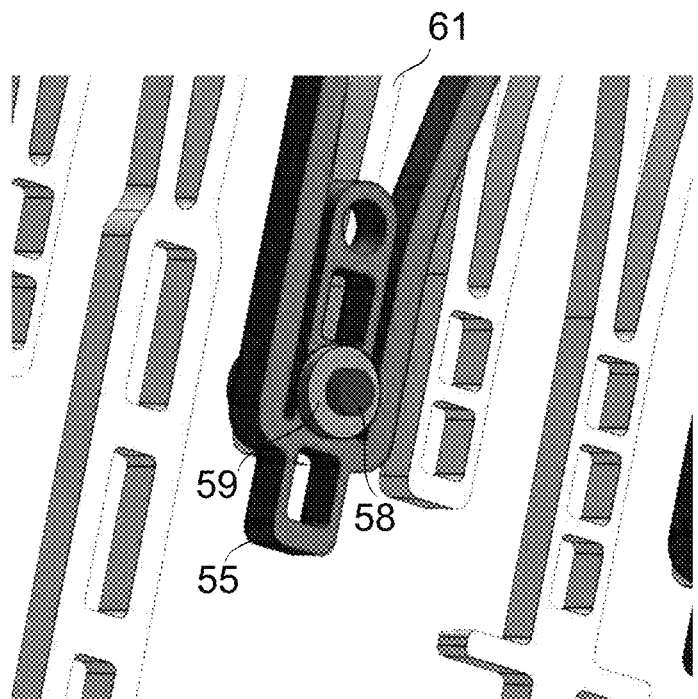
Figure 27C:
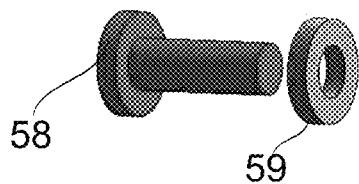

Reference is now made to FIGS. 27A-27C, which show schematic perspective views of a screw 58 and nut 59 provided for use in attaching ventricular part attachment structure 55 and atrial part attachment structure 61, according to an exemplary embodiment of the invention. In some embodiments, the ventricular part and the atrial part are attached to each other using screw-and-nut prior to insertion.

FIG. 27C shows the screw 58 and nut 59 part in exploded perspective view. FIGS. 27A and 27B show the screw 58 and nut 59 assembled through apertures of the attachment structures 55, 61 from the outside- and inside-facing sides of the attachment structures 55, 61, respectively.

Potentially, a screw and nut may be used to secure attachment between the ventricular part and the atrial part with a tighter association than is provided, for example, by suturing wire.

Figure 6A:
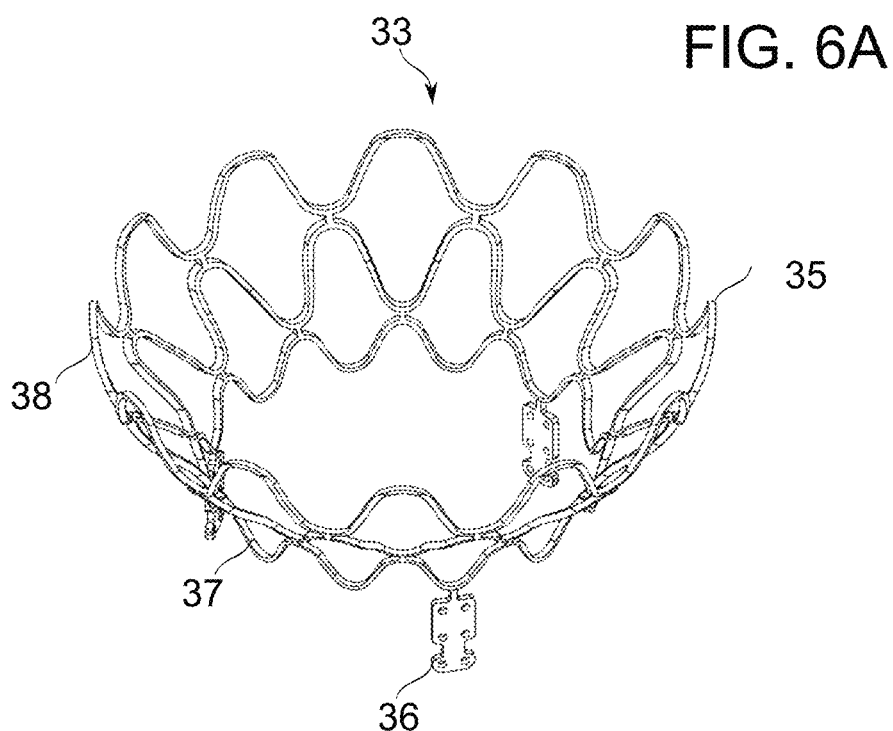
FIGS. 6A-6B schematically depict prosthetic mitral valves, in accordance with an exemplary embodiment of the invention.
Figure 6B:
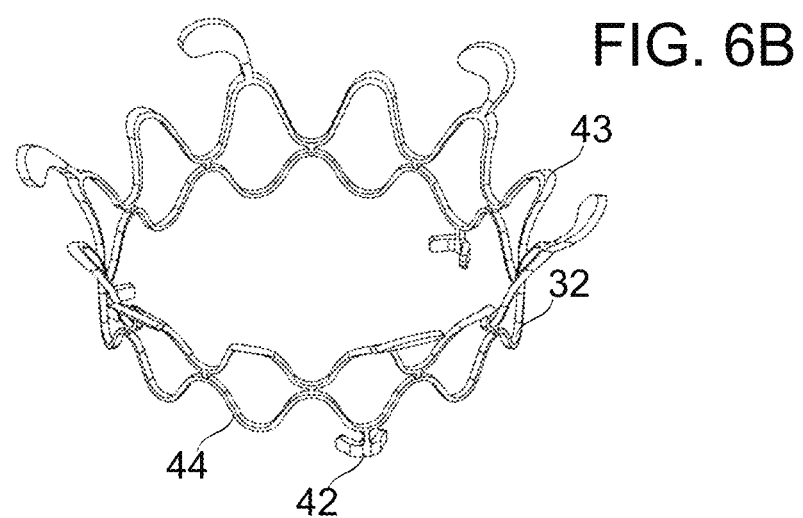
Figure 7A:
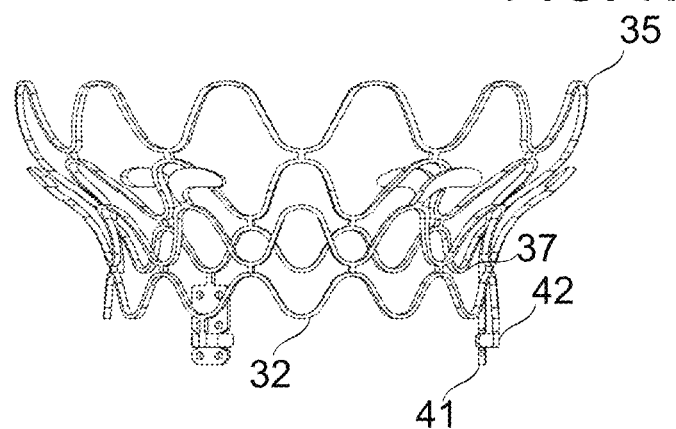
FIGS. 7A-7D schematically depict prosthetic mitral valves, in accordance with an exemplary embodiment of the invention.
Figure 7B:
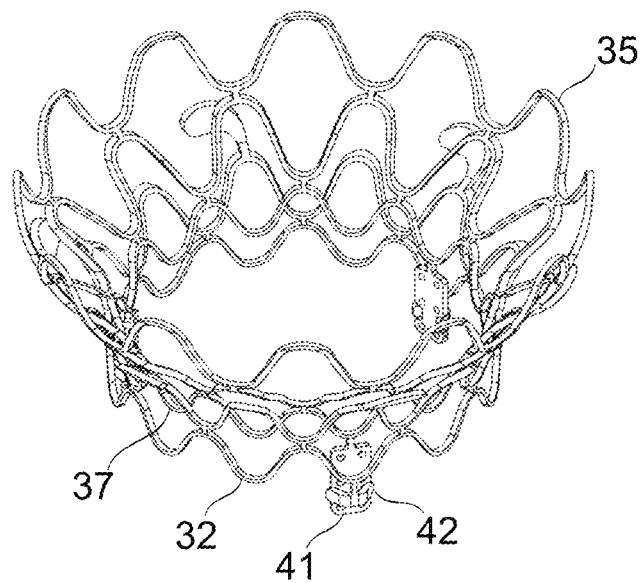
Figure 7C:
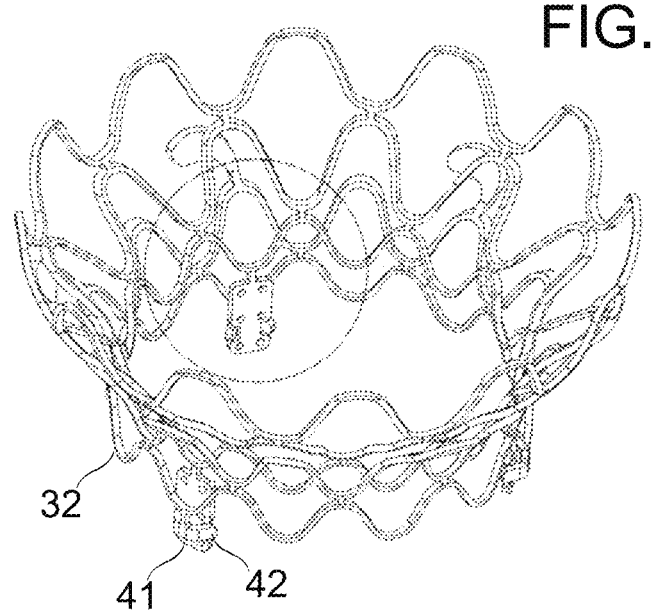
Figure 7D:
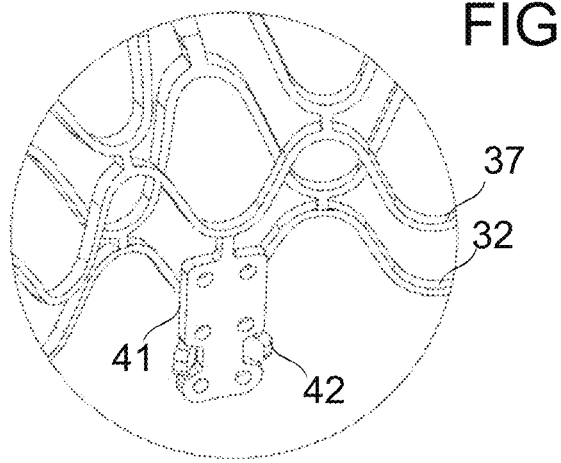
Figure 8:
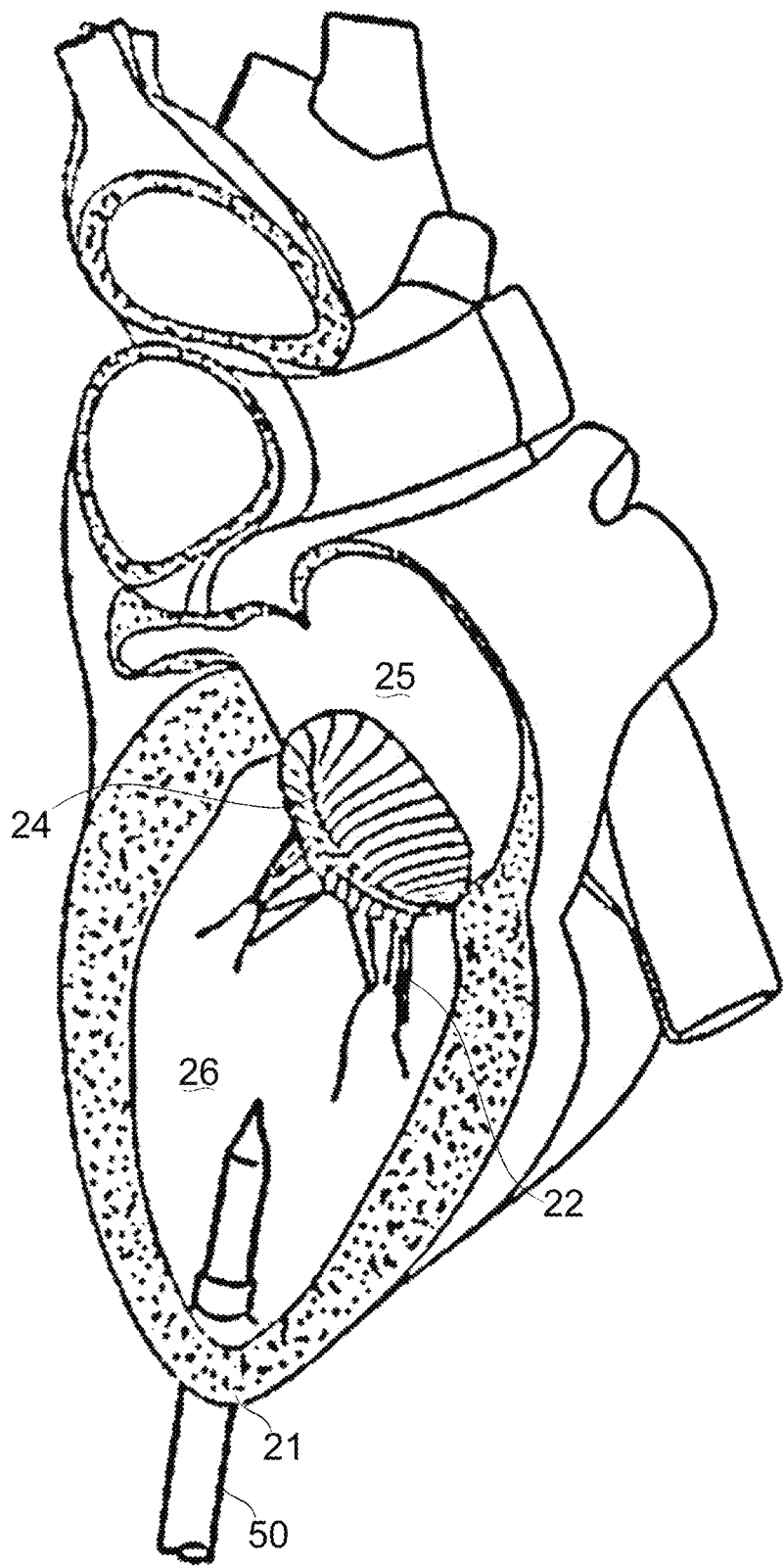
FIG. 8 schematically depicts an initial step in the deployment of a prosthetic mitral valve, in accordance with an exemplary embodiment of the invention.

Reference is now made to FIGS. 6A-6B, which depict two views of a prosthetic mitral valve unconstrained, according to an exemplary embodiment of the invention. In some embodiments, the size and shape of atrial part 35 are adapted for deployment inside a left atrium of a heart. In deployment, proximal portion 37 passes into a mitral valve annulus, while the outer surface of distal portion 38 snugly rests against the inner walls of the left atrium in proximity of the mitral valve annulus.

In some embodiments corresponding to the deployed configuration depicted in FIG. 6B, ventricular part 32 comprises a ring. In some embodiments, the ring has an outer diameter at ventricular part distal end 43 of 34 mm, 36 mm, 38 mm, 40 mm, 42 mm, any diameter in between, or a longer or shorter diameter. In some embodiments, the outer diameter at proximal end 44 is 28 mm, 30 mm, 32 mm, 34 mm, any diameter in between, or a longer or shorter diameter. In some embodiments, the length of ventricular part 32 is 8 mm, 9 mm, 10 mm, 12 mm, any length in between, or a longer or shorter length. In some embodiments, lockers 42 enclose tabs 41 creating an attachment between atrial part 35 and ventricular part 32.

Reference is now made to FIGS. 7A-7D, which depict four views of an exemplary prosthetic mitral valve unconstrained in a deployment configuration, according to an exemplary embodiment of the invention. The size and shape of ventricular part 32 is such that when atrial part 35 is deployed inside a left atrium of a heart as described above, ventricular part 32 can be placed so as to encircle a part of the proximal portion 37 of atrial part 35 and the native mitral valve leaflets of the heart. In some embodiments, atrial part 35 is biased to self-expand to a diameter which presses against the interior of ventricular part 32. Potentially, pressing between the two parts creates a frictional association which aids in fixation. In particular, a tighter association between the two parts potentially serves to entrap a mitral valve leaflet which has been drawn between them. In some embodiments, atrial part 35 protrudes proximally to ventricular part 32 when deployed, as well as distally. Optionally, atrial part 35 expands wider than ventricular part 32 in the protruding portions. Potentially, this creates a shape-locking association between the two parts, so that ventricular part 32 is locked axially into place along the extent of atrial part 35. In a deployed configuration, lockers 42 at least partially wrap around tabs 41, thus maintaining ventricular part 32 and atrial part 35 fixed one to the other.

Fixation of the Prosthetic Mitral Valve Embodiments

Initial Insertion

Figure 32:
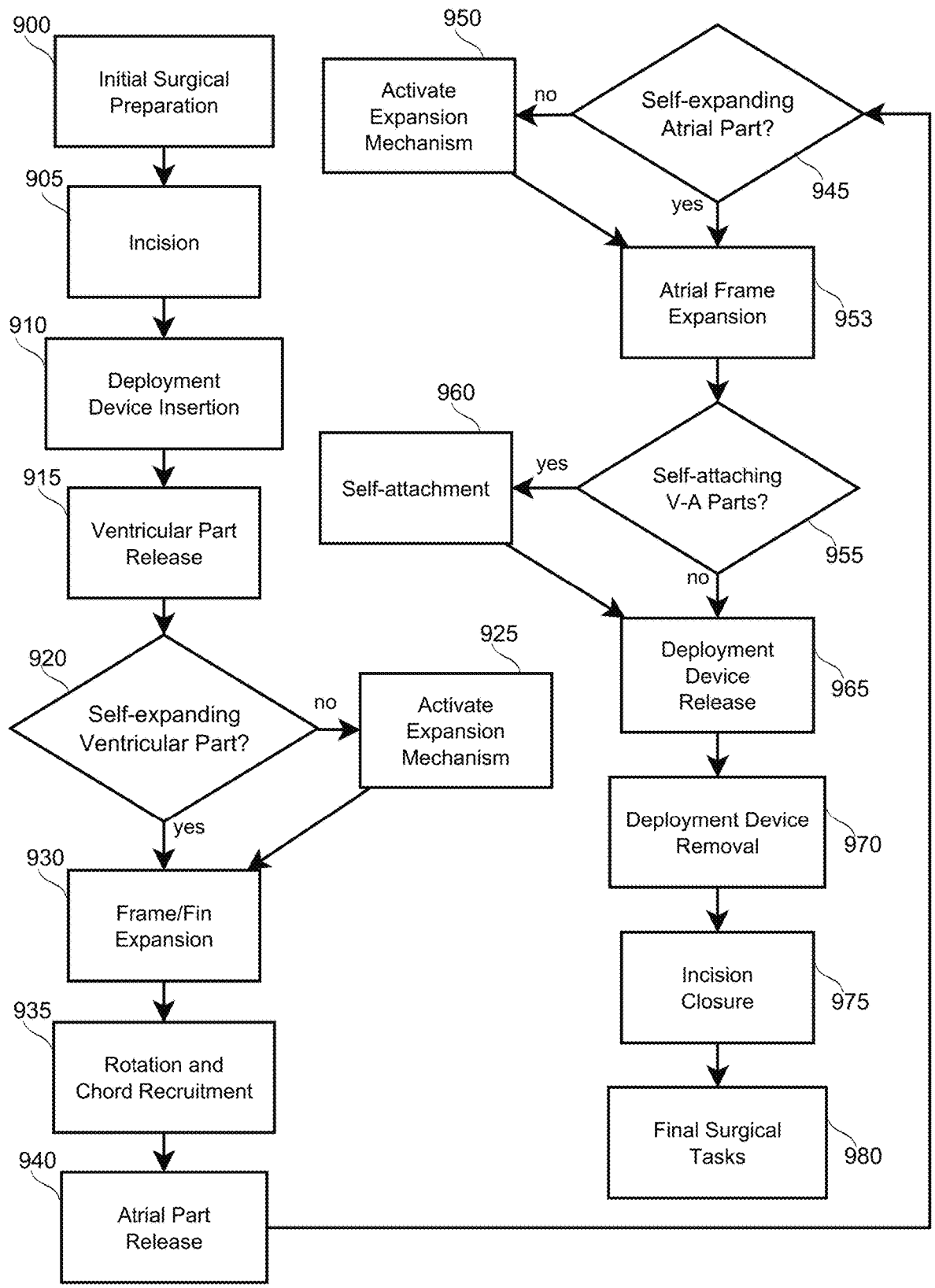
FIG. 32 is a flowchart giving a sequence of steps for prosthetic mitral valve implantation, in accordance with an exemplary embodiment of the invention.

Reference is now made to FIGS. 8-11 and FIGS. 30A-E, which schematically illustrate an exemplary method for deploying a prosthetic mitral valve 10 as described herein, using a catheter deployment system 50, according to exemplary embodiments of the invention. Reference is also made to FIG. 32, 900-980 which is a flowchart listing exemplary steps in the surgical implantation of some exemplary embodiments of the invention.

In some embodiments of the invention, a prosthetic mitral valve 10 is implanted transapically using a catheter deployment system. In some embodiments, and according to medical indications, an open heart surgical procedure is used.

Figure 9:
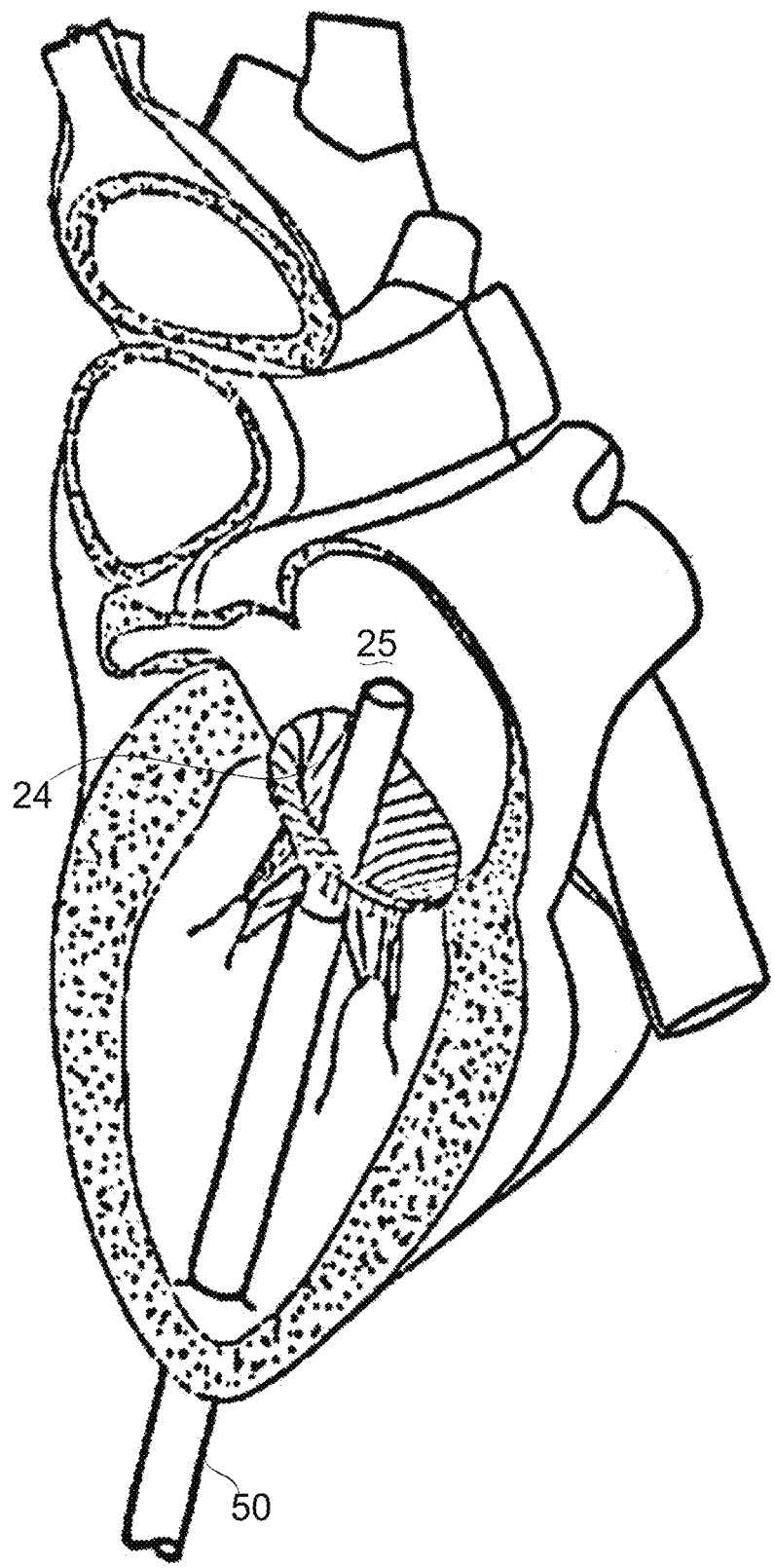
FIG. 9 schematically depicts a subsequent step in the deployment of a prosthetic mitral valve, in accordance with an exemplary embodiment of the invention.

After surgical preparation 900, and fluoroscopic observation, apex 21 is punctured 905 and a catheter deployment system 50 is passed through the apex (FIG. 8) 910. In some embodiments of the invention, catheter deployment system 50 is guided to the left ventricle 26 and then passed retrograde through the native mitral valve 24 to the left atrium 25, as depicted in FIG. 9.

Optionally, ventricular part 32 and atrial part 35 are held in the compressed state by one or more sheaths. Optionally or additionally, the sheaths are arranged around parts 32 and 35 so that ventricular part 32 and atrial part 35 are separately expandable. Optionally, ventricular part 32 is expandable before atrial part 35.

Figure 30A:
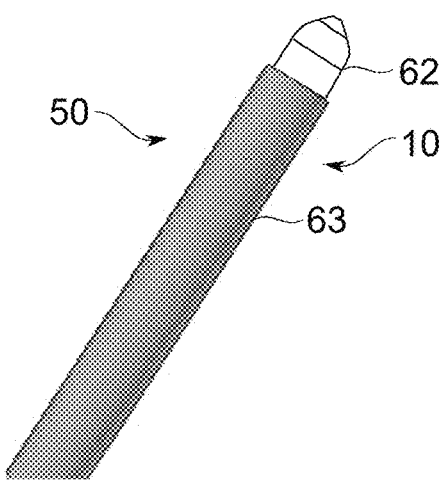
FIGS. 30A-30E schematically illustrate the deployment of a prosthetic mitral valve, in accordance with an exemplary embodiment of the invention.
Figure 30B:
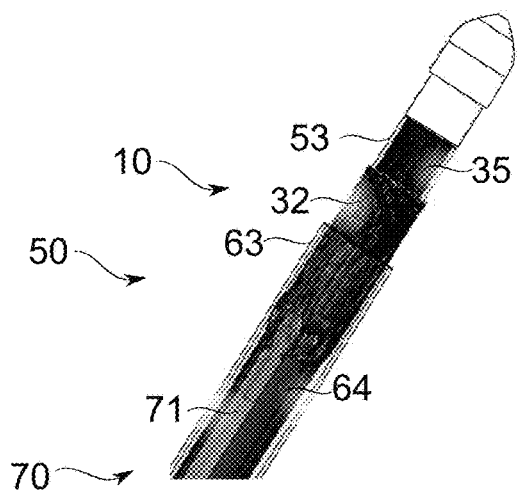

In some embodiments of the invention, there are at least three parts acting as sheaths in catheter deployment system 50, as shown in FIG. 30A: an overtube 63, a nosecone 62, and an atrial part retaining tube 53. Overtube 63 contains the proximal parts of prosthetic mitral valve 10. Nosecone 62 confines the distal parts of the prosthetic mitral valve 10, and in particular the distal end of the atrial part. In FIG. 30B, the overtube 63 is shown partially retracted, and partially transparent to reveal underlying detail. Underneath, retaining tube 53 (also shown transparent) overlies at least the proximal portion of atrial part 35.

In some embodiments of the invention, ventricular part 32 is rotated during deployment, for example as detailed in the next section. Fork 70 is a deployment clamp which holds ventricular part 32 during this rotation. It is attached to the base of ventricular part 32 through prongs 71. Optionally, another sheath, shank tube 64, is provided between deployment clamp/fork 70 and atrial part 35 which prevents movement of the atrial part 35 during fork rotation.

Ventricle Part Expansion and Chord Capture

Figure 10:
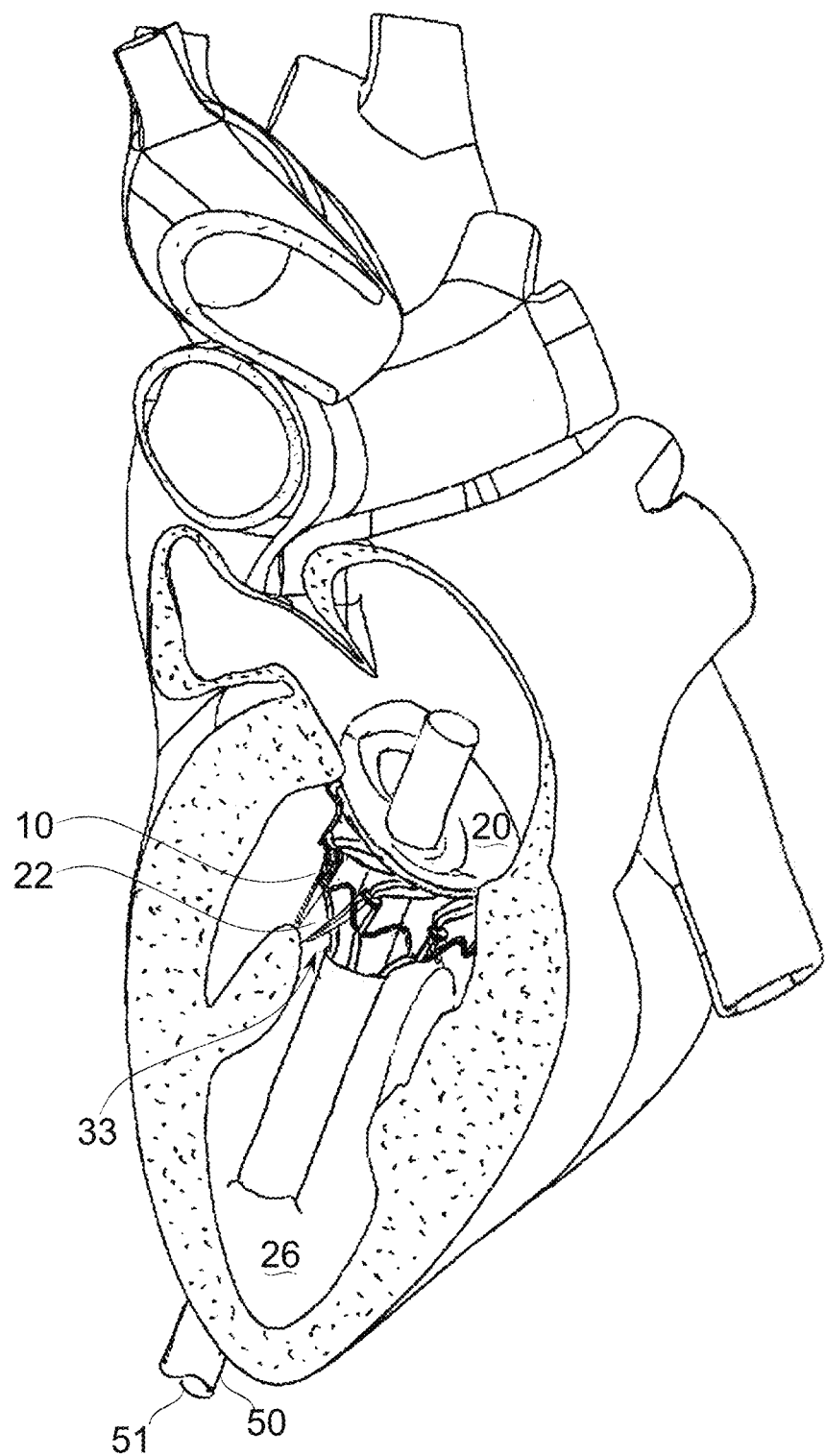
FIG. 10 schematically depicts an expansion step in the deployment of a prosthetic mitral valve, in accordance with an exemplary embodiment of the invention.

In some embodiments, after passing the catheter deployment system through the native mitral valve 24, a proximal end 51 is retracted (for example, the sheath is pulled) proximally, as in FIG. 10 to release ventricular part 32 from its compact containment 915.

In some embodiments, ventricular part 32 is self-expanding 920, and then expands 930 to a properly deployed position in left ventricle 26. Non-self-expanding embodiments of the ventricular part may be expanded, for example, by an expansion mechanism acting on it from inside, for example, a balloon catheter 925. In some embodiments, arms 34 radially extend to a deployed position. In some embodiments, the extended arms are inserted among the chords of the mitral valve.

Figure 30C:
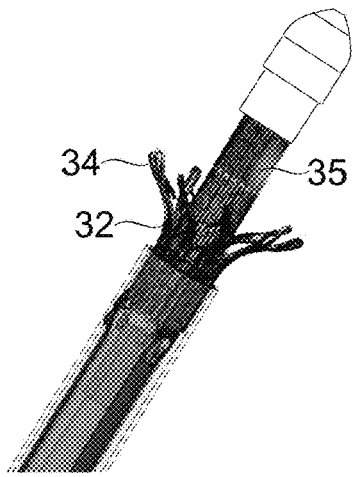
Figure 30D:
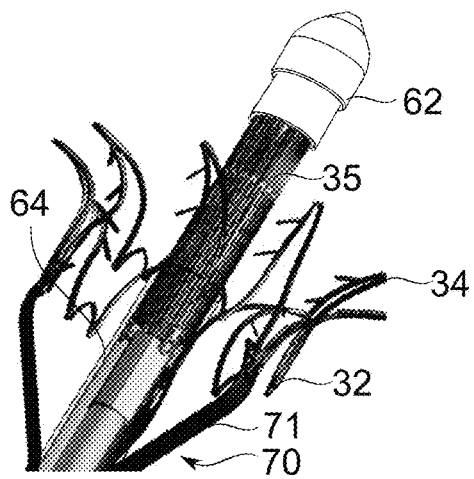

In some embodiments, as illustrated by FIG. 30C, when the overtube 63 has been retracted sufficiently, the arms 34 of ventricular part 32 undergo a conformational change, and extend toward their deployed configuration. FIG. 30D shows the overtube fully retracted. In some embodiments, fork 70 is a deployment clamp attached to ventricular part 32, in order to manipulate it (and in particular, rotate it) after expansion. In some embodiments, it expands along ventricular part 32. Optionally, atrial part 35 is still held in place by nosecone 62 and atrial part retaining tube 53.

In some embodiments, once arms 34 are in deployed position, catheter deployment system 50 or a part of it is rotated 935, thus inducing rotation of the arms of ventricular part 32. In some embodiments, at least a portion of the rotation is induced by the conformational changes that put the arms in their deployed position. In some embodiments, arms 34 physically engage with native chords 22, pulling them around the mitral valve 10 axis. In some embodiments, the maximum moment exerted during rotation is 2 cNm, 5 cNm, 10 cNm, 15 cNm, or any value in between, or a greater or lesser value, as determined to be appropriate for the conditions of deployment. In some embodiments, the rotation imparted is about 10 degrees, about 20 degrees, about 30 degrees, about 60 degrees, about 120 degrees, or other smaller, intermediate or larger degrees of rotation.

In some embodiments of the invention, arms 34 are first partially deployed, for example, by removing overtube 63 only partially. In some embodiments of the invention, arms 34 are designed to be smooth to at least a partially deployable point along their length. Potentially, this allows the arms 34 to be repeatedly partially deployed, optionally rotated, and then retracted again; until the operator is satisfied that the arms 34 are deployed to a position which is sufficient to encounter the chords of the mitral valve and recruit them for prosthetic valve fixation. In some embodiments, full deployment of the arms follows, for example, by complete retraction of overtube 63. In some embodiments, projections attached to the arms are exposed by full deployment, allowing their use in the final tensioning and recruitment of the chords of the mitral valve for prosthetic valve fixation.

Reference is now made to FIGS. 31A-31I, which are schematic diagrams illustrating the recruitment of mitral valve chords during deployment of an arm 34, according to exemplary embodiments of the invention. The view is from the atrial side of the deploying valve ("above" it).

Figure 31A:
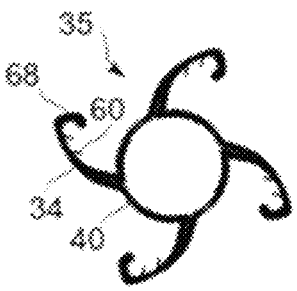
FIGS. 31A-31I schematically illustrate the recruitment of native mitral valve chords for prosthetic mitral valve frame fixation, in accordance with an exemplary embodiment of the invention.

Corresponding to some embodiments of the invention, FIG. 31A shows arms 34 of an exemplary ventricular part 32, attached to a supporting rim 40. In some embodiments, arms 34 are provided with projections 60, for example as described in FIG. 17, and a hook 68.

Figure 31B:
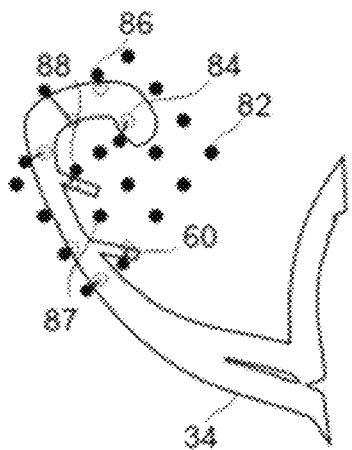
Figure 31C:
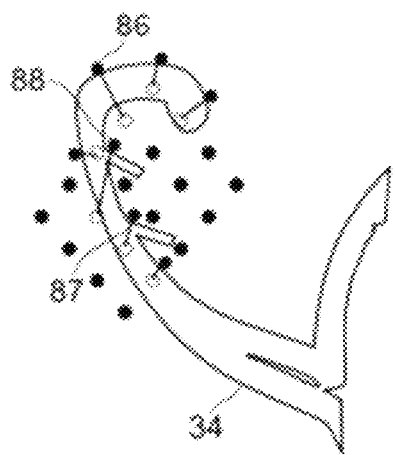
Figure 31D:
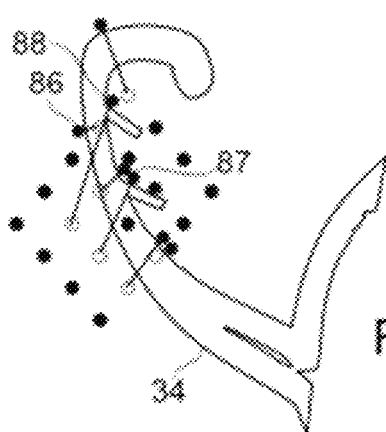

In FIGS. 31B, 31C, and 31D, one representative arm 34 is shown in three successive rotational positions. The dotted circles 84, represent potential undeflected positions of chords stretching perpendicular to the plane of the illustration, before arm deployment. Many positions are shown to illustrate what may occur in different deployment configurations, and not as an illustration of actual anatomy.

Filled circles 86 represent potential deflected positions of chords touching arm 34, and filled circles surrounded by a dotted boundary 82 represent potential positions of undeflected chords. Deflected chords are further indicated by a line connecting the deflected and undeflected positions.

As the arm undergoes a conformational change from its delivery configuration, it potentially passes between and/or interacts with chords in different positions along its extent. In FIG. 31B, some chords 88 are in potentially captured contact with structures of the arm, while others are uncontacted 82, 87, or have been pushed aside 86 during deployment. During the conformational changes which lead to the position of FIG. 31B from an initially compacted form, some chords may have been transiently deflected (not shown). In some embodiments, the extension of an arm 34 into the region of the chords of the mitral valve is itself generative of tensile forces within one or more chords acting on the prosthetic valve frame. For example, in FIG. 31A, several chord positions, including deflected chord positions 88, 86, are displaced from their undeflected configuration as a result of arm 34 extension. Potentially (and whether or not insertion alone results in a net torque on arm 34 within the plane of the exemplary drawing), a component of the tension forces acting on displaced chords acts, for example, to recruit the leaflets of the native mitral valve into closer association with the prosthetic valve frame.

In FIG. 31C, the arm 34 has been rotated clockwise. As a result, some previously captured chords 88 have stretched. Other chords 87 have been recruited. By the rotational position of FIG. 31D, several chords have been recruited. In some embodiments, forces exerted by these recruited chords are used to assist in the fixation of the prosthetic mitral valve, according, for example, to the mechanisms of interaction described herein.

Figure 31E:
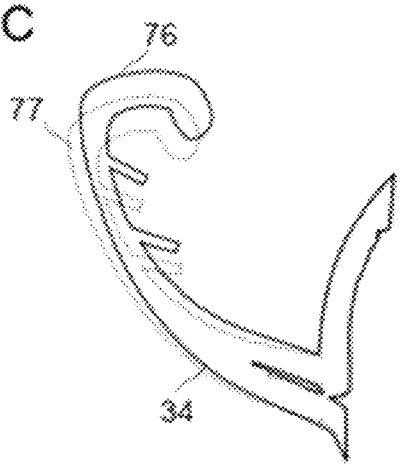

In some embodiments, the situation of FIG. 31C may also be achieved without externally exerted rotational motion. FIG. 31E illustrates an embodiment in which chord-recruiting motion is internally generated by the structure of the arm and/or its mounting. Optionally a self-expanding arm 34 may be preset to initially expand more radially, so that it inserts among the chords, for example to position 77. In some embodiments, as conformational changes continue, the arm receives an angular displacement, so that it moves, for example, toward position 76. The difference in position illustrated is similar in size to the movement of arm 34 between FIG. 31B and FIG. 31C, but may be larger or smaller depending on the particular design. This motion potentially plays a role in chord recruitment.

Figure 31F:
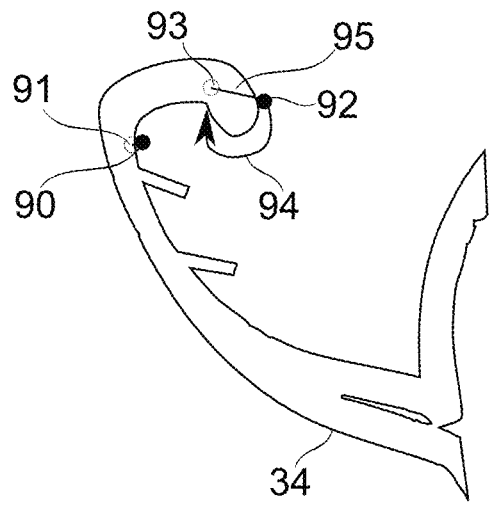
Figure 31G:
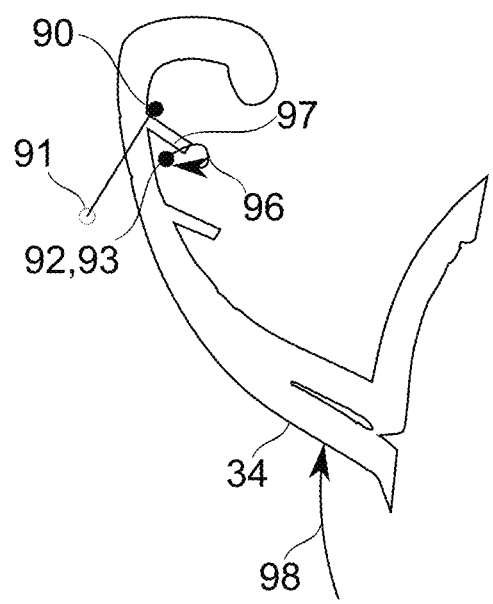
Figure 31H:
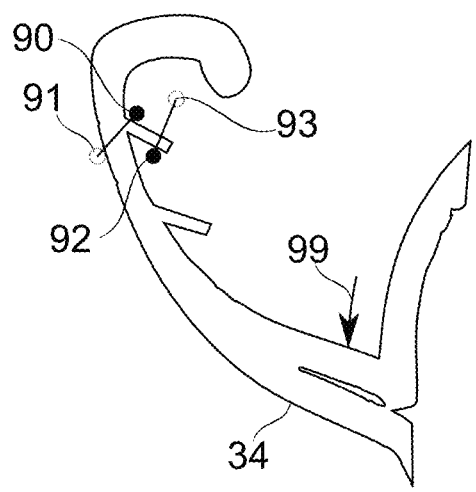

In some embodiments of the invention, at least a portion of the tension generated on the chords through displacement by the arms 34 during deployment is maintained, in some deployment configurations, between two or more chords stretched in opposing directions. In FIGS. 31F, 31G, and 31H, one representative arm 34 is shown in three successive rotational positions where it interacts with at least two chords 90, 92. In FIG. 31F, chord 90 has been captured during initial extension of arm 34 amongst the chords of the native mitral valve. It is slightly displaced from its resting position 91. Chord 92 has not been captured, but is also displaced from its resting position 93.

In the example, as arm 34 rotates through an angle 98 from the position of FIG. 31F toward the position of FIG. 31G, chord 92 is captured by arm 34 after chord 92 slips around hook 95 along a path relative to hook 95 indicated by arrow 94. As arm 34 continues to rotate toward the position of FIG. 31G, chord 92 slips around projection 97 via a path indicated by arrow 96, and is captured again on an inner side of projection 97.

At the position of the exemplary arm 34 shown in FIG. 31G, chord 90 is displaced from undeflected position 91. Chord 92, in this example, is undeflected and has returned to undeflected position 93. If arm 34 is locked at this point—for example, by further deployment of the prosthetic mitral valve frame—then chord 90 remains under tension and participates in valve frame fixation, while chord 92 is not under tension induced by valve frame deflection.

In the exemplary deployment configuration shown, however, even if exemplary arm 34 is allowed to reach an equilibrium position without additional locking, at least some tension in the captured chords will be retained. The position of FIG. 31H, for example, reflects a rotational position assumed after rotating arm 34 through angle 99, which returns arm 34 partially from the position of FIG. 31G toward the position of FIG. 31F.

At this position, both chords 90, 92 are deflected from their original positions 91, 93, in opposing directions. Because their deflections are in opposed directions, the net torque exerted by the two chords together is lower than the torque exerted by either alone, and is potentially zero. Nevertheless, each chord is under tension. In some embodiments, this may serve, for example, to pull one or more leaflets of the native mitral valve into closer association with the mitral valve frame.

Figure 31I:
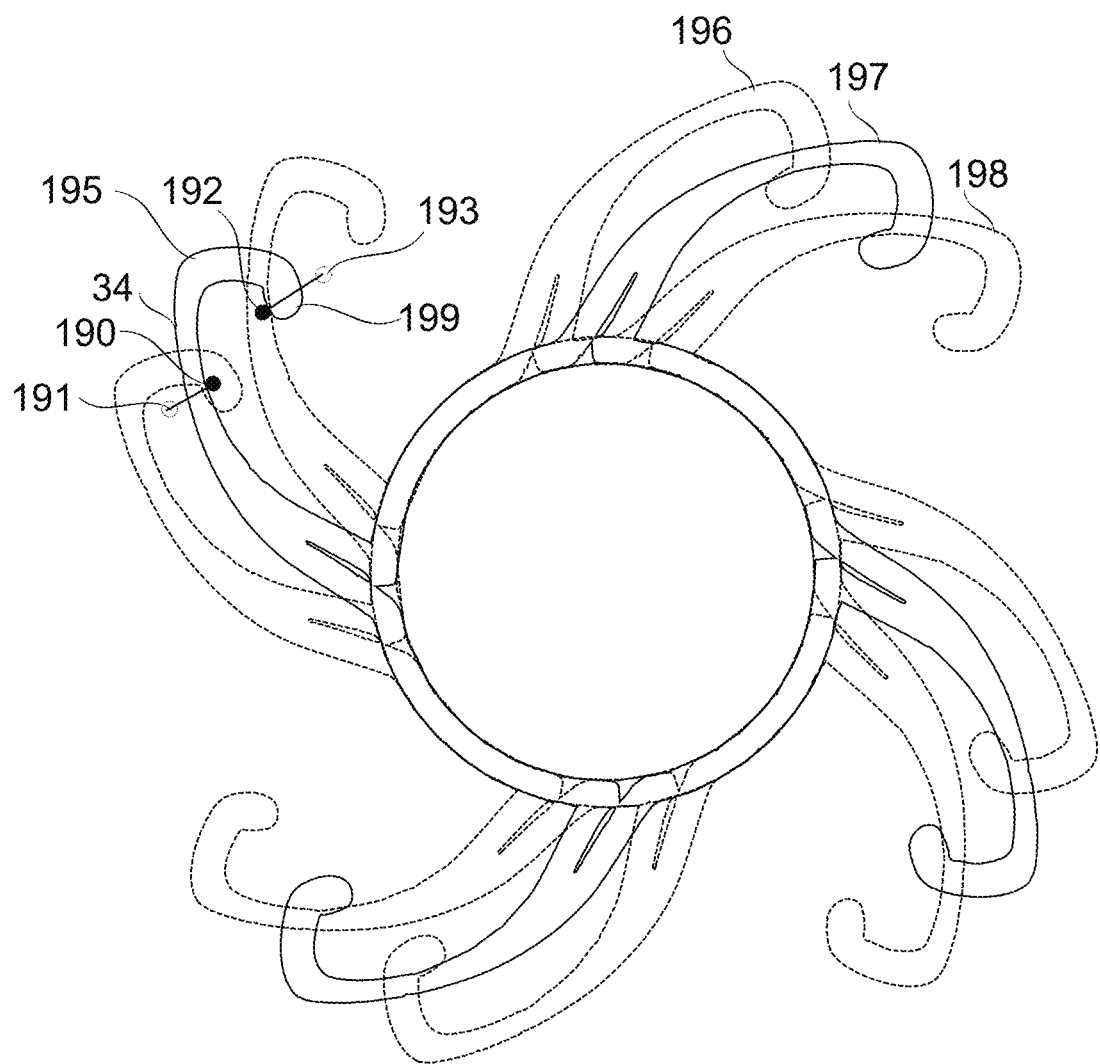

FIG. 31I exemplifies a similar sequence of positions to those just described with respect to FIGS. 31F-31H, with a larger portion of an exemplary ventricular part shown for clarity. Initial position 196 of the ventricular part of the mitral valve frame and fully rotated position 198 are shown in dotted lines. Final position 197 is shown in solid lines. In initial position 196, an undeflected chord in position 191 is captured by hook 195, and protruding part 199 of hook 195. A chord in chord position 193 is not captured. During rotation from initial position 196 to fully-rotated position 198, protruding part 199 transiently deflects a chord at chord position 193, then brushes past, so that the chord returns to its original position 193 and is captured within the region defined by the hook 195. In some embodiments, rotation to fully-rotated position 198 is under external force, such as from a rotating component of the catheter deployment system. Upon release of the external force, the displacement force of the chord captured at 191 pulls the ventricular part back toward its first position. However, the chord captured at position 193, once the protruding part 199 of hook 195 contacts it, exerts an opposing force. The final ventricular part position 197 potentially represents a position of equilibrium between opposing forces. The force exerted by the chord captured at 191, and finally deflected to position 190, is counterbalanced by the force exerted by the chord captured at 193 and finally deflected to position 192.

It should be noted that the sequence of FIGS. 31F-31I shows that the development of tension in the chords which fixates the mitral valve frame may be enhanced by movements of the arms which work the chords into captured positions, with or without net rotation of the arms. In some embodiments of the invention, a plurality of reciprocating rotation movements are applied in order to increase engagement of the chords so that they are recruited into fixation of the prosthetic valve.

In the above descriptions, it is chords which are named as being recruited and tensioned by interactions with arms 34. It should be noted, however, that, optionally, the arms additionally or alternatively interact directly with one or more native valve leaflets, to which the chords directly lead.

Figure 19:
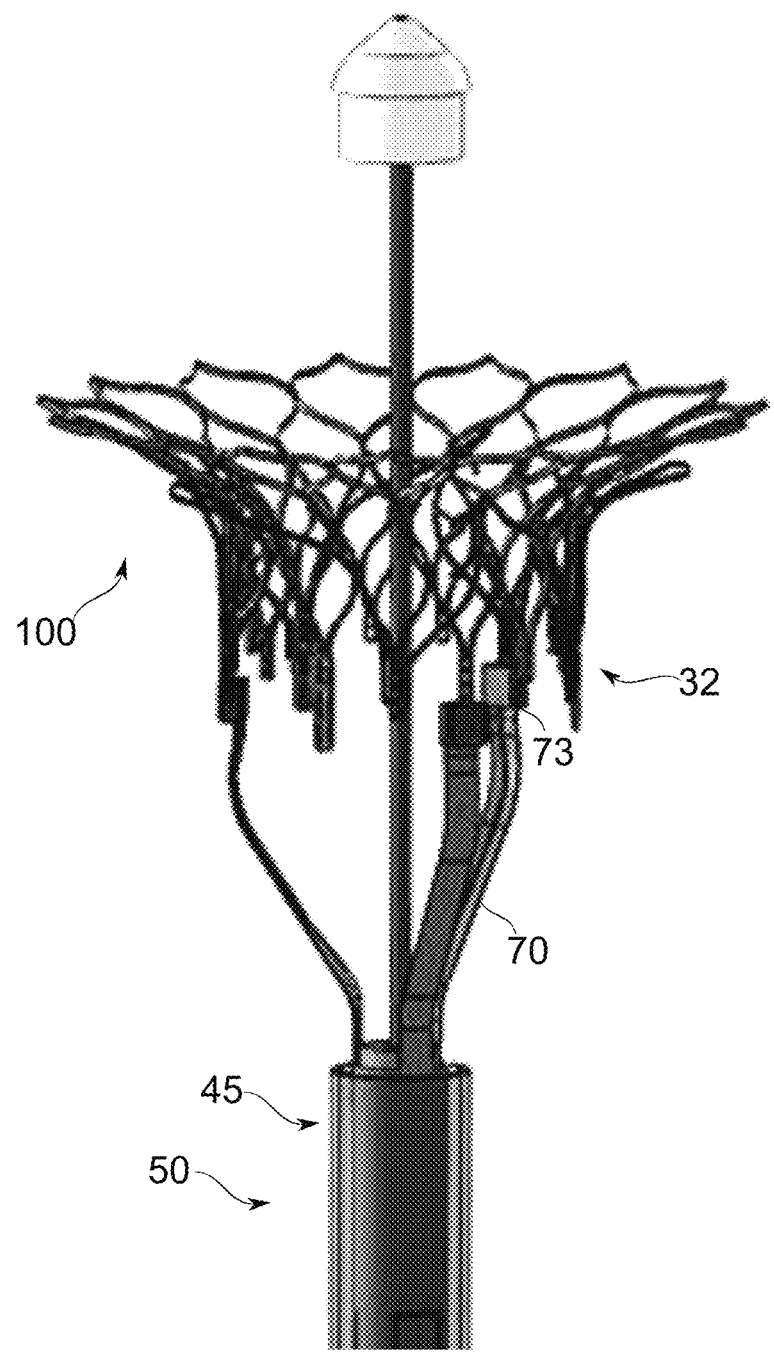
FIG. 19 is a schematic perspective illustration of portion of an exemplary catheter deployment system having a rotation component in functional association with a prosthetic mitral valve, in accordance with an exemplary embodiment of the invention.

Reference is now made to FIG. 19, which is a schematic perspective illustration of portion of an exemplary catheter deployment system 50 having a rotation component 45 including a fork 70 attached to the prosthetic mitral valve 100, according to an exemplary embodiment of the invention.

In some embodiments, for proper placement, rotation imparted to the ventricular part 32 during deployment is maintained until full deployment of the prosthetic mitral valve ensures that the leaflets of the native mitral valve 24 are captured. Potentially, this helps to ensure full participation of the chords in device fixation.

In some embodiments fork 70 comprises a region of contact 73 with the ventricular part 32 of the mitral valve 100. In some embodiments, fork 70 attaches to ventricular part 32, opens along with the expanding ventricular part, and maintains its attachment through the phase of atrial part deployment. In some embodiments, this association maintains the rotation of the ventricular part until deliberate detachment.

Figure 30E:
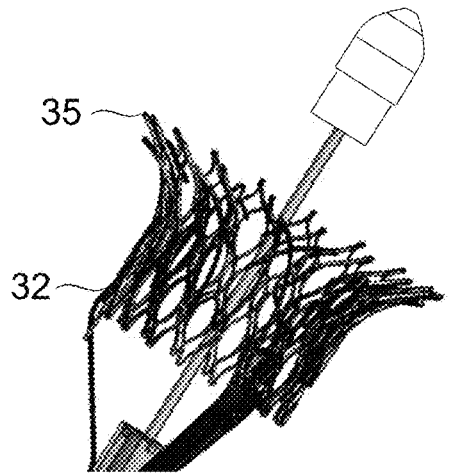

In some embodiments of the invention, attachment is maintained until the atrial part 35 is deployed. FIG. 30E shows nosecone 62, atrial part retaining tube 53, and shank tube 64 all retracted 940 from atrial part 35. In some embodiments, atrial part 35 self-expands 945 to its deployed configuration 953 as restraining parts are removed. Alternatively, atrial expansion may be driven by activating an expansion mechanism 950 such as a balloon catheter.

In some embodiments, the atrial part has elements 955 which attach to and/or interlock with 960 structural members of the ventricular part 32, for example, as herein described in relation to FIGS. 5A-7D, 22A-22C, and 25A-25B.

In some embodiments, restraints on the expansion of the atrial part are separately or partially removable: for example, advancement of just the nosecone 62, and/or only partial retraction of atrial part retaining tube 53. In some embodiments of the invention, partial removal of restraints on atrial part deployment results in functional deployment of the prosthetic valve mechanism in the still-beating heart, without attachment of the atrial part 35 to the ventricular part 32. Potentially, this allows a longer period for deployment operations which manipulate the ventricular part; for example, to more thoroughly engage the arms with the chords. In some embodiments, after the ventricular part is fully positioned, remaining restraints on the deployment of the atrial part 35 are removed.

In some embodiments, separation of the prosthetic valve frame into a separate ventricular part 32 and atrial part 35 allows the parts to be packaged more compactly for delivery. For example, the atrial part 35 can be packaged on a catheter deployment system distal to the ventricular part 32, so that the maximum diameter of the portion of the deployment system that enters the heart is not expanded by having the two parts overlap one another.

In some embodiments, the atrial part 35 and ventricular part 32 are attached prior to implantation; for example, as described herein in relation to FIGS. 5A-7D, 26A-26D, 27A-27C, and 28A-28C.

Control and Safety During Chord-Capturing Rotation

Figure 12:
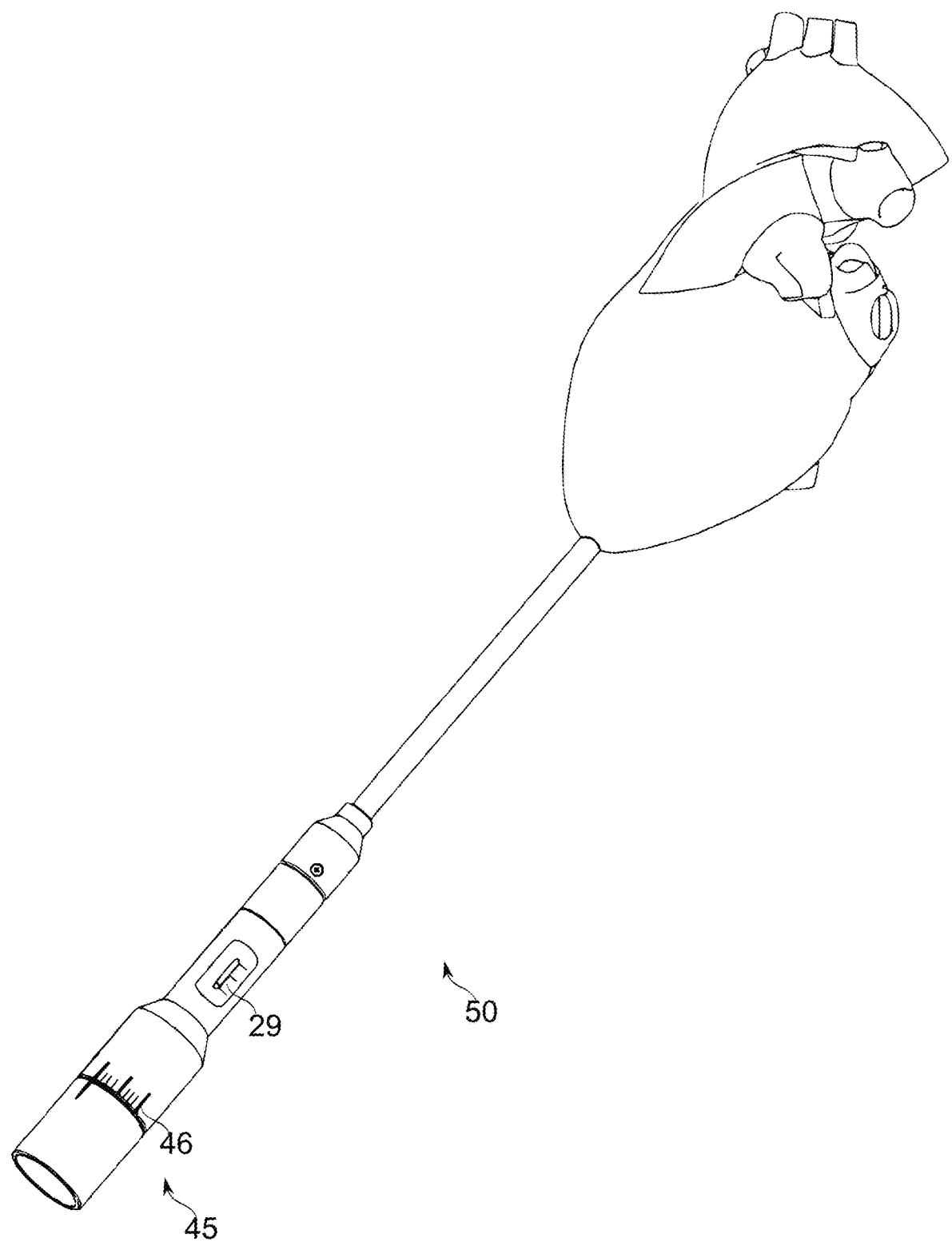
FIG. 12 schematically depicts a part of a catheter deployment system, in accordance with an exemplary embodiment of the invention.

FIG. 12 depicts distal portions of a rotation component 45 incorporated in catheter deployment system 50. After deploying the ventricular part (not depicted here), rotation initiated at a proximal end of the rotation component 45 induces rotation of at least the ventricular part around the mitral valve axis. In some embodiments of the invention, rotation component 45 includes a sensor measuring the torque force being applied to chords and leaflets. In some embodiments, rotation component 45 includes indexes of the rotation angle 46 and/or torque force 29 being applied. In some embodiments, the rotation angle and torque force are predetermined by the design of the rotation component. In some embodiments, rotation itself is induced by direct manipulation of a rotating component (for example, a proximal end of rotation component 45). In some embodiments, rotation is induced by triggered coupling of an internal actuation energy source, for example, a tensioned spring, to rotation component 45. Optionally, rotation to the preset angle occurs automatically when the operator performs a single triggering operation, such as pressing a button.

Reference is now made to FIGS. 23A-23D, which are schematic sectional views showing tissue safety mechanism 700, comprised in rotation component 45, according to an exemplary embodiment of the invention.

In some embodiments of the invention, a tissue safety mechanism 700 is provided which transmits force only below a preset threshold. To protect against damage to tissue during deployment, it is potentially an advantage to provide a clutch mechanism which acts as a stopper to prevent the rotational force applied during capture of the valve chords from exceeding a predetermined limit.

In some embodiments, force exerted above the threshold results in an internal slippage of the rotation component mechanism. In some embodiments, shaft 705 of the rotation component 45 is coupled to the ventricular part 32 of, for example, FIG. 19, with the result that shaft 705 and ventricular part 32 rotate together. Optionally, coupling is through fork 70. In some embodiments, the rotation of shaft 705 is initiated by rotation of twisting control 710, for example, at the hands of a surgeon performing the deployment operation.

In some embodiments of the invention, coupling between shaft 705 and twist control 710 is mediated through twist safety spring 720, and twist adaptor 730. Twist safety spring 720 is fixedly connected to a part of twist control 710, and moves with it at the connected region. In some embodiments, twist control 710 has an interior lumen. Optionally, the connected region is on the wall of this interior lumen. In some embodiments, at least a portion of twist adaptor 730 occupies the interior lumen of twist control 710 along with twist safety spring 720. In some embodiments, twisting adaptor 730 is fixedly and/or fittingly connected to shaft 705, for example by glue and/or a pressure fit. In some embodiments, twisting adaptor 730 surrounds a portion of the length of shaft 705.

In some embodiments, at least a portion of twist adaptor 730 contacts an unfixed portion 724 of twist safety spring 720. Optionally, unfixed spring portion 724 presses toward twist adaptor 730 due to the elasticity of the spring. Optionally, the unfixed portion 724 is the free end of the spring.

At the region of contact, twist adaptor 730 further comprises a section of one or more détentes, for example, ratchet teeth, 740. Optionally, the section of ratchet teeth, 740 is curved. At least a part of unfixed spring portion 724 inserts in between at least one pair of teeth in the section of ratchet teeth 740, or optionally into the holding region of another détente structure such as a notch.

In some embodiments of the invention, when twisting control 710 is rotated, a force is transmitted to ratchet teeth section 740 through the contact with twist safety spring 720. If the forces acting to oppose the rotation of twist adaptor 730 are sufficiently small, then twist adaptor 730 also rotates. As a consequence, connected components including, for example, shaft 705, fork 70, and ventricular part 32, also rotate. During successful deployment, this is the rotation that brings the arms 34 into contact with valve chords 22, grasping them, and thereby producing tension which potentially assists in maintaining the position of the fully deployed implanted valve.

Figure 23A:
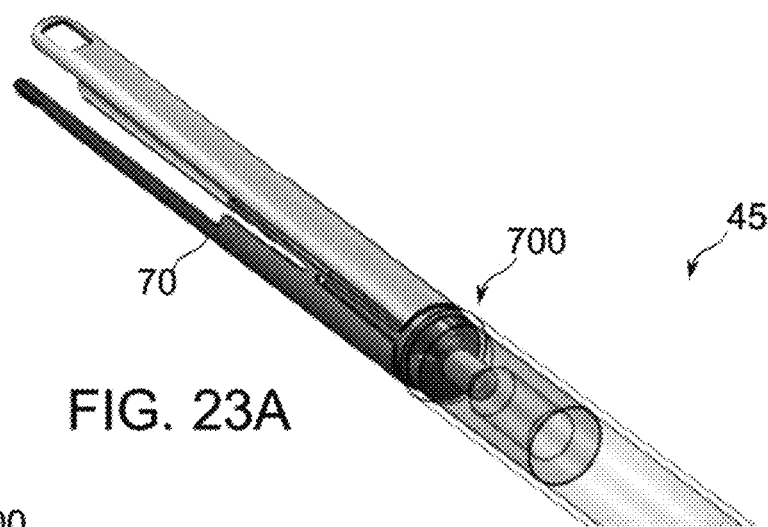
FIGS. 23A-23D are schematic sectional views showing a tissue safety mechanism comprised in a rotation component, in accordance with an exemplary embodiment of the invention.
Figure 23B:
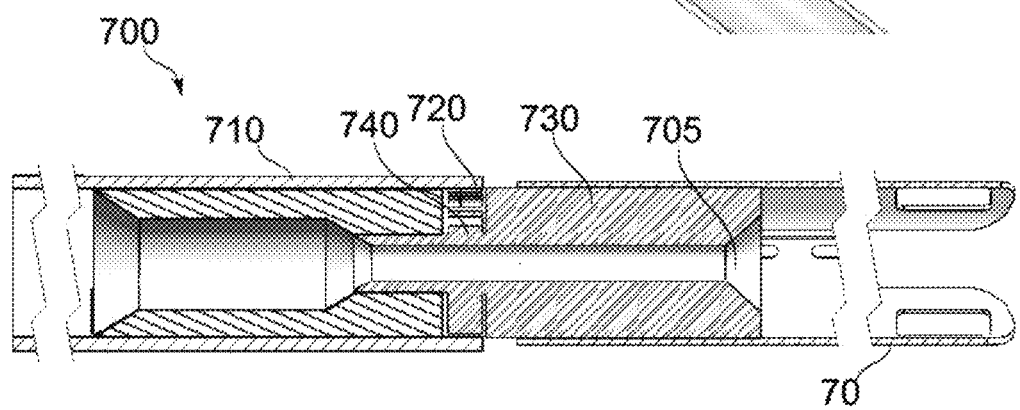
Figure 23C:
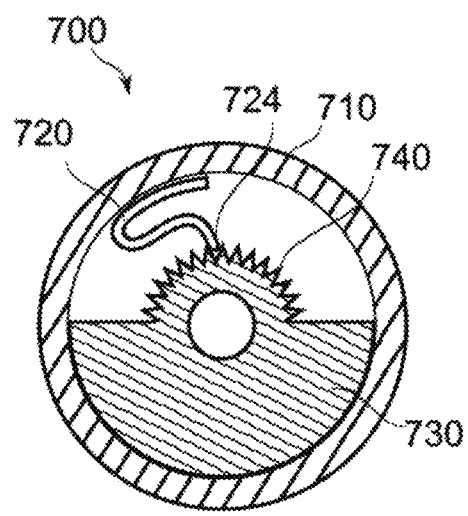
Figure 23D:
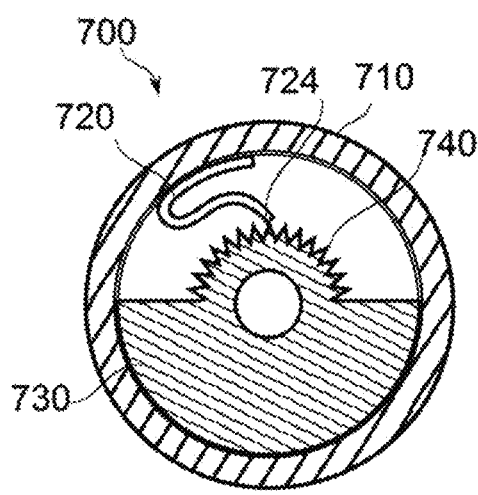

In some embodiments of the invention, as rotation continues, the opposing force acting back toward twist adaptor 730 increases, for example until a good contact is made between the leaflet and the wall of the valve. In some embodiments, if rotation continues, exerting force beyond a certain required threshold, the opposing force is sufficient to cause slippage at the détente mechanism. The stretching force intended may be, for example, 2 cNm, 5 cNm, 10 cNm, 15 cNm, or any value in between, or a greater or lesser value, as determined to be appropriate for the conditions of deployment. In some embodiments, ratchet teeth section 740 ceases to follow the movement of twist safety spring 720. Instead, unfixed portion 724 of the spring rises from between the teeth of ratchet teeth section 740 (FIG. 23D). When it has risen far enough, the teeth no longer restrain the spring, and the spring slips along, for example, to the next pair of teeth.

Optionally, this produces an audible click and/or tactile vibration. Optionally, ratchet teeth are set next to one another in series so that more than one slip position is provided.

Potentially, the sound and/or feel of the slipping spring serve as a warning to the surgeon that control force beyond the preset threshold has been supplied. Optionally, a stop is provided which is encountered during rotation at a preset angle corresponding to a target level of rotation. When the stop is encountered, additional rotation force is transmitted to the stop, and is not transmitted to elements of the catheter deployment system in proximity to the heart.

It should be noted that operation of the safety mechanism does not depend on all specifics of the above-described embodiment. For example, the insertion of the twist adaptor 730 into a lumen of the twist control 710 could be inverted so that the twist control 710 instead inserts into a lumen of the twist adaptor 730. Similarly, curved section of ratchet teeth could be convex, as shown, but could also be arranged along the inner wall of a lumen. The location of the twist safety spring attachment is optionally on an outer wall of an inner component. In some embodiments, the twist safety spring is replaced by another mechanism which holds a position within a détente with a calibrated force, for example, a spring-loaded probe tip. For embodiments which include this safety mechanism, these and other variations in structural detail are contemplated as potential embodiments of the invention.

Ventricle Part Release

Figure 20:
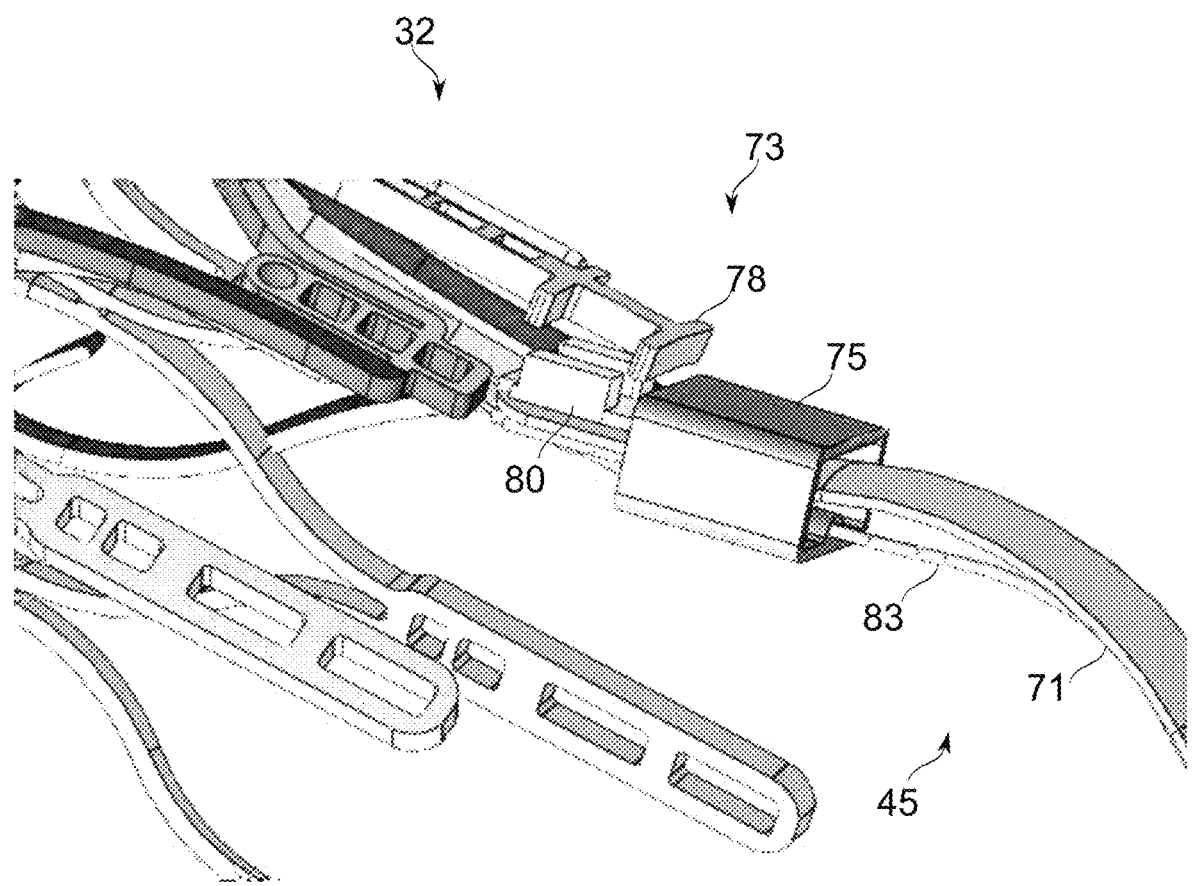
FIG. 20 is a schematic perspective illustration of an exemplary prong of a fork which is part of catheter deployment system, in accordance with an exemplary embodiment of the invention.

Reference is now made to FIG. 20, which is a schematic perspective illustration of an exemplary prong 71 of fork 70, including portions of the region of contact 73 with the ventricular part 32, according to an exemplary embodiment of the invention. In order to complete surgical implantation of the prosthetic mitral valve, it is necessary to detach the catheter deployment system 50 from the implanted valve 965.

Fork 70 is a portion of rotation component 45. In the configuration shown, the fork 70 and ventricular part 32 are undergoing detachment after deployment.

In some embodiments of the invention, locking sleeve 75 covers the region of contact 73 during deployment, keeping ventricular part locking element 78 enclosed together with prong locking element 80. While enclosed, the two locking elements 78, 80 are unable to disengage.

In some embodiments, command wire 83 is connected to locking sleeve 75. When the command wire 83 is retracted by an operation on the distal handle of the catheter deployment system, the locking sleeve 75 retracts along with it. This removes the enclosure keeping the locking elements 78, 80 together. Optionally, fork prong 71 is disposed to return radially to the center axis once freed, for example, because of its elastic properties. Optionally, a slight restraining force exerted by fork prong 71 is overcome at the time of release, and ventricular part 32 undergoes sufficient additional expansion to break the locking contact. Optionally, the locking contact is broken when the proximal end 51 is returned to position in preparation for withdrawing the catheter deployment system.

Figure 21A:
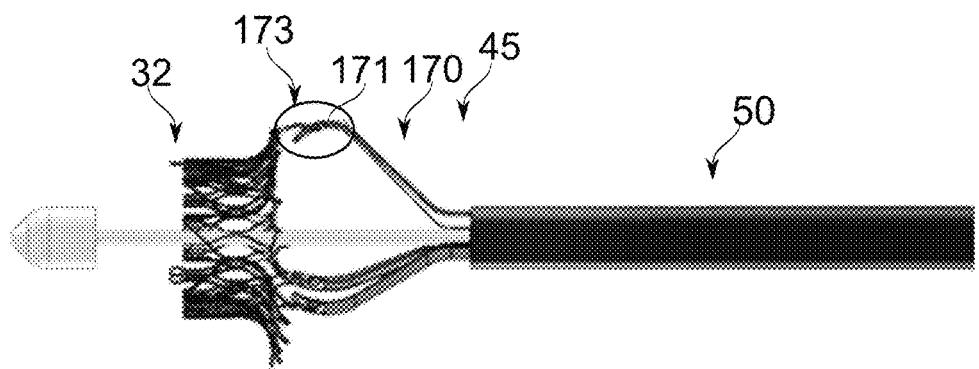
FIGS. 21A-21B are schematic perspective illustrations of an exemplary prong of a fork, which is part of a catheter deployment system, in accordance with an exemplary embodiment of the invention.
Figure 21B:
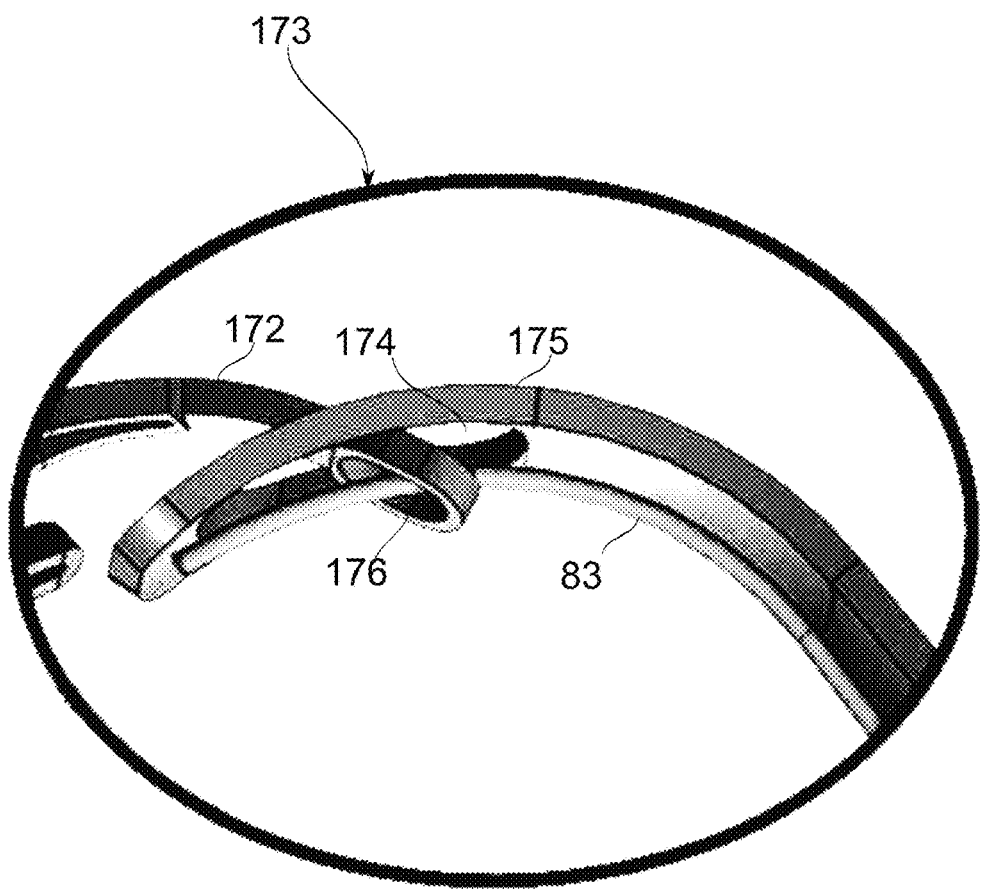

Reference is now made to FIGS. 21A-21B, which are schematic perspective illustrations of an exemplary prong 171 of fork 170, including portions of the region of contact 173 with the ventricular part 32, according to an exemplary embodiment of the invention. In some embodiments, fork 170 is a portion of rotation component 45, and is an alternative embodiment of the functions, including rotation and detachment performed by fork 70. In the configuration shown, the fork 170 and ventricular part 32 are still attached after deployment.

In some embodiments of the invention, ventricular part locking element 172 comprises an extension which inserts through an aperture 174 in prong locking element 175. Command wire 83 in turn passes through an aperture 176 in ventricular part locking element 172, on the side of locking element 172 which has passed through the aperture. The two locking elements are thereby held in association.

When the command wire 83 is retracted by an operation on the distal handle of the catheter deployment system 50, it is removed from ventricular part locking element aperture 176. The locking elements 172, 175, are then free to separate. Separation itself occurs when the elements move apart, for example, due to one of the mechanisms discussed in relation to locking elements 78, 80.

Exemplary Fixation Mechanisms

Figure 14:
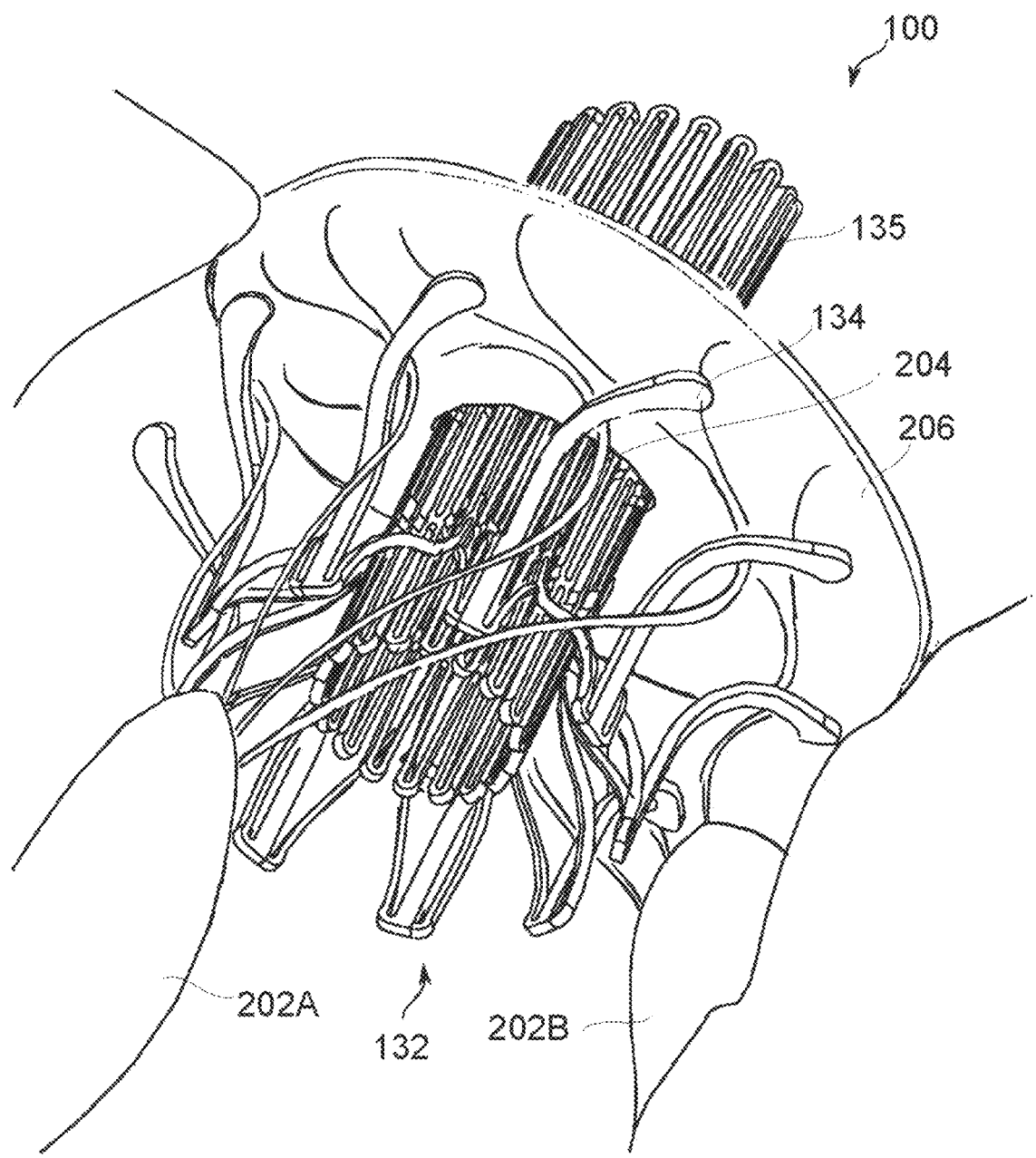
FIG. 14 is a schematic of the prosthetic mitral valve partially deployed in the native mitral valve annulus in an isometric view from the left ventricle, in accordance with an exemplary embodiment of the invention.

Reference is now made to FIG. 14, which is a schematic diagram of exemplary valve 100 partially deployed in the native mitral valve annulus, in an isometric view from the left ventricle, according to an exemplary embodiment of the invention.

Ventricle part 132 is in the expanded state. In an exemplary embodiment, valve 100 has been rotated so that arms 134 grab chords 204. Optionally, the rotation is sufficient to apply a rotational torque and/or tension to chords 204 that is strong enough to move mitral leaflets 206 around atrial part 135.

In an exemplary embodiment of the invention, the rotation applied to valve 100 is, for example, about 10 degrees, about 20 degrees, about 30 degrees, about 60 degrees, about 120 degrees, or other smaller, intermediate or larger degrees of rotation. Optionally, the rotation is related to the size of the mitral valve annulus. For example, for an annulus with a relatively larger diameter (for example, dilated annulus, in an adult as opposed to a child) relatively more rotation is used than for a smaller diameter annulus. Optionally, the rotation is determined considering the size of the heart, the size of the valve, the slack of the chords, and/or the desired force of sealing.

Figure 15A:
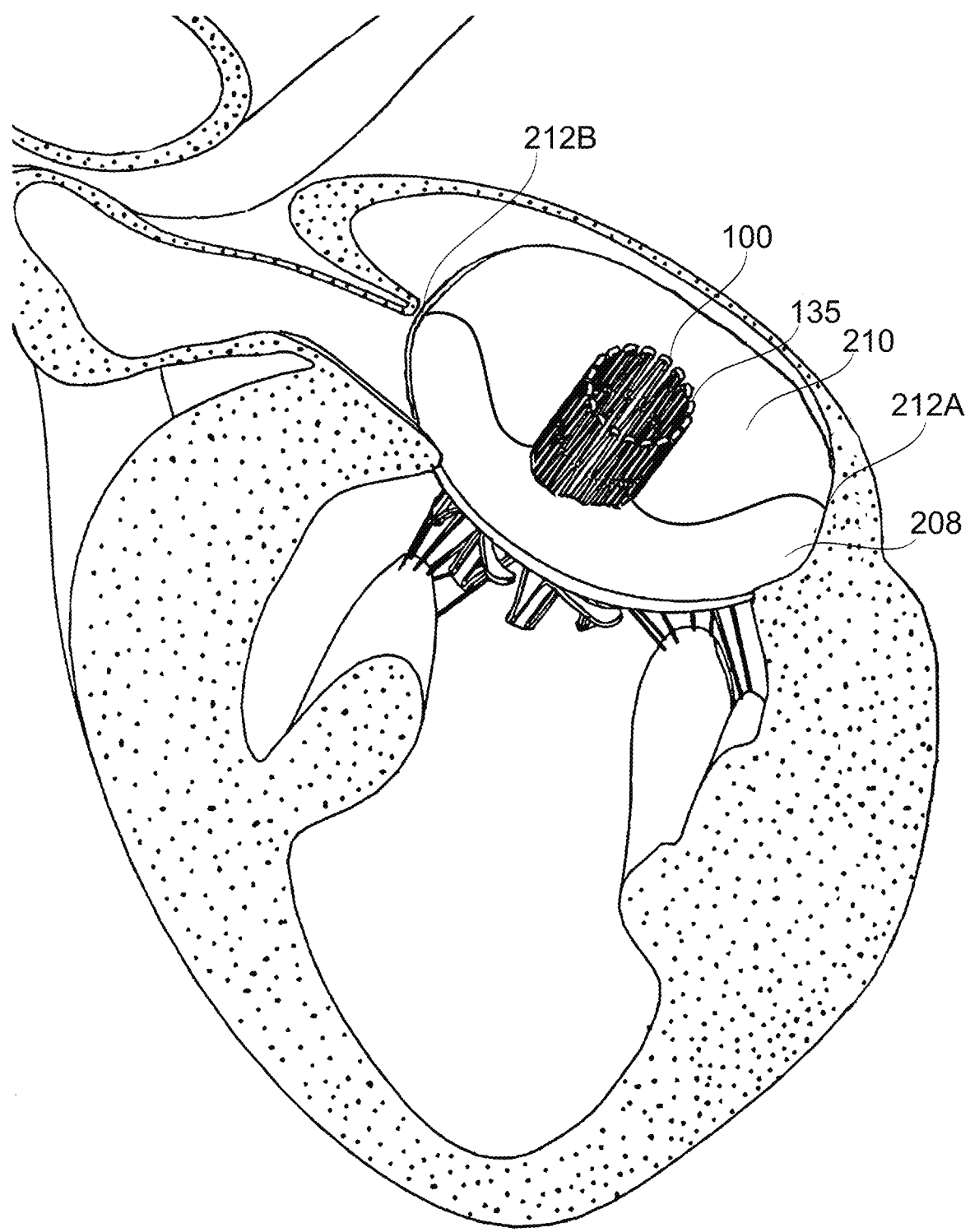
FIGS. 15A-15D are schematics of the prosthetic mitral valve partially deployed in the native mitral valve annulus, in an isometric view from the left atrium, in accordance with an exemplary embodiment of the invention.

Reference is now made to FIG. 15A, which is a schematic diagram of exemplary valve 100 as in the partially deployed state of FIG. 14, in an isometric view from the left atrium, according to an exemplary embodiment of the invention. In an exemplary embodiment, the rotation applied to valve 100 is sufficient to bring anterior leaflet 208 and posterior leaflet 210 in close contact with atrial part 135. Optionally, the twisting is sufficient to overlap an edge of leaflet 208 and/or 210 with the surface of the opposite leaflet. Optionally, leaflets 208 and 210 form a seal against each other and/or together with annular part 135 so that regurgitation from the left ventricle to the left atrium during systole is not clinically significant.

In an exemplary embodiment of the invention, the twisting motion of valve 100 is sufficient to seal commissural points 212A and 212B (at junction of anterior leaflet 208 and posterior leaflet 206 at the surrounding fibrous ring). Optionally, the edge of leaflet 208 and/or 206 near commissural point 212A or 212B overlaps the surface of the opposite leaflet. Potentially, the sealing at the commissural points is good enough so that regurgitation is not clinically significant.

Figure 15B:
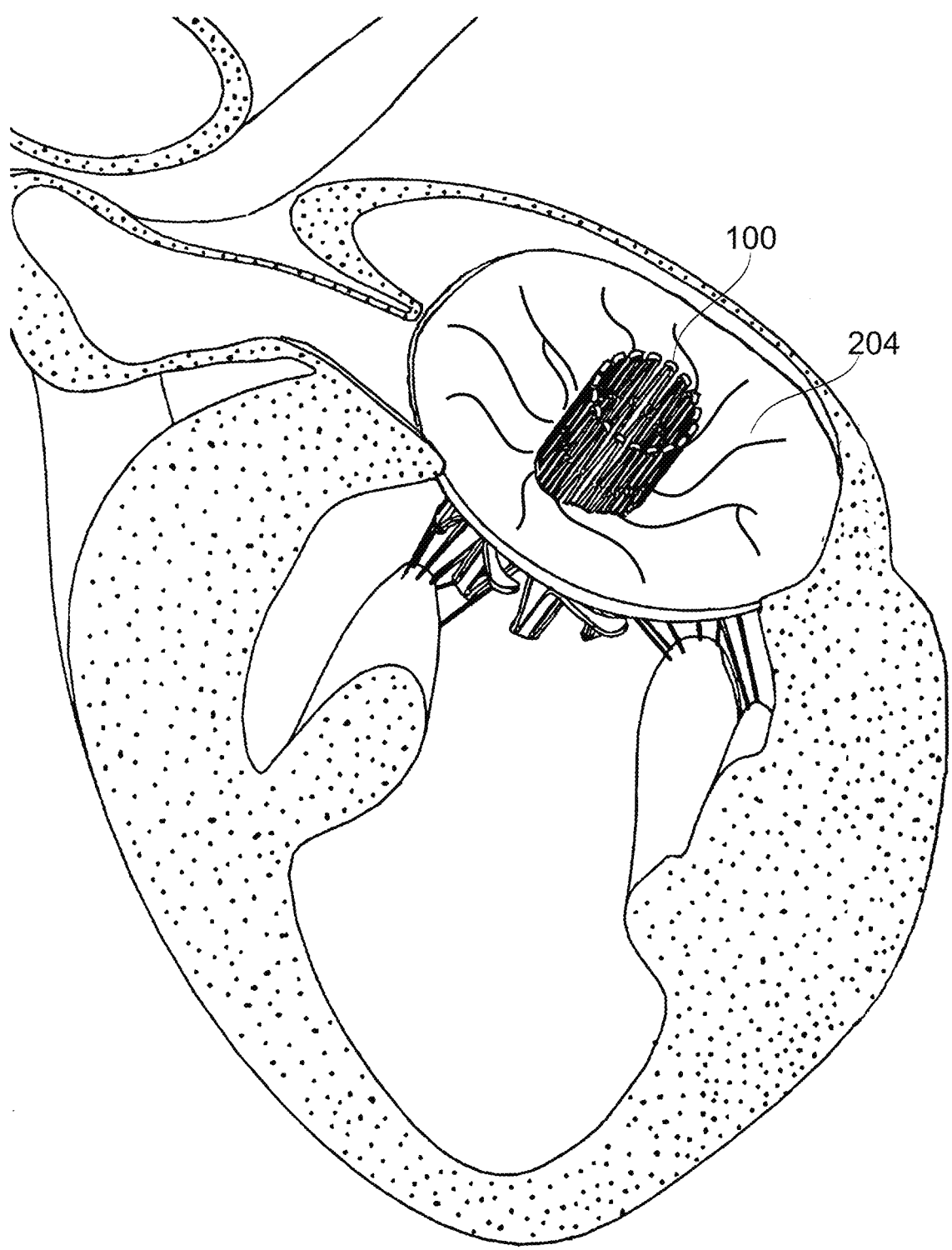

Reference is now made to FIG. 15B, which is a schematic diagram showing the configuration of chords 204 in FIG. 15A due to the grabbing by arms 134 and the twisting motion (for example, as would be viewed if leaflets 208 and 210 were transparent), according to an exemplary embodiment of the invention. Optionally, arms 134 grab chords 204 and valve 100 is turned sufficiently to form a spiral formation of chords 204 around valve 100.

Figure 15C:
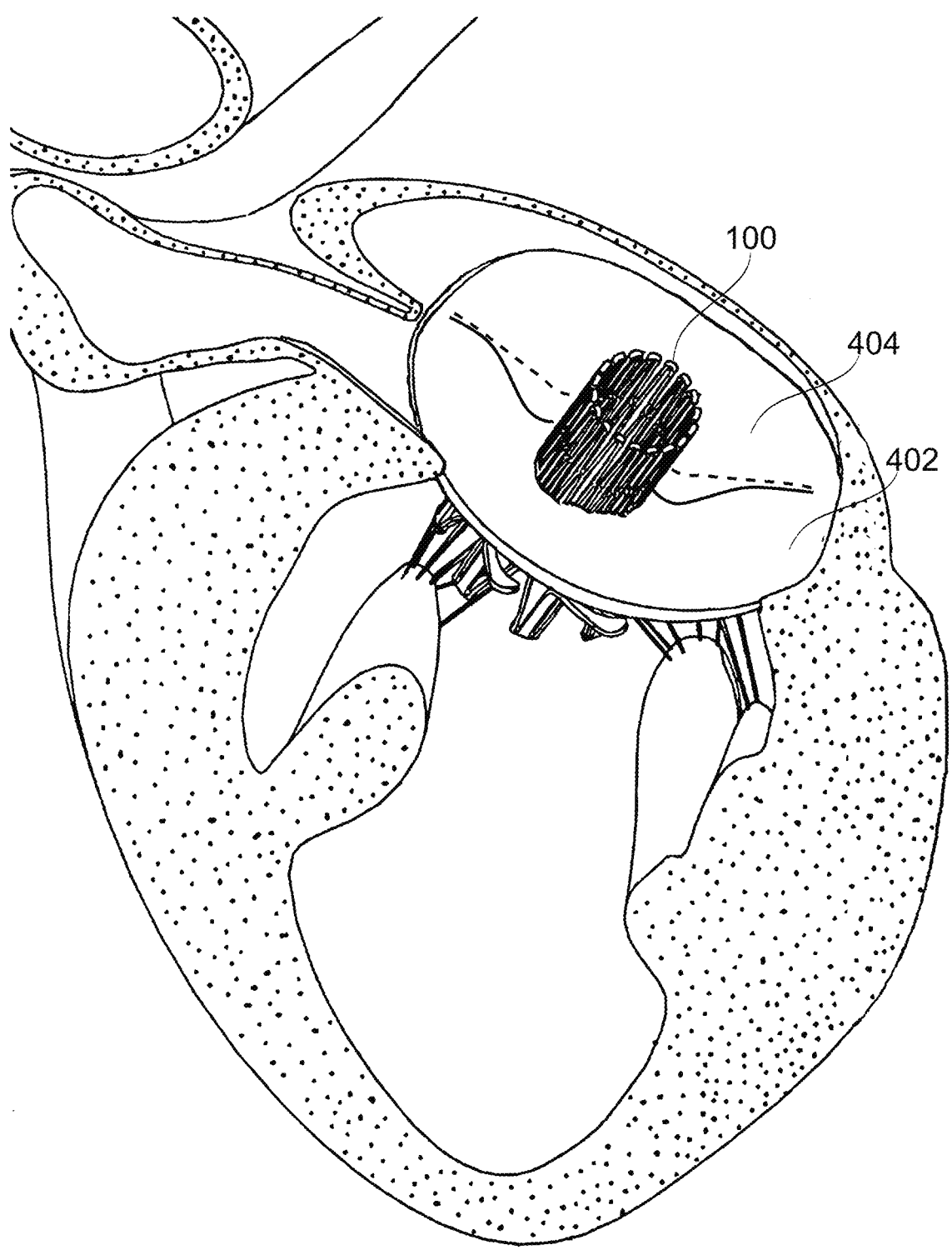

FIG. 15C is a schematic diagram of FIG. 15A, showing the overlap of posterior and anterior leaflets over each other due to the twisting motion, in accordance with an exemplary embodiment of the invention. In an exemplary embodiment, anterior leaflet 402 overlaps posterior leaflet 404. Alternatively, posterior leaflet 404 overlaps anterior leaflet 402. Alternatively, some of the posterior leaflet 404 overlaps some of anterior leaflet 402 and some of anterior leaflet 402 overlaps some of posterior leaflet 404.

Figure 15D:
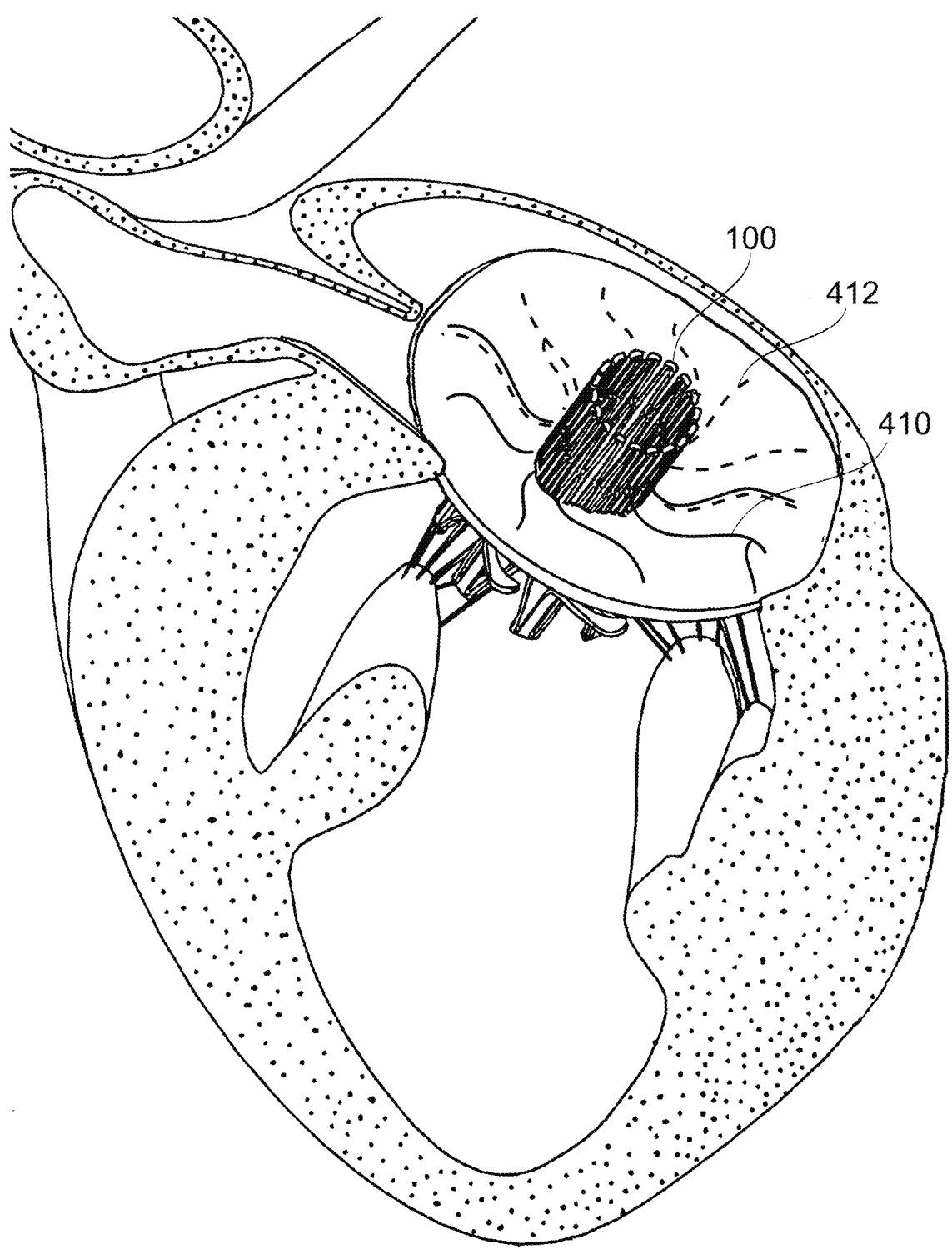

FIG. 15D is a schematic diagram of FIG. 15A, showing another representation of the overlap of posterior and anterior leaflets over themselves due to the twisting motion, in accordance with an exemplary embodiment of the invention. In an exemplary embodiment anterior leaflet overlaps with itself (overlapping lines shown as 410), for example, like an accordion. Optionally or additionally, the posterior leaflet overlaps with itself (overlapping lines shown as 412).

In some embodiments, after native chords 22 and leaflets are engaged with arms, a portion of a distal end of the catheter deployment system (not depicted) is pulled proximally and/or pushed distally so that an atrial-part placement component expands to a properly deployed position inside left atrium 25.

Figure 16:
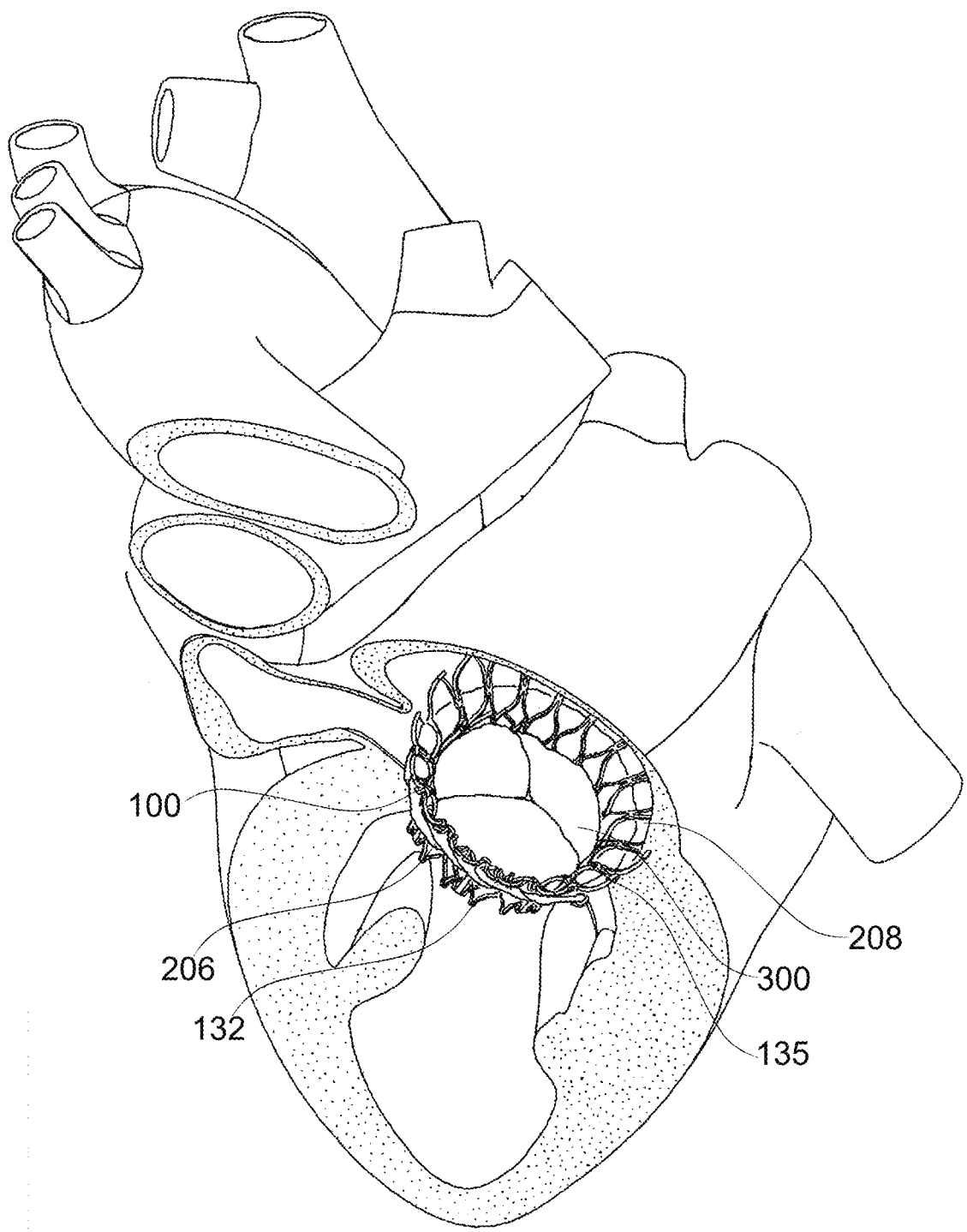
FIG. 16 is a schematic of the deployed prosthetic mitral valve, in accordance with an exemplary embodiment of the invention.

FIG. 16 illustrates valve 100 in the fully deployed state inside the native mitral valve annulus, in an isometric view from the left atrium.

In an exemplary embodiment of the invention, expansion of the annular part 135 traps and/or clamps leaflets 206 and/or 208 between annular part 135 and ventricular part 132. In some embodiments, the compression forces applied against leaflets 206 and/or 208 between atrial part 135 and/or ventricular part 132 are sufficient to maintain the twisted valve 100 state. For example, arms 134 grab chords 204 and apply tension to close leaflets 206 and/or 208 around prosthetic valve 100. In some embodiments, some spring back is allowed.

Figure 22A:
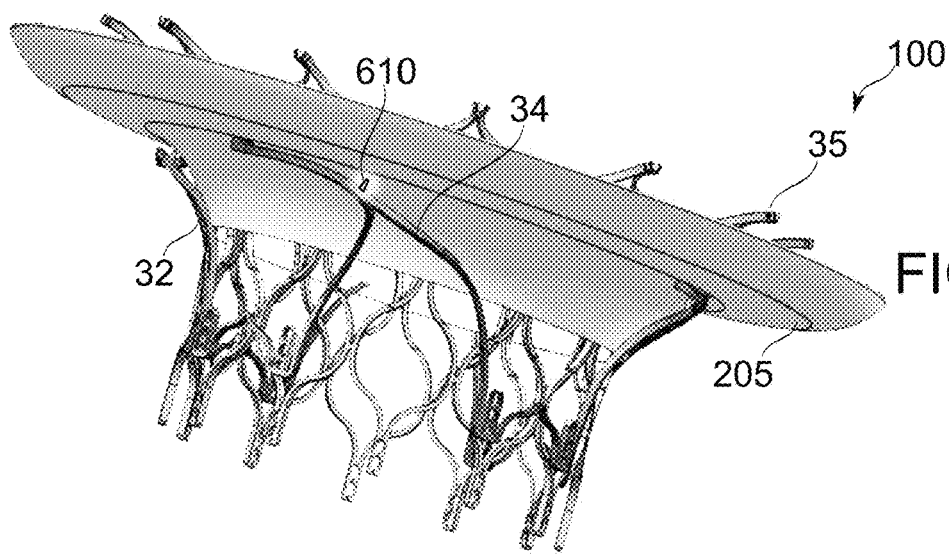
FIGS. 22A-22C are schematic perspective views showing exemplary barbed projections acting as attachment elements for the ventricular part and atrial part of a prosthetic atrial valve, in accordance with an exemplary embodiment of the invention.
Figure 22B:
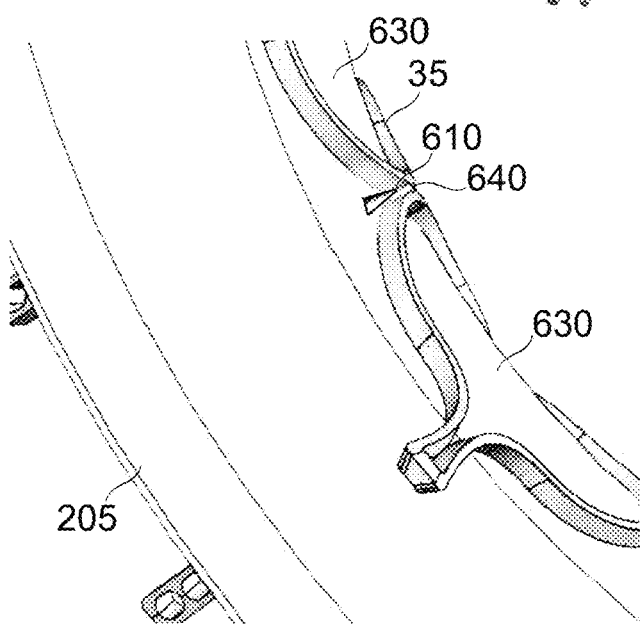
Figure 22C:
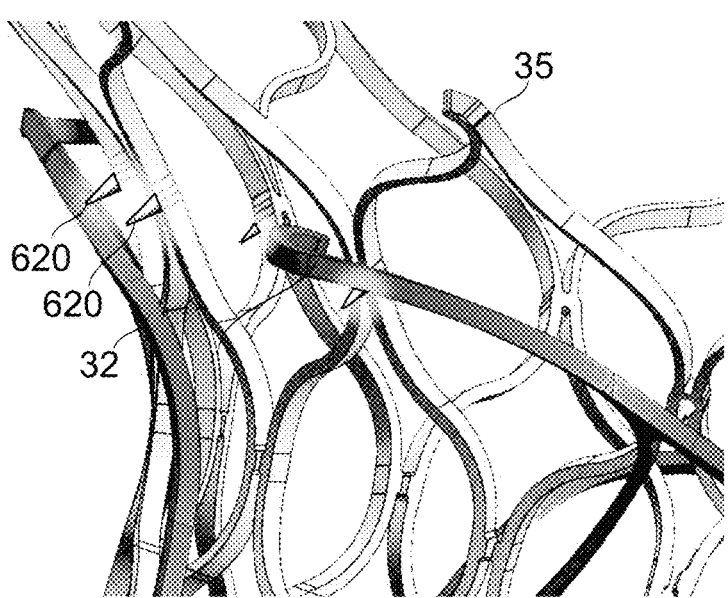

Reference is now made to FIGS. 22A-22C, which are schematic perspective views showing exemplary barbed projections 610, 620 acting as attachment elements for the ventricular part 32 and atrial part 35 of the valve 100, according to an exemplary embodiment of the invention. Potentially, barbed projections offer an advantage for locking leaflets into place, and/or locking frame parts to each other.

In an exemplary embodiment of the invention, valve 100 comprises one or more piercing attachment elements 610, 620 which are projections adapted to pierce the leaflets. In some embodiments of the invention, piercing elements 610, 620 serve to help retain captured native valve leaflets 205.

In FIG. 22A, piercing element 610 is shown projecting upward from an arm 34 of ventricular part 32 and penetrating into a schematic representation of a native valve leaflet 205. FIG. 22B shows the obverse side of the leaflet, to which ventricular part piercing element 610 has penetrated. By penetrating the leaflet, piercing element 610 provides additional anchoring stability to the prosthetic mitral valve which has also captured the leaflet between the atrial and ventricular parts.

Optionally, the placement of piercing elements is chosen so that they at least partially interlock the atrial and ventricular parts. For example, piercing element 610 in FIG. 22B is shown penetrating near to the crux 640 of two adjoining fenestrations 630 of the atrial part 32. This position potentially serves to restrain relative upward movement of the atrial part 35 compared to the ventricular part 32.

In FIG. 22C, the tips of atrial piercing elements 620 are shown without a leaflet, projecting from atrial part 35 downward. This illustrates, for example, that the same mechanism of barbed projections for stabilization is adaptable for use on both parts of the prosthetic mitral valve anchoring components.

Alternatively or additionally, the piercing elements 610, 620 are adapted to pierce surrounding tissues, for example, the fibrous ring and/or the atrium wall. Potentially, the piercing elements serve to anchor the prosthetic mitral valve in the supporting tissue. Not necessarily limiting examples of piercing elements include: barbs, hooks, and/or needles. Optionally, atrial part 135 comprises the piercing elements. Alternatively or additionally, ventricular part 132 comprises the piercing elements. Optionally or additionally, the attachment elements 610, 620 pierce into the leaflets 205 and/or tissues of and surrounding the native mitral valve aperture upon expansion. Potentially, the piercing elements help maintain the position of valve 100.

In an exemplary embodiment of the invention, prosthetic leaflets 300 start to function upon deployment of valve 100. A potential advantage is that the heart does not need to be stopped, and can continue beating during the procedure.

Completion of Deployment

Figure 11:
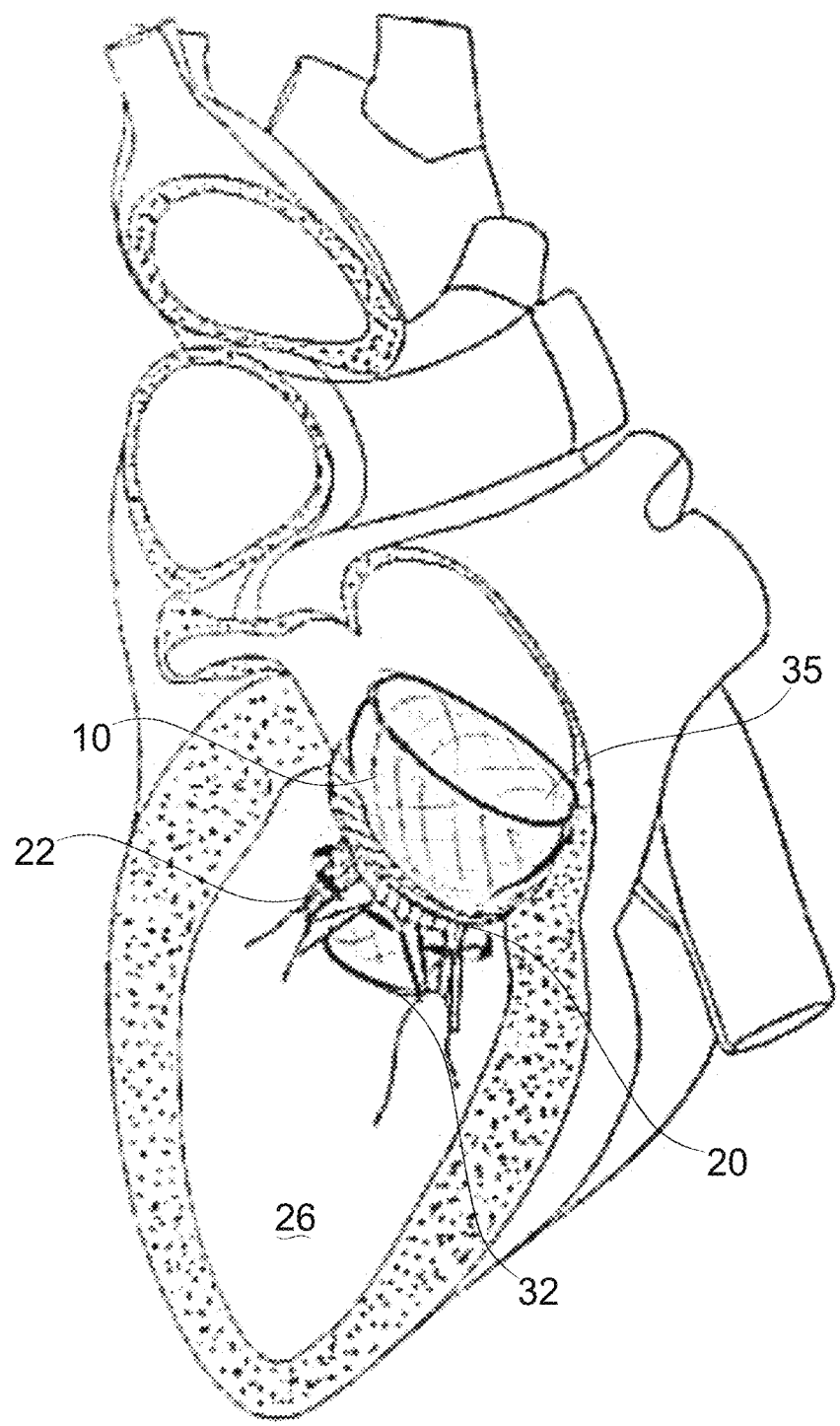
FIG. 11 schematically depicts a deployed prosthetic mitral valve, in accordance with an exemplary embodiment of the invention.

After deployment and detachment from the prosthetic mitral heart valve, the catheter deployment system 50 is withdrawn from heart 970. Optionally, the incision is closed 975 in the usual way; optionally the operation is ended 980 in the usual way. As illustrated in FIG. 11, prosthetic mitral valve 10 is left deployed in the heart, surrounding native mitral valve annulus 20, grasping chords 23 and leaflets, and securing tissue surrounding annulus from above with atrial part 35 and from below with ventricular part 32.

Once the operation is complete, deployed prosthetic mitral valve functions as a native mitral valve. In some embodiments of the invention, the mechanical properties of the atrial part and ventricular part allow dynamic conformation to the shape and size of mitral valve annulus and the atrial walls, as these change during the beating of the heart. For example, the parts adopt a smaller configuration when the mitral valve annulus compresses, and spring back to a larger-sized configuration when the mitral valve annulus relaxes.

Figure 24A:
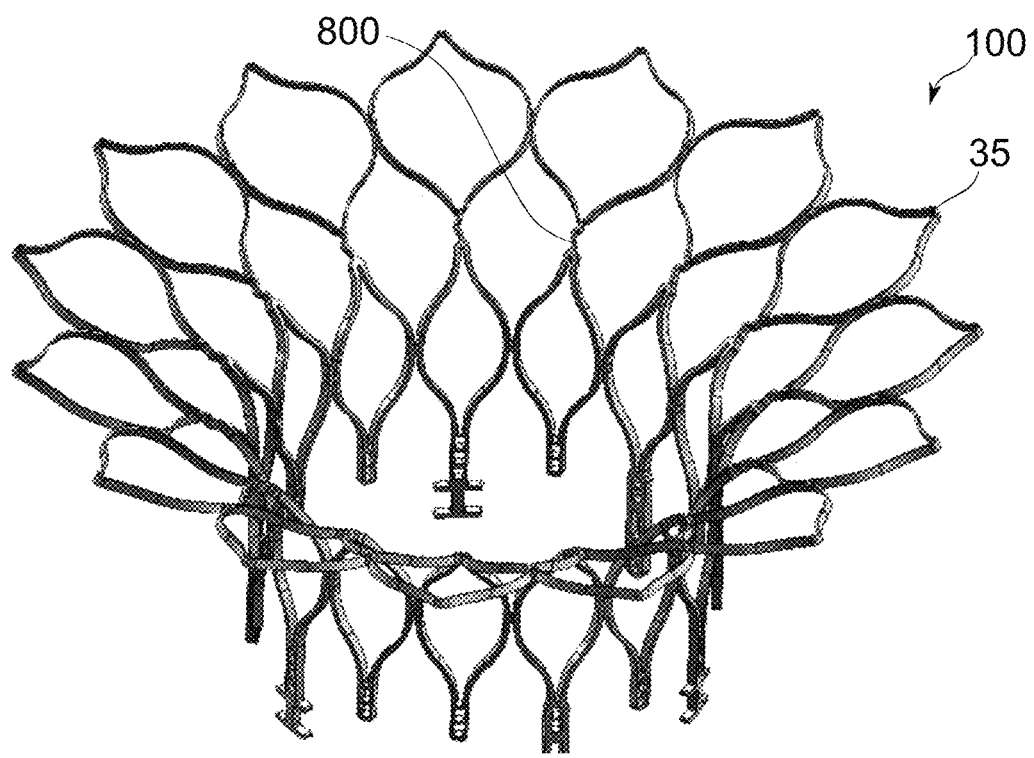
FIGS. 24A-24B are schematic perspective views showing a spring adaptor section portion of an atrial part, in accordance with an exemplary embodiment of the invention.
Figure 24B:
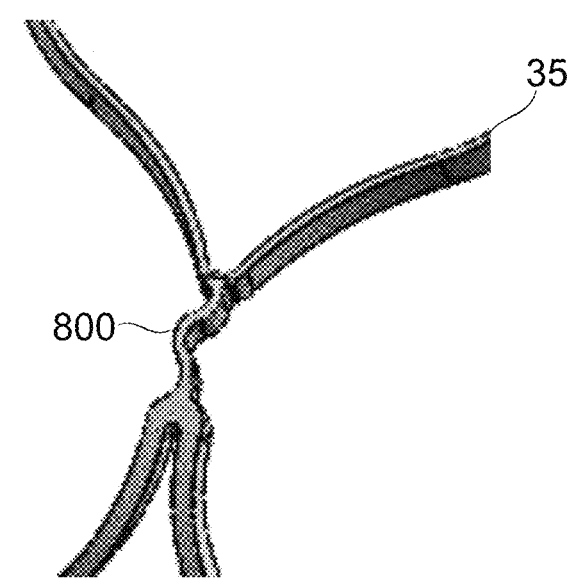

Reference is now made to FIGS. 24A-24B, which are schematic perspective views showing spring adaptor section 800, comprised in atrial part 35, according to an exemplary embodiment of the invention. Spring adaptor section 800 illustrates a design element which other embodiments of the invention having frames with different-shaped members can also incorporate. For example, embodiments of the atrial part of FIG. 5A are adaptable to have a spring adaptor section inserted at the commissural points between any two of the three sinusoidal levels shown.

In some embodiments of the invention, one or more spring adaptor sections 800 are provided, for example, at intervals around a circumference of atrial part 35 of prosthetic mitral valve 100. Upon a receiving force, for example, due to pressing of an atrial wall on an outer circumference of atrial part 35, spring adaptor section 800 buckles and compresses. Buckling is promoted, for example, by manufacturing the section with a preset bend, and/or a thinner region along its length. Potentially, this reduces further buildup of forces between the atrial wall and atrial part 35. Potentially, this allows the atrial wall to move more nearly according to its natural cycle of motions. Potentially, when forces on atrial part 35 again relax, the restorative force of spring adaptor section 800 extends the spring again. Potentially, this helps maintain a holding contact that assists in maintaining the position of the prosthetic mitral valve throughout the heartbeat cycle.

Exemplary Deployment Options

In some embodiments discussed, for example, with reference to FIGS. 2A-7B, and FIGS. 13A-13F, the atrial part and ventricular part are self-expanding from a delivery configuration to a deployed configuration. In some embodiments, the parts of a prosthetic mitral valve as described herein are expandable from a delivery configuration to a deployed configuration by application of a radially outwards force to an inner surface thereof.

Optionally, during the operation in which the prosthetic mitral valve is deployed, the beating of the heart in which the prosthetic mitral valve is deployed is not stopped. With this option, a TEE probe, for example, is placed and used in the usual way to observe the left ventricular long axis of the heart throughout the operation, for guiding positioning and verifying results.

Optionally, access to the left ventricular apex of the heart is gained under general anesthesia through a left anterolateral mini-thoracotomoy in the fifth intercostal space, with horizontal opening of the pericardium and placement of stay sutures for exposure. In an exemplary sequence of steps for gaining access to the heart, a retractor is placed, exposing the heart apex. Two rows of 3-0 polypropylene pledgeted felt purse string sutures are placed around the left ventricular apex creating a 3-4 cm diameter area exposed for access. A 4000 U heparin bolus is administered intravenously.

In some embodiments of the method for valve deployment described above, a crimping tool and a video camera are advanced through the delivery lumen of the catheter deployment system to assist in deploying a prosthetic mitral valve. In some embodiments, crimping tools, video cameras, and/or other devices for assisting in deploying a prosthetic mitral valve as described herein are brought to a desired location through one or more different access routes. For example, an assisting device may be brought through the vasculature and into the heart through the aorta using a suitable catheter.

In some of the embodiments described above, a prosthetic mitral valve includes a valve mechanism that is not subject to prolapse of leaflets into the left atrium. Prolapse may be prevented, for example, to the particular construction of the valve mechanism and/or the presence of a prolapse-preventing component.

Some of the embodiments described above are also applicable to deployment in place of a native mammalian tricuspid valve, with suitable selection of component dimensions. Such a tricuspid valve may be implanted alone; or, for example, some embodiments described herein may be used to provide both a prosthetic mitral valve and a separate prosthetic tricuspid valve in the same heart.

In some of the embodiments described above, the teachings herein are implemented to provide a prosthetic heart valve that is a prosthetic mitral valve, having features rendering the prosthetic heart valve exceptionally useful for overcoming challenges in the field of prosthetic mitral valve deployment.

Any suitable combination of materials and methods of manufacture may be used in implementing the teachings herein. For example, a person having ordinary skill in the art of prosthetic cardiac valves is able to select suitable materials and methods of manufacture. Selection is possible, for example, with reference to commercially-available prosthetic cardiac valves.

The nature and dimensions of the various parts and components of the prosthetic mitral valves and the catheter deployment systems as described herein can be determined by a person having ordinary skill in the art, making reference to the embodiments described herein, and/or by making reference, without undue experimentation, to commercially-available transapical delivery devices and accompanying prosthetic cardiac valves, especially prosthetic mitral valves, for example the Perimount™ Magna prosthetic mitral heart valve by Edwards Lifesciences LLC (Irvine, California, USA).

As used herein the term "about" refers to 10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A method for use with a prosthetic valve that is configured to be deployed within a native atrio-ventricular valve of a heart of a mammalian subject, the native atrio-ventricular valve including a valve annulus, native valve leaflets, and ventricular structures including chords, papillary muscles, and ventricular walls, the method comprising:
   placing a valve frame within the subject's heart, the valve frame including:
      a valve frame body that is configured to support the prosthetic valve within the native atrio-ventricular valve, and that includes an atrial portion and a ventricular portion, and
      at least one arm that is configured to extend from the ventricular portion of the valve frame;
   subsequently, deploying the at least one arm among the chords of the native atrio-ventricular valve;
   subsequently, rotating at least a portion of the valve frame, in a direction in which an interior of the arm faces, such as to modify shapes of the native valve leaflets and the ventricular structures, by recruiting and deflecting at least a portion of the chords; and
   subsequently, causing the frame body of the valve frame to radially expand, such as to hold the native valve leaflets and the ventricular structures at least partially in the modified shapes.

2. The method according to claim 1, wherein deploying the at least one arm among the chords of the native atrio-ventricular valve comprises deploying the at least one arm among the chords of the native atrio-ventricular valve such that the arm defines a curving inner surface that curves, as a radial distance of the arm from the ventricular portion increases, from a relatively more radial orientation of the curved surface to a relatively more circumferential orientation of the curved surface.

3. The method according to claim 1, further comprising locking the deployed arm into position.

4. The method according to claim 1, wherein deploying the at least one arm among the chords of the native atrio-ventricular valve comprises deploying the arm such that a chord receiving surface of the arm defines a slope that guides chords into a chord grasping region located between the arm and the ventricular portion, during the rotation of portion of the valve frame.

5. The method according to claim 1, wherein causing the frame body of the valve frame to radially expand, such as to hold the native valve leaflets and the ventricular structures at least partially in the modified shapes comprises preventing blood flow between the native valve leaflets and the valve frame, at least in the direction passing from a ventricle to an atrium of the heart.

6. The method according to claim 1, wherein deploying the at least one arm among the chords of the native atrio-ventricular valve comprises deploying the at least one arm among the chords of the native atrio-ventricular valve, even when the portion of the valve frame from which the at least one arm extends is in a radially-compressed state.

7. The method according to claim 1, further comprising preventing the portion of the chords that are recruited by the arm from exiting the arm, using a protruding member shaped to protrude from the arm.

8. The method according to claim 1, wherein the native atrio-ventricular valve includes a native mitral valve, and placing the valve frame within the patient's heart comprises placing within a left heart of the patient a valve frame that is configured to support the prosthetic valve within the native mitral valve.

9. The method according to claim 1, wherein causing the frame body of the valve frame to radially expand, such as to hold the native valve leaflets and the ventricular structures at least partially in the modified shapes comprises using the at least one arm to hold the native valve leaflets and the ventricular structures at least partially in the modified shapes.

10. The method according to claim 1, wherein causing the frame body of the valve frame to radially expand, such as to hold the native valve leaflets and the ventricular structures at least partially in the modified shapes comprises holding the native valve leaflets between the atrial portion of the valve frame and the at least one arm.

11. The method according to claim 1, wherein causing the frame body of the valve frame to radially expand, such as to hold the native valve leaflets and the ventricular structures at least partially in the modified shapes comprises causing a cylindrical portion of the valve frame that extends through an annular level of the native atrio-ventricular valve to radially expand toward the at least one arm, such as to hold the native valve leaflets and the ventricular structures at least partially in the modified shapes.

12. The method according to claim 1, wherein:
   rotating at least the portion of the valve frame comprises twisting the native valve leaflets, such that the native valve leaflets are shaped into overlapping configurations with respect to each other, and
   causing the frame body of the valve frame to radially expand comprises holding the native valve leaflets in the overlapping configurations with respect to each other.

13. The method according to claim 12, wherein twisting the native valve leaflets, such that the native valve leaflets are shaped into overlapping configurations with respect to each other comprises sealing commissures between the native valve leaflets by twisting the native valve leaflets into the overlapping configurations with respect to each other.

14. The method according to claim 1, wherein deploying the at least one arm among the chords of the native atrio-ventricular valve comprises extending the arm radially to a distance sufficient to engage primary and secondary chords of the native atrio-ventricular valve and rotating at least a portion of the valve frame, in a direction in which an interior of the arm faces comprises recruiting and deflecting at least a portion of the primary and secondary chords of the native atrio-ventricular valve.

15. The method according to claim 14, wherein deploying the at least one arm among the chords of the native atrio-ventricular valve comprises extending the arm radially to a distance sufficient to engage primary, secondary, and tertiary chords of the native atrio-ventricular valve and rotating at least a portion of the valve frame, in a direction in which an interior of the arm faces comprises recruiting and deflecting at least a portion of the primary, secondary, and tertiary chords of the native atrio-ventricular valve.

16. An apparatus for use with a prosthetic valve that is configured to be deployed within a native atrio-ventricular valve of a heart of a mammalian subject, the native atrio-ventricular valve including a valve annulus, native valve leaflets, and ventricular structures including chords and papillary muscles, the apparatus comprising:
- a valve frame configured to support the prosthetic valve within the native atrio-ventricular valve, the valve frame comprising:
  - a frame body comprising:
    - an atrial portion configured to be positioned such that, when the valve frame is deployed, at least a portion of the atrial portion is disposed on an atrial side of the native atrio-ventricular valve; and
    - a ventricular portion configured to be positioned such that, when the valve frame is deployed, at least a portion of the ventricular portion is disposed within a ventricle of the subject; and
  - at least one arm configured to extend from the ventricular portion of the frame body; and
- a delivery device configured to:
  - deliver the valve frame to the native atrio-ventricular valve;
  - subsequently, deploy the at least one arm among the chords of the native atrio-ventricular valve;
  - subsequently, rotate at least a portion of the valve frame, in a direction in which an interior of the arm faces, such as to modify shapes of the native valve leaflets and the ventricular structures, by recruiting and deflecting at least a portion of the chords; and
  - subsequently, cause the frame body of the valve frame to radially expand, such as to hold the native valve leaflets and the ventricular structures at least partially in the modified shapes.

17. The apparatus according to claim 16, wherein:
the ventricular portion of the valve frame has radially-compressed and radially-expanded states; and
the at least one arm is configured to become deployed among the chords of the native atrio-ventricular valve, even when the ventricular portion of the valve frame is in its radially-compressed state.

18. The apparatus according to claim 16, wherein the valve frame comprises a protruding member shaped to protrude from the at least one arm, and configured to bar the portion of the chords that are recruited by the arm from exiting the at least one arm.

19. The apparatus according to claim 16, wherein the native atrio-ventricular valve includes a mitral valve, and the valve frame is configured to support the prosthetic valve within the native mitral valve.

20. The apparatus according to claim 16, wherein the valve frame is configured to hold the native valve leaflets and the ventricular structures at least partially in the modified shapes at least partially by the at least one arm holding the chords in a twisted configuration around the valve frame.

21. The apparatus according to claim 16, wherein the valve frame is configured to hold the native valve leaflets and the ventricular structures at least partially in the modified shapes at least partially by the atrial portion of the valve frame radially expanding against the at least one arm, such as to hold the native valve leaflets between the atrial portion of the valve frame and the at least one arm.

22. The apparatus according to claim 21, wherein the atrial portion of the valve frame comprises a cylindrical portion that is configured to extend through an annular level of the native atrio-ventricular valve, and wherein the cylindrical portion of the atrial portion of the valve frame is configured to radially expand toward the at least one arm, such as to hold the native valve leaflets between the cylindrical portion of atrial portion of the valve frame and the at least one arm.

23. The apparatus according to claim 16, wherein:
the at least one arm is configured to twist the native valve leaflets, such that the native valve leaflets are shaped into overlapping configurations with respect to each other,
the valve frame is configured to seal a space between the native atrio-ventricular valve and the prosthetic valve by holding the native valve leaflets in the overlapping configurations with respect to each other.

24. The apparatus according to claim 23, wherein the arm is configured to seal commissures between the native valve leaflets by the twisting the native valve leaflets into the overlapping configurations with respect to each other.

25. The apparatus according to claim 16, wherein the at least one arm is configured to deploy among the chords of the native atrio-ventricular valve to a distance sufficient to recruit and deflect at least primary and secondary chords of the native atrio-ventricular valve.

26. The apparatus according to claim 25, wherein the at least one arm is configured to deploy among the chords of the native atrio-ventricular valve to a distance sufficient to further recruit and deflect tertiary chords of the native atrio-ventricular valve.

* * * * *